United States Patent [19]

Grell et al.

[11] Patent Number: 4,735,959

[45] Date of Patent: Apr. 5, 1988

[54] CARBOXYLIC ACID AMIDES AND PHARMACEUTICAL COMPOSITIONS CONTAINING THEM

[75] Inventors: Wolfgang Grell, Gerhart Griss, both of Biberach; Robert Sauter, Laupheim; Rudolf Hurnaus, Biberach; Eckhard Rupprecht, Aulendorf-Tannhausen; Nikolaus Kaubisch, Bad Kreuznach; Joachim Kähling; Bernhard Eisele, both of Biberach, all of Fed. Rep. of Germany

[73] Assignee: Dr. Karl Thomae GmbH, Biberach an der Riss, Fed. Rep. of Germany

[21] Appl. No.: 734,252

[22] Filed: May 14, 1985

Related U.S. Application Data

[63] Continuation of Ser. No. 510,071, Jun. 30, 1983, abandoned, which is a continuation-in-part of Ser. No. 335,565, Dec. 29, 1981, abandoned.

[30] Foreign Application Priority Data

Jan. 10, 1981 [DE] Fed. Rep. of Germany ....... 3100575
Jul. 6, 1982 [DE] Fed. Rep. of Germany ....... 3225155
Jul. 6, 1982 [DE] Fed. Rep. of Germany ....... 3225188

[51] Int. Cl.$^4$ .............. A61K 31/445; A61K 31/165; C07D 295/14; C07C 103/82

[52] U.S. Cl. ................................. 514/357; 546/234; 546/19; 546/188; 546/189; 546/194; 546/207; 546/221; 546/222; 546/226; 546/230; 546/256; 546/262; 546/265; 546/273; 546/281; 546/282; 546/283; 546/322; 546/330; 546/335; 546/337; 546/145; 546/146; 546/147; 546/187; 540/450; 540/480; 540/481; 540/483; 540/585; 540/596; 540/597; 540/600; 544/59; 544/60; 544/61; 544/78; 544/82; 544/117; 544/129; 544/131; 544/148; 544/159; 544/163; 544/166; 544/168; 544/280; 544/360; 544/364; 544/374; 544/393; 548/515; 548/517; 548/567; 548/568; 549/452; 558/404; 558/405; 558/406; 558/413; 558/414; 558/415; 558/416; 560/9; 560/19; 560/27; 560/37; 560/42; 560/251; 562/431; 562/432; 562/444; 562/448; 562/450; 564/85; 562/449; 564/86; 564/89; 514/155; 514/156; 514/157; 514/158; 514/212; 514/215; 514/216; 514/222; 514/228; 514/229; 514/234; 514/254; 514/252; 514/255; 514/278; 514/307; 514/316; 514/318; 514/326; 514/327; 514/331; 514/332; 514/336; 514/412; 514/414; 514/422; 514/428; 514/467; 514/478; 514/482; 514/484; 514/487; 514/522; 514/533; 514/539; 514/562; 514/563; 514/603; 514/616; 514/617; 514/619; 514/620; 514/621; 514/622; 514/866

[58] Field of Search .............. 514/357, 155, 156, 157, 514/158, 212, 215, 216, 222, 228, 229, 234, 254, 252, 255, 278, 307, 316, 318, 326, 327, 331, 332, 336, 412, 414, 422, 428, 467, 478, 482, 484, 487, 522, 533, 539, 562, 563, 603, 616, 617, 619, 620, 621, 622, 866; 546/234, 19, 145, 146, 147, 187, 188, 189, 194, 207, 221, 222, 226, 230, 256, 262, 265, 273, 281, 282, 283, 322, 330, 335, 337; 540/450, 480, 481, 483, 585, 596, 597, 600; 544/59, 60, 61, 78, 82, 117, 129, 131, 148, 159, 163, 166, 168, 280, 360, 364, 374, 393; 548/515, 517, 567, 568; 549/452; 558/404, 405, 406, 413, 414, 415, 416; 560/9, 19, 27, 37, 42, 251; 562/431, 432, 444, 448, 449, 450; 564/85, 86, 89

[56] References Cited

U.S. PATENT DOCUMENTS 4,172,947 10/1979 Warner et al. ................... 548/346
4,186,199 1/1980 Glamkowski et al. ............ 424/274

FOREIGN PATENT DOCUMENTS 764,238 9/1971 Belgium.
0058779 9/1982 European Pat. Off..
2225165 11/1974 France.
2370723 6/1978 France.

*Primary Examiner*—Norma S. Milestone
*Attorney, Agent, or Firm*—Weissenberger, Hammond & Littell

[57] ABSTRACT

There are described novel carboxylic acid derivatives of the formula

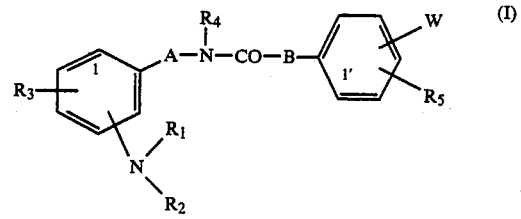

and derivatives of the formula

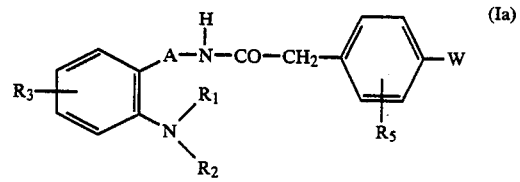

and the addition salts thereof, which exhibit an effect on the intermediary metabolism. Furthermore, the compounds of Formula Ia as well as the compounds of Formula I possess blood-sugar lowering properties.

16 Claims, No Drawings

CARBOXYLIC ACID AMIDES AND PHARMACEUTICAL COMPOSITIONS CONTAINING THEM

This is a continuation of copending application Ser. No. 510,071, filed June 30, 1983, now abandoned; which in turn is a continuation-in-part of application Ser. No. 335,565, filed Dec. 29, 1981, now abandoned.

The present invention relates to novel carboxylic acid amides of the formula

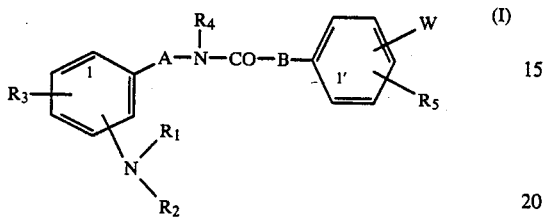

and, when they contain an asymmetric carbon atom, to their optically active antipodes, to their salts, especially to their non-toxic, pharmacologically acceptable salts with inorganic or organic acids and bases, to pharmaceutical compositions containing them, and to processes for their preparation. The novel compounds exhibit valuable pharmacological properties, especially an effect on intermediary metabolism, preferably, however, a blood-sugar lowering activity.

In Formula I above, $R_1$ and $R_2$, which may be the same or different, each represent an alkyl group having from 1 to 6 carbon atoms or a cycloalkyl group having from 5 to 7 carbon atoms; or $R_1$ and $R_2$ together with the nitrogen atom to which they are attached, represent an unbranched alkyleneimino group having from 3 to 6 carbon atoms, which may be unsubstituted or substituted by one or two alkyl groups having from 1 to 3 carbon atoms each or by a hydroxyl group, or wherein a methylene group may be replaced by a carbonyl group, by an oxygen or sulfur atom, or by an imino group, which may be substituted by an alkyl group having from 1 to 3 carbon atoms, an aralkyl group having from 7 to 10 carbon atoms, or a phenyl or halogen-phenyl group, or wherein an ethylene group may be replaced by an o-phenylene group; an unbranched alkyleneimino group having from 7 to 9 carbon atoms which may be substituted by one or two alkyl groups having from 1 to 3 carbon atoms each; an unbranched alkenyleneimino group having from 4 to 6 carbon atoms; a saturated or partly unsaturated azabicycloalkyl group having from 6 to 10 carbon atoms; an aza-1,4-dioxa-spiro-alkyl group having from 6 to 8 carbon atoms; or a decamethyleneimino group;

$R_3$ represents a hydrogen or halogen atom; a trifluoromethyl, alkyl, hydroxyl, alkoxy, phenylalkoxy, alkanoyloxy, mercapto, alkylmercapto, alkylsulfinyl, alkylsulfonyl, nitro, amino, cyano, alkanoyl, carboxyl, alkoxycarbonyl, aminocarbonyl, alkylaminocarbonyl, dialkylaminocarbonyl, piperidino, aminosulfonyl, alkylamino, dialkylamino, alkanoylamino, alkoxycarbonylamino, or alkylsulfonylamino group, whereby each alkyl moiety in the aforementioned groups may contain from 1 to 3 carbon atoms each; an aralkoxy group having from 7 to 10 carbon atoms; or an arylcarbonylamino group;

$R_4$ represents a hydrogen atoms or an alkyl group having from 1 to 3 carbon atoms;

$R_5$ represents a hydrogen atom, a halogen atom, or an alkyl group having from 1 to 3 carbon atoms;

A represents a single bond; a methylene or ethylene group optionally substituted by an alkyl group having from 1 to 6 carbon atoms; a methylene or ethylene group substituted by two alkyl groups having from 1 to 3 carbon atoms each; a methylene group substituted by a cycloalkyl group having from 3 to 7 carbon atoms, by an alkenyl group having from 3 to 5 carbon atoms, by a hydroxyalkyl, alkoxyalkyl, aralkyl, cyano, carboxyl, alkoxycarbonyl, aminocarbonyl, alkylaminocarbonyl, or dialkylaminocarbonyl group, by an unbranched alkyleneiminocarbonyl group having from 4 to 6 carbon atoms, by a phenylalkylaminocarbonyl, N-alkyl-phenylalkylaminocarbonyl, or bis-phenylalkyl-aminocarbonyl group, by an aryl group having 6 to 10 carbon atoms which may be substituted by one or two halogen atoms or one or two alkyl, hydroxyl, alkoxy, phenylalkoxy, alkylsulfenyl, alkylsulfinyl, or alkylsulfonyl groups, the substituents being the same or different, or by a heteroaryl group having 4, 5, 8, or 9 carbon atoms and containing one or two nitrogen atoms, whereby each of the aforementioned alkyl moieties may contain from 1 to 3 carbon atoms; a cycloalkylidene group having from 3 to 7 carbon atoms; or a vinylidene group of the formula

where $R_6$ and $R_7$ each represent a hydrogen atom or $R_6$ and $R_7$ together with the carbon atom to which they are attached represent a cycloalkyl methylidene, whereby the cycloalkyl moiety may contain from 3 to 7 carbon atoms, an aryl methylidene or aralkyl methylidene group, whereby each methylidene moiety may be substituted by an alkyl group having from 1 to 5 carbon atoms, an alkylidene group having from 2 to 11 carbon atoms, or a cycloalkylidene group having from 5 to 7 carbon atoms;

B represents a methylene or ethylene group optionally substituted by an alkyl group having from 1 to 3 carbon atoms; and W represents a hydrogen or halogen atom, a formyl, cyano, or nitro group, an amino group optionally substituted by an alkanoyl group having from 1 to 3 carbon atoms, an alkyl group having from 1 to 3 carbon atoms optionally substituted by a hydroxyl, carboxyl, or alkoxycarbonyl group or by two alkoxycarbonyl groups having altogether from 2 to 4 carbon atoms each, an alkenyl group having from 2 to 5 carbon atoms substituted by a carboxyl or alkoxycarbonyl group having altogether from 2 to 4 carbon atoms, an alkanoyl group having from 1 to 3 carbon atoms, a dialkoxymethyl or trialkoxymethyl group having from 1 to 3 carbon atoms in each alkyl moiety, an alkenyloxycarbonyl group having altogether from 4 to 6 carbon atoms, an alkylenedioxymethyl group having 2 or 3 carbon atoms in the alkylene moiety, a 1,3-oxazoline-2-yl group, an aminocarbonyl group optionally substituted by one or two alkyl groups having from 1 to 4 carbon atoms in each alkyl moiety, an unbranched alkyleneiminocarbonyl group having altogether from 5 to 8 carbon atoms, a morpholinocarbonyl group, a (dialkyldioxolane-yl)-alkoxycarbonyl group having altogether from 7 to 10 carbon atoms, or a carboxyl group and esters thereof, whereby alkyl esters having from 1 to 6 carbon atoms in the alkyl moiety may each be substituted with the exception of the 1-position of the alkyl moiety by a hydroxyl, alkoxy, amino, alkylamino, dialkylamino, alkyleneimino, 1,3-dimethyl-xanthine-7-yl, alkanoyloxy, aroyloxy, aralkanoyloxy, or pyridinecarbonyloxy group or by two hydroxyl groups, whereby a methyl or methylene group in each case may be substituted only by one hydroxy group, or by a group of the formula

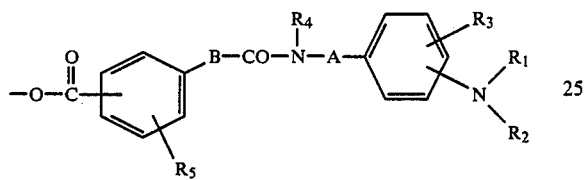

where A, B, and $R_1$ to $R_5$ are as defined above and whereby each alkyl substituent in the aforementioned alkyl esters may contain from 1 to 3 carbon atoms and the alkylene group may contain from 4 to 6 carbon atoms.

Suitable meanings in the definitions of radicals mentioned above include the following:

For $R_1$ and $R_2$ together with the nitrogen atom: a dimethylamino, diethylamino, dipropylamino, dibutylamino, diisobutylamino, dipentylamino, dihexylamino, N-methyl-N-ethylamino, N-methyl-N-propylamino, N-methyl-N-isopropylamino, N-isopropyl-N-propylamino, N-isobutyl-N-propylamino, N-methyl-N-butylamino, N-ethyl-N-butylamino, N-ethyl-N-isopropylamino, N-ethyl-N-pentylamino, N-propyl-N-butylamino, N-methyl-N-cyclopentylamino, N-ethyl-N-cyclopentylamino, N-methyl-N-cyclohexylamino, N-ethyl-N-cyclohexylamino, N-propyl-N-cyclohexylamino, N-isobutyl-N-cyclohexylamino, pyrrolidino, piperidino, hexamethyleneimino, heptamethyleneimino, octamethyleneimino, nonamethyleneimino, decamethyleneimino, dimethylazetidino, methyl-pyrrolidino, dimethyl-pyrrolidino, ethyl-pyrrolidino, methyl-piperidino, dimethyl-piperidino, ethyl-piperidino, diethyl-piperidino, methyl-ethyl-piperidino, propyl-piperidino, methyl-propyl-piperidino, isopropyl-piperidino, 3,3-dimethyl-piperidino, cis-3,5-dimethyl-piperidino, trans-3,5-dimethyl-piperidino, tetrahydro-pyridino, morpholino, thiomorpholino, piperazino, N-methyl-piperazino, N-ethyl-piperazino, N-propyl-piperazino, N-isopropyl-piperazino, N-benzyl-piperazino, N-(2-phenyl-ethyl)-piperazino, N-(3-phenyl-propyl)-piperazino, N-phenyl-piperazino, N-fluorophenyl-piperazino, N-chlorophenyl-piperazino, N-bromophenyl-piperazino, hydroxy-pyrrolidino, hydroxy-piperidino, hydroxy-hexamethyleneimino, pyrrolidone-1-yl, piperidone-1-yl, hexahydroazepinone-1-yl, tetrahydro-isoquinoline-2-yl, octahydro-isoquinoline-2-yl, decahydro-isoquinoline-2-yl, dihydro-isoindole-2-yl, hexahydro-isoindole-2-yl, octahydro-isoindole-2-yl, tetrahydro-3-benzazepine-3-yl, decahydro-3-benzazepine-3-yl, 3-aza-bicyclo[3.2.0]heptane-3-yl, 3-aza-bicyclo[3.2.1]octane-3-yl, 3-aza-bicyclo[3.2.2]nonane-3-yl, 1,4-dioxa-7-aza-spiro[4,4]nonane-7-yl, 1,4-dioxa-7-aza-spiro[4,5]decane-7-yl, 1,4-dioxa-8-aza-spiro[4,5]-decane-8-yl, or 1,4-dioxa-8-aza-spiro[4,6]undecane-8-yl group;

For $R_3$: a hydrogen, fluorine, chlorine, bromine, or iodine atom or a methyl, ethyl, propyl, isopropyl, hydroxyl, methoxy, ethoxy, propoxy, isopropoxy, acetoxy, propionyloxy, mercapto, methylmercapto, ethylmercapto, propylmercapto, isopropylmercapto, methylsulfinyl, ethylsulfinyl, methylsulfonyl, n-propylsulfonyl, trifluoromethyl, nitro, cyano, formyl, acetyl, propionyl, aminosulfonyl, amino, methylamino, ethylamino, propylamino, dimethylamino, diethylamino, dipropylamino, diisopropylamino, N-methyl-N-ethylamino, N-methyl-N-isopropylamino, N-ethyl-N-propylamino, formylamino, acetylamino, propionylamino, methylsulfonylamino, ethylsulfonylamino, propylsulfonylamino, isopropylsulfonylamino, carboxyl, methoxycarbonyl, ethoxycarbonyl, propoxycarbonyl, isopropoxycarbonyl, methoxycarbonylamino, ethoxycarbonylamino, propoxycarbonylamino, isopropoxycarbonylamino, benzoylamino, benzyloxy, 1-phenyl-ethoxy, 2-phenyl-ethoxy, 3-phenyl-propoxy, aminocarbonyl, methylaminocarbonyl, ethylaminocarbonyl, isopropylaminocarbonyl, dimethylaminocarbonyl, diethylaminocarbonyl, dipropylaminocarbonyl, methyl-ethylaminocarbonyl, or methyl-propylaminocarbonyl group;

For $R_4$: a hydrogen atom or a methyl, ethyl, propyl, or isopropyl group;

For $R_5$: a hydrogen, fluorine, chlorine, bromine, or iodine atom or a methyl, ethyl, propyl, or isopropyl group;

For A: a single bond or a methylene, ethylidene, ethyl-methylene, propyl-methylene, isopropyl-methylene, butyl-methylene, pentyl-methylene, hexyl-methylene, dimethyl-methylene, diethyl-methylene, dipropyl-methylene, methyl-ethyl-methylene, methyl-propyl-methylene, ethyl-propyl-methylene, ethyl-isopropyl-methylene, allyl-methylene, 2-butene-1-yl-methylene, 3-butene-1-yl-methylene, 4-pentene-1-yl-methylene, ethylene, methyl-ethylene, ethyl-ethylene, propyl-ethylene, dimethyl-ethylene, cyclopropyl-methylene, cyclobutyl-methylene, cyclopentyl-methylene, cyclohexyl-methylene, cycloheptyl-methylene, cyclopropylidene, cyclobutylidene, cyclopentylidene, cyclohexylidine, cycloheptylidene, carboxymethylene, methoxycarbonyl-methylene, ethoxycarbonyl-methylene, propoxycarbonyl-methylene, hydroxymethyl-methylene, 1-hydroxyethyl-methylene, 2-hydroxyethyl-methylene, 1-hydroxypropyl-methylene, 2-hydroxy-propyl-methylene, 3-hydroxypropyl-methylene, methoxy-methyl-methylene, ethoxymethyl-methylene, propoxymethyl-methylene, isopropoxy-methyl-methylene, 1-methoxyethyl-methylene, 2-methoxy-ethylmethylene, 2-ethoxyethyl-methylene, 3-methoxypropyl-methylene, cyano-methylene, aminocarbonyl-methylene, methylaminocarbonyl-methylene, dimethylaminocarbonyl-methylene, ethylaminocarbonyl-methylene, diethylaminocarbonyl-methylene, propylaminocarbonyl-methylene, dipropylaminocarbonyl-methylene, benzylaminocarbonyl-methylene, 2-phenylethylaminocarbonyl-methylene, pyrrolidinocarbonyl-methylene, piperidinocarbonyl-methylene, hexamethyleneiminocarbonyl-methylene, phenyl-methylene, napthyl-methylene, fluorophenyl-methylene, chlorophenyl-methylene, bromophenyl-methylene, methylphenyl-methylene, ethylphenyl-methylene, isopropylphenyl-methylene, hydroxyphenyl-methylene, methoxyphenyl-methylene, ethoxyphenyl-methylene, n-propoxyphenyl-methylene, benzyloxyphenyl-methylene, 2-phenylethoxyphenyl-methylene, 3-phenylpropoxyphenyl-methylene, methylsulfenylphenyl-methylene, ethylsulfenylphenyl-methylene, methylsulfinylphenyl-methylene, n-propylsulfinylphenyl-methylene, methylsulfonylphenyl-methylene, ethylsulfonylphenyl-methylene, isopropylsulfonylphenyl-methylene, methylnaphthyl-methylene, hydroxynaphthyl-methylene, methoxynaphthyl-methylene, dichlorophenyl-methylene, chlorobromophenyl-methylene, dimethylphenyl-methylene, diisopropylphenyl-methylene, chloro-methylphenyl-methylene, dimethoxyphenyl-methylene, methylmethoxyphenyl-methylene, chloro-methoxyphenyl-methylene, bromo-methoxyphenyl-methylene, pyridyl-methylene, pyrimidyl-methylene, quinolyl-methylene, isoquinolyl-methylene, quinazolyl-methylene, benzyl-methylene, 1-phenylethyl-methylene, 2-phenylethyl-methylene, 1-phenylpropyl-methylene, 2-phenylpropyl-methylene, 3-phenylpropyl-methylene, vinylidene, methylvinylidene, dimethyl-vinylidene, ethyl-vinylidene, diethyl-vinylidene, propyl-vinylidene, dipropyl-vinylidene, ethyl-methyl-vinylidene, ethyl-propyl-vinylidene, methyl-propyl-vinylidene, n-butyl-vinylidene, isobutyl-vinylidene, sec.butyl-vinylidene, n-pentyl-vinylidene, n-hexyl-vinylidene, dibutyl-vinylidene, dipentylvinylidene, cyclopentyl-vinylidene, cyclohexyl-vinylidene, phenyl-vinylidene, benzyl-vinylidene, 1-phenethyl-vinylidene, 2-phenethyl-vinylidene, phenyl-methyl-vinylidene, benzyl-methyl-vinylidene, cyclopropylidene-methylene, cyclopentylidene-methylene, cyclohexylidene-methylene, or cycloheptylidene-methylene group;

For B: a methylene, ethylene, ethylidene, ethyl-methylene, propyl-methylene, or isopropyl-methylene group; and For W: a hydrogen, chlorine, bromine, or iodine atom or a methyl, ethyl, propyl, isopropyl, hydroxymethyl, 1-hydroxyethyl, 2-hydroxyethyl, 1-hydroxypropyl, 3-hydroxypropyl, carboxymethyl, 1-carboxyethyl, 2-carboxyethyl, 3-carboxypropyl, methoxycarbonyl-methyl, ethoxycarbonyl-methyl, propoxycarbonyl-methyl, 2-methoxycarbonyl-ethyl, 2-ethoxycarbonyl-ethyl, 2-isopropoxycarbonyl-ethyl, 3-ethoxycarbonyl-propyl, bis-(methoxycarbonyl)-methyl, bis-(ethoxycarbonyl)-methyl, 2,2-bis-(methoxycarbonyl)-ethyl, 2,2-bis-(ethoxycarbonyl)-ethyl, 2,2-bis-(isopropoxycarbonyl)-ethyl, 2,2-bis-(carboxy)-ethyl, carboxy-vinyl, carboxy-propenyl, carboxy-pentenyl, methoxycarbonyl-vinyl, ethoxycarbonyl-vinyl, propoxycarbonyl-vinyl, formyl, acetyl, propionyl, dimethoxy-methyl, diethoxy-methyl, dipropoxy-methyl, trimethoxy-methyl, triethoxy-methyl, 1,2-ethylenedioxy-methyl, 1,3-propylenedioxy-methyl, cyano, nitro, amino, formylamino, acetamino, propionylamino, 1,3-oxazoline-2-yl, aminocarbonyl, methylaminocarbonyl, ethylaminocarbonyl, propylaminocarbonyl, isopropylaminocarbonyl, butylaminocarbonyl, dimethylaminocarbonyl, diethylaminocarbonyl, dipropylaminocarbonyl, dibutylaminocarbonyl, pyrrolidinocarbonyl, piperidinocarbonyl, hexamethyleneiminocarbonyl, heptamethyleneiminocarbonyl, morpholinocarbonyl, carboxyl, methoxycarbonyl, ethoxycarbonyl, propoxycarbonyl, isopropoxycarbonyl, butoxycarbonyl, isobutoxycarbonyl, tert.butoxycarbonyl, pentoxycarbonyl, hexoxycarbonyl, heptoxycarbonyl, octoxycarbonyl, allyloxycarbonyl, crotyloxycarbonyl, benzyloxycarbonyl, 1-phenyl-ethoxycarbonyl, 2-phenylethoxycarbonyl, 3-phenylpropoxycarbonyl, 2-hydroxyethoxycarbonyl, 2-hydroxypropoxycarbonyl, 3-hydroxypropoxycarbonyl, 2-methoxyethoxycarbonyl, 2-ethoxyethoxycarbonyl, 2-propoxyethoxycarbonyl, (2,2-dimethyl-dioxolane-4-yl)-methoxycarbonyl, 2-(2,2-dimethyl-dioxolane-4-yl)-ethoxycarbonyl, (2,2-diethyl-dioxolane-4-yl)-methoxycarbonyl, 2-(2,2-diethyl-dioxolane-4-yl)-ethoxycarbonyl, 3-(2,2-dimethyl-dioxolane-4-yl)-propoxycarbonyl, 2-amino-ethoxycarbonyl, 2-dimethylaminoethoxycarbonyl, 2-diethylaminoethoxycarbonyl, 2-piperidinoethoxycarbonyl, 2-(1,3-dimethyl-xanthine-7-yl)-ethoxycarbonyl, 2-acetoxy-ethoxycarbonyl, 2-benzoyloxy-ethoxycarbonyl, 2-phenylacetoxy-ethoxycarbonyl, 2-pyridinecarbonyloxy-ethoxycarbonyl, 2,3-dihydroxypropoxycarbonyl, 3,4-dihydroxy-butoxycarbonyl, 2-{4-[(1-(2-piperidino-phenyl)-1-ethyl)-aminocarbonylmethyl]-benzoyloxy}-ethoxycarbonyl, 3-{4-[(1-(2-piperidinophenyl)-1-ethyl)l-aminocarbonylmethyl]-benzoyloxy}-propoxycarbonyl, 2-{4-[(1-(2-piperidinophenyl)-1-butyl)-aminocarbonylmethyl]-benzoyloxy}-ethoxycarbonyl, or 3-{4-[(1-(2-piperidinophenyl)-1-butyl)-aminocarbonylmethyl]-benzoyloxy}-propoxycarbonyl group.

Preferred compounds of Formula I are, however, those wherein $R_1$ and $R_2$ together with the nitrogen atom to which they are attached represent a dialkylamino or N-alkylcyclohexylamino group, where each alkyl moiety may contain from 1 to 4 carbon atoms, an unbranched alkyleneimino group having from 3 to 6 carbon atoms optionally substituted by one or two methyl groups, a hydroxy-piperidino, piperidone-1-yl, tetrahydropyridino, morpholino, thiomorpholino, N-methylpiperazino, N-benzylpiperazino, N-chlorophenylpiperazino, heptamethyleneimino, or octamethyleneimino group, a saturated or partly unsaturated azabicycloalkyl group having from 7 to 9 carbon atoms, an unbranched alkyleneimino group having from 4 to 6 carbon atoms, where one ethylene group is replaced by an o-phenylene group, or a 1,4-dioxa-aza-spiroalkyl group having 7 or 8 carbon atoms;

$R_3$ represents a hydrogen, fluorine, chlorine, bromine, or iodine atom or a methyl, trifluoromethyl, hydroxyl, methoxy, benzyloxy, acetoxy, mercapto, methylmercapto, nitro, amino, dimethylamino, acetylamino, methylsulfonylamino, benzoylamino, ethoxycarbonyl-amino, cyano, carboxyl, methoxycarbonyl, ethoxycarbonyl, aminocarbonyl, acetyl, or aminosulfonyl group;

R$_4$ represents a hydrogen atom or a methyl group;

R$_5$ represents a hydrogen atom, a chlorine atom, or a methyl group;

A represents a bond; a methylene group optionally substituted by an alkyl group having from 1 to 6 carbon atoms, by an alkenyl group having from 3 to 5 carbon atoms, by a phenyl group optionally substituted by a halogen atom or a methyl, hydroxyl, methoxy, benzyloxy, or methylmercapto group, by a pyridyl, cyclohexyl, carboxyl, cyano, aminocarbonyl, methoxycarbonyl, ethoxycarbonyl, or hydroxymethyl group, or by a methoxyalkyl or phenylalkyl group where the alkyl moiety may contain one or two carbon atoms; a dimethyl-methylene, cyclopropylidene, or ethylene group; or a vinylidene group of the formula

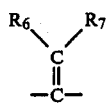 (A')

where R$_6$ and R$_7$ each represent a hydrogen atom or R$_6$ and R$_7$ together with the carbon atoms to which they are attached represent an alkylidene group having from 2 to 9 carbon atoms, a phenylalkylidene group having from 1 to 3 carbon atoms in the alkylidene moiety, or a cycloalkylidene group having 5 or 6 carbon atoms;

B represents a methylene, ethylidene, or ethylene group; and

W represents a hydrogen atom; a methyl, ethyl, hydroxymethyl, formyl, carboxyl, cyano, 2-carboxy-ethenyl, or 2-alkoxycarbonyl-ethenyl group; an alkyl group substituted by a carboxyl group or by one or two alkoxycarbonyl groups having altogether from 2 to 4 carbon atoms each; a carbonyl group substituted by a methyl, ethyl, (2,2-dimethyl-dioxolane-4-yl)-methoxy, benzyloxy, pyridylmethoxy, amino, alkylamino, dialkylamino, piperidino, or morpholino group, whereby each alkyl moiety in the aforementioned groups may contain from 1 to 3 carbon atoms; an alkoxycarbonyl group having altogether from 2 to 5 carbon atoms optionally substituted by one or two hydroxyl groups with the exception of the 1-position and whereby a methyl or methylene group in each case can be substituted only by one hydroxyl group; or a group of the formula

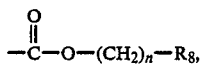

where n represents the number 2, 3, or 4 and R$_8$ represents a methoxy, ethoxy, acetoxy, benzoyloxy, pyridinecarbonyloxy, or dialkylamino group having from 1 to 3 carbon atoms in each alkyl moiety, a 1,3-dimethyl-xanthine-7-yl group, or a group of the formula

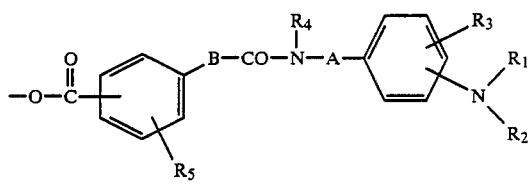

where A, B, and R$_1$ to R$_5$ are as defined above, especially, however, those compounds, wherein the radical

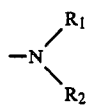

is in the 2-position and the radical W is in the 4'-position, and, if they contain an asymmetric carbon atom, their optically active antipodes and their salts.

Particularly preferred compounds are those of the formula

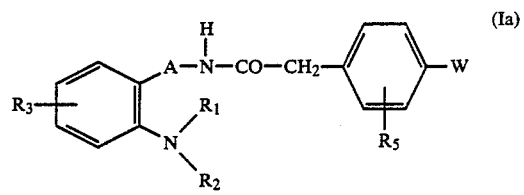 (Ia)

wherein

R$_1$ and R$_2$ together with the nitrogen atom to which they are attached represent a dimethylamino group, an unbranched alkyleneimino group having from 3 to 6 carbon atoms optionally substituted by one or two methyl groups, or a tetrahydropyridino, hexamethyleneimino, octamethyleneimino, or 2-octahydro-isoindolo group;

R$_3$ represents a hydrogen, fluorine, or chlorine atom or a methoxy or methyl group;

R$_5$ represents a hydrogen or chlorine atom;

A represents a methylene group optionally substituted by an alkyl group having from 1 to 5 carbon atoms, by an alkenyl group having from 3 to 5 carbon atoms, by a hydroxymethyl group, by a methoxyalkyl or phenylalkyl group whereby each alkyl moiety may contain 1 or 2 carbon atoms, by a cyano, aminocarbonyl, carboxyl, methoxycarbonyl, ethoxycarbonyl, cyclohexyl, or pyridyl group, or by a phenyl group optionally substituted by a fluorine, chlorine, or bromine atom or a methyl, hydroxyl, methoxy, benzyloxy, or methylmercapto group; a dimethyl-methylene or ethylene group; or a vinylidene group of the formula

 (A'')

where R$_6$ and R$_7$ each represent a hydrogen atom or R$_6$ and R$_7$ together with the carbon atom to which they are attached represent an alkylidene group having from 2 to 9 carbon atoms, a phenylalkylidene group having from 1 to 3 carbon atoms in the alkylidene moiety, or a cyclohexylidene group; and W represents a methyl, hydroxymethyl, formyl, cyano, carboxyl, carboxymethyl, 2-carboxy-ethyl, or 2-carboxyethenyl group; an alkoxycarbonyl group having altogether from 2 to 5 carbon atoms optionally substituted in the alkyl moiety by one or two hydroxyl groups with the exception of the 1-position and whereby a methyl or methylene group in each case can be substituted only by one hydroxyl group; an alkoxycarbonyl-methyl, 2-alkoxycarbonyl-ethyl, or 2-alkoxycarbonyl-ethenyl group, whereby the alkoxy group may contain from 1 to 3 carbon atoms; a (2,2-dimethyl-dioxolane-4-yl)-methoxycarbonyl group; or a group of the formula

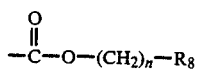

where n represents the number 2 or 3 and $R_8$ represents a methoxy, diethylamino, pyridinecarbonyloxy, or 1,3-dimethyl-xanthine-7-yl group.

An especially preferred aspect of the invention comprises compounds of the formula

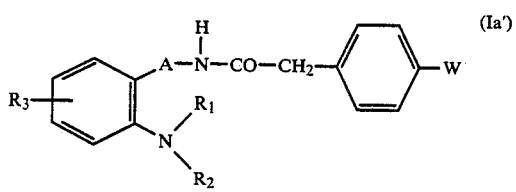

wherein $R_1$ and $R_2$ together with the nitrogen atom to which they are attached represent a dimethylamino, pyrrolidino, methyl-pyrrolidino, piperidino, methyl-piperidino, dimethyl-piperidino, tetrahydropyridino, 2-octahydro-isoindolo, or hexamethyleneimino group;

$R_3$ represents a hydrogen, fluorine, or chlorine atom or a methyl group;

A represents a methylene group optionally substituted by a cyclohexyl, phenyl, methoxycarbonyl, ethoxycarbonyl, or alkyl group having from 1 to 3 carbon atoms, a dimethyl-methylene group, or a vinylidene group of the formula

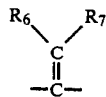

whereby $R_6$ and $R_7$ each represent a hydrogen atom or $R_6$ and $R_7$ with the carbon atoms to which they are attached represent a cyclohexylidene group; and W represents a methyl, hydroxymethyl, or carboxymethyl group, a carbonyl group substituted by a hydrogen atom or by a methyl, hydroxyl, methoxy, ethoxy, propoxy, isopropoxy, 2-hydroxyethoxy, 2-methoxyethoxy, (2,2-dimethyl-dioxolane-4-yl)-methoxy, or 2-diethylaminoethoxy group, and with the proviso that they contain an asymmetric carbon atom, their optically active antipodes, and their nontoxic, pharmacologically acceptable addition salts with inorganic or organic acids or bases.

According to the invention the new compounds can be prepared according to the following procedures:

Method A:

An amine of the general formula

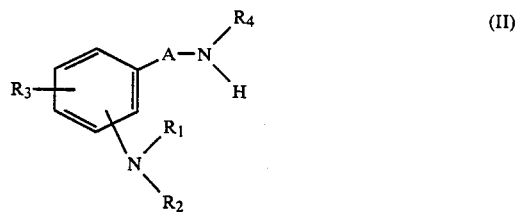

wherein A and $R_1$ to $R_4$ are as defined above or with the proviso that A represents one of the aforementioned vinylidene groups, their tautomers, or their lithium or magnesium halogenide complex, is acylated with a carboxylic acid of the general formula

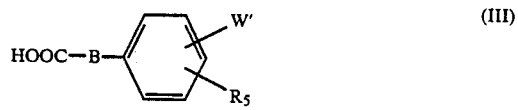

wherein $R_5$ and B are as defined above and W' has the meanings mentioned before for W or represents a carboxyl group protected by a protective radical, or with their reactive derivatives optionally prepared in the reaction mixture.

Suitable reactive derivatives of a compound of Formula III include, for example, the esters thereof, such as the methyl, ethyl, or benzyl ester, the thioesters thereof, such as the methylthio or ethylthioester, the halogenides thereof, such as the acid chloride, and the anhydrides or imidazolides thereof.

The reaction is conveniently carried out in a solvent such as methylene chloride, chloroform, carbon tetrachloride, ether, tetrahydrofuran, dioxane, benzene, toluene, acetonitrile, or dimethylformamide, optionally in the presence of an acid-activating agent or of a dehydrating agent, e.g., in the presence of ethyl chloroformate, thionyl chloride, phosphorous trichloride, phosphorus pentoxide, N,N'-dicyclohexylcarbodiimide, N,N'-dicyclohexylcarbodiimide/N-hydroxy-succinimide, N,N'-carbonyldiimidazole, N,N'-thionyldiimidazole, or triphenyl phosphine/carbon tetrachloride, or of an agent activating the amino group, e.g., phosphorus chloride, and optionally in the presence of an inorganic base such as sodium carbonate or a tertiary organic base such as sodium carbonate or a tertiary organic base such as triethyl amine or pyridine, which simultaneously may serve as solvent, at temperatures of from about −25° to 250° C., preferably, however, at temperatures between about −10° C. and the boiling temperature of the solvent used. The reaction can also be carried out without a solvent; furthermore, the water which is formed during the reaction can be separated by azeotropic distillation, e.g., by heating with toluene in a water separator funnel or by addition of a drying agent such as magnesium sulfate or a molecular sieve.

If necessary, the subsequent removal of a protective radical is preferably carried out hydrolytically, appropriately either in the presence of an acid such as hydrochloric acid, sulfuric acid, phosphoric acid, or trichloroacetic acid or in the presence of a base such as sodium hydroxide or potassium hydroxide in a suitable solvent such as water, methanol, ethanol, ethanol/water, water/isopropanol, or water/dioxane at temperatures of from about −10° to 120° C., e.g., at temperatures between room temperature and the boiling temperature of the reaction mixture.

A tert.butyl radical used as protective radical can also be split off thermolytically, optionally in an inert solvent such as methylene chloride, chloroform, benzene, toluene, tetrahydrofuran, or dioxane and preferably in the presence of a catalytic amount of an acid such as p-toluene-sulfonic acid, sulfuric acid, phosphoric acid, or polyphosphoric acid.

Furthermore, a benzyl radical used as protective radical can also be split off hydrogenolytically in the presence of a hydrogenation catalyst such as palladium/charcoal in a suitable solvent such as methanol, ethanol, ethanol/water, glacial acetic acid, ethyl acetate, dioxane, or dimethyl formamide.

Method B:

To prepare a compound of Formula I wherein W represents a carboxyl group a compound of the general formula

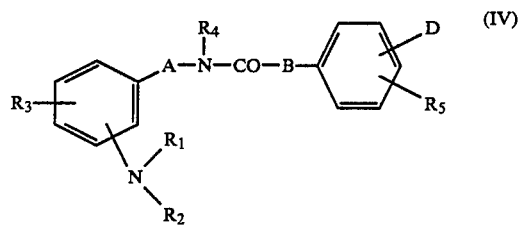 (IV)

wherein $R_1$ to $R_5$, A, and B are as defined above and D represents a group which is transformable into a carboxyl group, an alkyl group having from 1 to 3 carbon atoms substituted by a carboxyl group, or an alkenyl group having from 2 to 5 carbon atoms substituted by a carboxyl group, by means of hydrolysis, thermolysis, or hydrogenolysis, is split by hydrolysis, thermolysis, or hydrogenolysis.

Hydrolyzable groups include, for example, functional derivatives of the carboxyl, carboxymethyl, or 2-carboxymethyl group such as their unsubstituted or substituted amides, esters, thioesters, orthoesters, iminoethers, amidines, or anhydrides, a nitrile group, a malonic ester-(1)-yl group, a tetrazolyl group, or an optionally substituted 1,3-oxazole-2-yl or 1,3-oxazoline-2-yl group. Thermolytically cleavable groups include, for example, esters with tertiary alcohols, such as the tert.butyl ester. Hydrogenolytically cleavable groups include, for example, aralkyl groups such as the benzyl group.

The hydrolysis is appropriately carried out either in the presence of an acid such as hydrochloric acid, sulfuric acid, phosphoric acid, or trichloroacetic acid or in the presence of a base such as sodium hydroxide or potassium hydroxide in a suitable solvent such as water, water/methanol, ethanol, water/ethanol, water/isopropanol, or water/dioxane at temperatures of from about −10° to 120° C., for example, at temperatures between room temperature and the boiling temperature of the reaction mixture.

If D in a compound of Formula IV represents a nitrile or aminocarbonyl group, these groups can also be transformed into the carboxyl group with a nitrile, for example, sodium nitrite, in the presence of an acid such as sulfuric acid, whereby preferably this acid is simultaneously used as solvent, at temperatures of from about 0° to 50° C.

If D in a compound of Formula IV represents, for example, a tert.butyloxycarbonyl group, the tert.butyl group can also be split off thermolytically, optionally in an inert solvent such as methylene chloride, chloroform, benzene, toluene, tetrahydrofuran, or dioxane and preferably in the presence of a catalytic amount of an acid such as p-toluenesulfonic acid, sulfuric acid, phosphoric acid, or polyphosphoric acid, preferably at the boiling temperature of the solvent used, for example, at temperatures of from about 40° to 100° C.

If D in a compound of Formula IV represents, for example, the benzyloxycarbonyl group, the benzyl group can also be split off hydrogenolytically in the presence of a hydrogenation catalyst such as palladium/charcoal in a suitable solvent such as methanol, ethanol, ethanol/water, glacial acetic acid, ethyl acetate, dioxane, or dimethyl formamide, preferably at temperatures of from about 0° to 50° C., for example, at room temperature, and at a hydrogen pressure of from 1 to 5 bar. During the hydrogenolysis other groups can simultaneously be reduced, for example, a halogen compound can be dehalogenated, a nitro group can be converted into the corresponding amino group, and a vinylidene group can be converted into the corresponding alkylidene group.

Method C:

A compound of the general formula

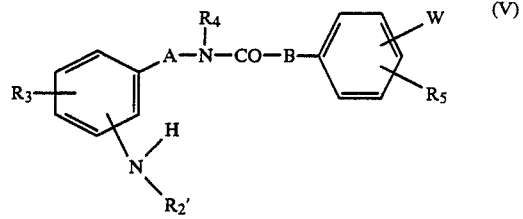 (V)

wherein $R_3$ to $R_5$, A, B, and W are as defined above and $R_2'$ represents a hydrogen atom or has the meanings mentioned before for $R_2$, the compound of Formula V optionally being formed in the reaction mixture, is reacted with a compound of the general formula

 (VI)

wherein
$R_1'$ has the meanings before for $R_1$ or together with the radical $R_2'$ of Formula V represents a straight-chained alkylene group of from 4 to 6 carbon atoms optionally substituted by one or two alkyl groups of from 1 to 3 carbon atoms or an n-pentylene group, wherein the third methylene group is replaced by an oxygen or sulfur atom, and
E represents a nucleophilic exchangable group such as a halogen atom or a sulfonyloxy group, for example, a chlorine, bromine, or iodine atom or a methanesulfonyloxy or p-toluene-sulfonyloxy group, or also a hydrogen atom if in $R_1'$ one methylene group is replaced by an aldehyde or ketone-carbonyl group, if necessary in the presence of a reducing agent, and optionally subsequent hydrolysis.

Suitable alkylation agents of Formula VI may, for example, be the corresponding halogenides or sulfates such as methyl iodide, ethyl iodide, propyl bromide, dimethyl sulfate, or diethyl sulfate.

The reaction is conveniently carried out in a solvent such as acetone, tetrahydrofuran, dimethyl formamide, dimethylsulfoxide, or hexamethyl phosphoric acid triamide, optionally in the presence of an inorganic base such as sodium carbonate, potassium carbonate, or potassium-tert.butylate or a tertiary organic base such as pyridine, at temperatures of from about 0° to 150° C., preferably, however, at temperatures of from about 20° to 75° C. If a compound of Formula V is used wherein W represents a carboxyl group, this carboxyl group can simultaneously be converted into the corresponding ester dependent upon the reaction conditions used, for example, at temperatures above room temperature and in the presence of a suitable base, for example, sodium carbonate.

The methylation can also be carried out so that a compound of Formula V is reacted with formalin in the presence of a reducing agent, for example, formic acid or hydrogen, in the presence of a hydrogenation catalyst, for example, palladium or platinum, optionally in a solvent such as formic acid or glacial acetic acid at temperatures up to the boiling temperature of the reaction mixture.

Moreover, the alkylation can also be carried out with a corresponding carbonyl compound in the presence of a hydride such as sodium cyano borohydride in a suitable solvent such as acetonitrile/glacial acetic acid or dimethyl formamide/acetic acid, preferably at a pH of 7 and at temperatures of from about 0° to 50° C.

Method D:

To prepare a compound of Formula I wherein W represents a carboxyl group, an alkanoyl group having from 1 to 3 carbon atoms, or an alkyl group having from 1 to 3 carbon atoms and with the proviso that A does not represent a vinylidene group of Formula A, a compound of the formula

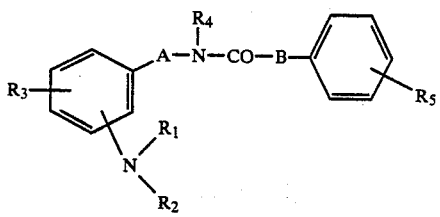

wherein $R_1$ to $R_5$, A, and B are as defined above, is reacted with phosgene, an oxalyl halogenide, an alkyl or alkanoyl halogenide with from 1 to 3 carbon atoms in the alkyl moiety, or hydrogen cyanide/hydrogen halide, preferably, however, hydrogen chloride, in the presence of a Lewis acid.

Suitable halogenides include the chlorides and bromides, and aluminium chloride is especially suitable as the Lewis acid.

The reaction is preferably carried out in a solvent such as methylene chloride, nitro benzene, chlorobenzene, dichlorobenzene, tetrachloroethane, or carbon disulfide or in polyphosphoric acid at temperatures of from about 20° to 80° C. If in a compound of Formula VIII $R_3$ represents a hydrogen atom, this can simultaneously be replaced by a corresponding alkyl or acyl radical.

Method E:

To prepare a compound of Formula I wherein W represents a carboxyl group and with the proviso that A does not represent a vinylidene group of Formula A, a compound of the formula

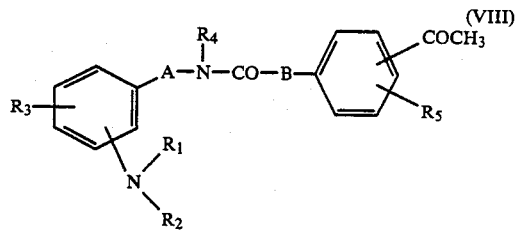

wherein $R_1$ to $R_5$, A, and B are as defined above, is reacted with a hypohalogenite optionally prepared in the reaction mixture. The reaction is conveniently carried out in a solvent such as water/tetrahydrofuran or water/dioxane and in the presence of a base such as sodium hydroxide or potassium hydroxide at temperatures of from about 0° to 80° C., preferably, however, at temperatures of from about 25° to 50° C.

Method F:

To prepare a compound of Formula I wherein W represents a carboxyl group and with the proviso that A does not represent a vinylidene group of Formula A, a compound of the formula

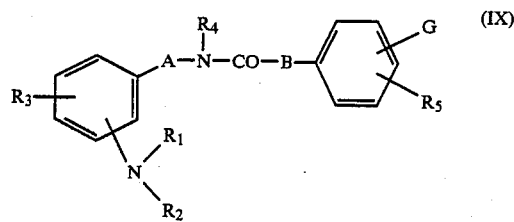

wherein $R_1$ to $R_5$, A, and B are as defined above and G represents a group being transformable by means of oxidation into a carboxyl group, is oxidized.

Such oxidizable groups include, for example, a formyl group and acetals thereof, a hydroxymethyl group and ethers thereof, an unsubstituted or substituted acyl group such as an acetyl, chloroacetyl, or propionyl group, the malonic acid-(1)-yl group, and a malonic ester-(1)-yl group.

The reaction is carried out by means of an oxidation agent in a suitable solvent such as water, glacial acetic acid, pyridine, or carbon tetrachloride at temperatures of from about 0° to 100° C., conveniently, however, at temperatures of from about 20° to 50° C. The reaction is, however, preferably carried out with silver oxide/sodium hydroxide solution, manganese dioxide/acetone or methylene chloride, hydrogen peroxide/sodium hydroxide solution, bromine or chlorine/sodium or potassium hydroxide solution, chromotrioxide/pyridine, or pyridinium chlorochromate.

Method G:

To prepare a compound of Formula I wherein $R_3$ represents a nitro group, a compound of the general formula

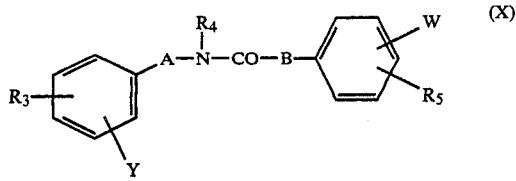

wherein $R_4$, $R_5$, A, B, and W are as defined above, $R_3$ represents a nitro group, and Y represents a nucleophilic exchangable radical such as a halogen atom, is reacted with an amine of the general formula

wherein $R_1$ and $R_2$ are as defined above, optionally followed by hydrolysis.

The meaning "a halogen atom" used in the definition of the exchangable radical Y especially represents a fluorine, chlorine, or bromine atom, preferably, however, in o- or p-position to the nitro group.

The reaction is conveniently carried out in a solvent such as water, water/methanol, water/ethanol, water/isopropanol, water/dioxane, methanol, ethanol, or dimethyl formamide or in an excess of the amine of general Formula XI used and/or of the N-formyl-derivative thereof used, optionally in the presence of an inorganic or tertiary organic base, optionally in the presence of a reaction accelerator such as copper or a copper salt, optionally in a closed vessel at temperatures of from about 20° to 150° C., preferably, however at the boiling temperature of the reaction mixture, for example, at 100° C. The reaction can, however, also be carried out in the absence of a solvent.

The optional subsequent hydrolysis is appropriately carried out in an aqueous solvent such as methanol/water, ethanol/water, or dioxane/water in the presence of an acid such as hydrochloric acid or sulfuric acid or in a base such as sodium or potassium hydroxide at temperatures of from about 50° to 100° C.

Method H:

To prepare a compound of Formula I wherein A is as defined above with the proviso that A does not represent a methylene group substituted by a cyano group, an enamide of the formula

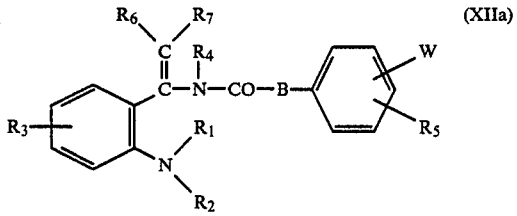

or an N-acyl-imine of the formula

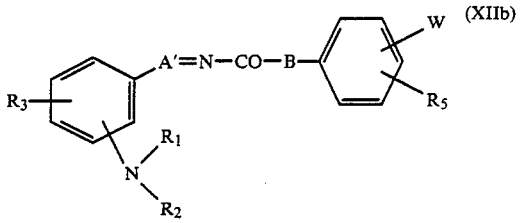

wherein $R_1$ to $R_7$, B, and W are as defined above and A' represents an optionally substituted methylene group as defined for A with the proviso that a hydrogen atom of the methylene group is part of a further bond with the attached nitrogen atom and that no cyano group is present as substituent of the methylene group,
is reduced.

The reduction is preferably carried out with hydrogen in the presence of a hydrogenation catalyst such as palladium/charcoal or platinum in a suitable solvent such as methanol, ethanol, isopropanol, ethanol/water, glacial acetic acid, ethyl acetate, dioxane, tetrahydrofuran, dimethyl formamide, benzene, or benzene/ethanol at temperatures of from about 0° to 100° C., preferably, however, at temperatures of from about 20° to 50° C., and a hydrogen pressure of from 1 to 5 bar. When a suitable chiral hydrogenation catalyst such as a transition metal $\pi$-complex, for example, a complex from $\mu,\mu'$-dichloro-bis-[1,5-cyclooctadiene-rhodium[ and (+)- or (−) O,O-isopropylidene-2,3-dihydroxy-1,4-bis-(diphenylphosphino)-butane (DIOP), is used, the hydrogenation is effected enantioselectively. Moreover, other reducible groups can be reduced during the catalytic hydrogenation; for example, a nitro group can be reduced to an amino group or a chlorine or bromine atom can be reduced to a hydrogen atom.

Method I:

To prepare a compound of Formula I wherein A represents an optionally substituted methylene or ethylene group as defined above with the proviso that A does not represent a methylene group substituted by a cyano group, a compound of the general formula

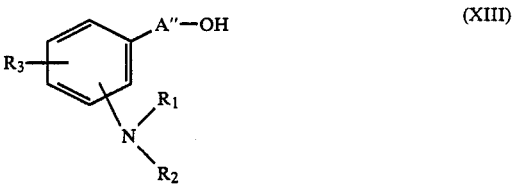

wherein $R_1$ to $R_3$ are as defined above and A" represents an optionally substituted methylene or ethylene group as defined for A with the proviso that A" does not represent a methylene group substituted by a cyano group,
is reacted with a compound of the formula

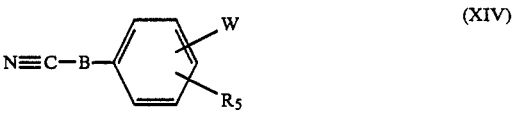

wherein $R_5$, B, and W are as defined above.

The reaction is carried out in the presence of a strong acid, which simultaneously may serve as solvent, preferably in concentrated sulfuric acid, at temperatures of from about 0° to 150° C., preferably at temperatures of from about 20° to 100° C.

If according to the invention a compound of Formula I wherein W represents a carboxyl, carboxy-alkyl, or carboxyalkenyl group and/or A represents a methylene group substituted by a carboxyl group is obtained, this compound can, if desired, be converted into a corresponding compound of Formula I by means of esterification or amidation, and/or a compound of Formula I, wherein $R_3$ and/or W represents a nitro group can be converted by means of reduction into a corresponding compound of Formula I wherein $R_3$ and/or W represent an amino group, and/or a compound of Formula I wherein $R_3$ and/or W represent an amino group can be converted via a corresponding diazonium salt into a corresponding compound of Formula I wherein $R_3$ represents a hydrogen or halogen atom or a hydroxyl, alkoxy, mercapto, alkylmercapto, chlorosulfonyl, or cyano group and/or W represents a hydrogen or halogen atom or a cyano group, whereby an optionally thus obtained compound of Formula I wherein $R_3$ represents a hydroxyl group subsequently can be converted by means of alkylation into a corresponding compound of Formula I wherein $R_3$ represents an alkoxy group, or an optionally thus obtained compound of Formula I wherein $R_3$ represents a chlorosulfonyl group can subsequently be converted by means of ammonia into a corresponding compound of Formula I wherein $R_3$ represents an aminosulfonyl group, and/or a compound of Formula I wherein $R_3$ represents an amino group or a hydroxyl group can be converted by means of acylation into a corresponding compound of Formula I, and/or a compound of Formula I wherein $R_3$ represents an amino group or a hydroxyl group can be converted by means of alkylation into a corresponding compound of Formula I, and/or a compound of Formula I wherein $R_3$ represents a halogen atom can be converted by means of dehalogenation into a corresponding compound of Formula I wherein $R_3$ represents a hydrogen atom, and/or a compound of Formula I wherein W represents an alkenyl group substituted by a carboxyl or alkoxycarbonyl group can be converted by means of hydrogenation into a corresponding compound of Formula I wherein W represents an alkyl group substituted by a carboxyl or alkoxycarbonyl group, and/or a compound of Formula I wherein $R_3$ represents a benzyloxy group and/or A represents an arylmethylene group substituted by one or two benzyloxy groups can be converted by means of debenzylation into a corresponding compound of Formula I wherein $R_3$ represents a hydroxyl group and/or A represents an arylmethylene group substituted by one or two hydroxyl groups, and/or a compound of Formula I wherein $R_3$ represents a nitrile group and/or W represents a cyano, cyano-alkyl, or cyanoalkenyl group and/or A represents a methylene group substituted by a cyano group can be converted by means of hydrolysis or alcoholysis into a corresponding compound of Formula I wherein the above-mentioned cyano group (or groups) is (are) replaced by an aminocarbonyl, carboxyl, or alkoxycarbonyl group, and/or a compound of Formula I wherein $R_3$ represents a carboxyl or alkoxycarbonyl group and/or W represents an optionally esterified carboxyl group and/or A represents a methylene group substituted by a carboxyl or alkoxycarbonyl group can be converted by means of reduction into a corresponding compound of Formula I wherein $R_3$ and/or W represents a formyl or hydroxymethyl group and/or A represents a methylene group substituted by a hydroxymethyl group, and/or a compound of Formula I wherein W represents a group of the formula $-COO-(CH_2)_n-OH$ can be converted by means of acylation into a corresponding compound of Formula I wherein W represents a group of formula $-COO-(CH_2)_n-R_8$, and/or a compound of Formula I wherein W represents a hydroxymethyl group can be converted, after conversion into a corresponding halogenmethyl compound, by means of reaction with a malonic acid diester into a corresponding compound of Formula I wherein W represents an ethyl group substituted by two alkoxycarbonyl groups, and/or a compound of Formula I wherein W represents a formyl group can be converted by means of condensation and optionally subsequent hydrolysis and/or decarboxylation into a corresponding compound of Formula I wherein W represents a vinyl group substituted by a carbonyl or alkoxycarbonyl group, and/or a compound of Formula I wherein W represents an ethyl group substituted by two alkoxycarbonyl groups can be converted by means of hydrolysis into a corresponding compound of Formula I wherein W represents an ethyl group substituted by two carboxyl groups, or by means of hydrolysis and decarboxylation into a corresponding compound of Formula I wherein W represents an ethyl group substituted by a carboxyl group, and/or a compound of Formula I wherein W represents a carboxyl group can be converted by means of conversion into a sulfonic acid hydrazide and subsequent disproportionation into a corresponding compound of Formula I wherein W represents a formyl group, and/or a compound of Formula I wherein $R_1$ and $R_2$ together with the nitrogen atom to which they are attached represent an aza-1,4-dioxa-spiro-alkyl group having from 6 to 8 carbon atoms can be converted by means of hydrolysis in the presence of an acid into a corresponding compound of Formula I wherein $R_1$ and $R_2$ together with the nitrogen atom to which they are attached represent an unbranched alkyleneimino group having from 4 to 6 carbon atoms, wherein a methylene group is replaced by a carbonyl group, and/or a compound of Formula I wherein $R_1$ and $R_2$ together with the nitrogen atom to which they are attached represent an unbranched alkyleneimino group having from 4 to 6 carbon atoms, wherein a methylene group is replaced by a carbonyl group, can be converted by means of reduction into a corresponding hydroxy-alkyleneimino compound of Formula I, and/or a compound of Formula I wherein W represents an aminocarbonyl group and/or A represents a methylene group substituted by an aminocarbonyl group can be converted by means of dehydration into a corresponding compound of general Formula I wherein W represents a cyano group and/or A represents a methylene group substituted by a cyano group.

The subsequent esterification is appropriately carried out in a suitable solvent, for example, in a corresponding alcohol, pyridine, toluene, methylene chloride, tetrahydrofuran, or dioxane, in the presence of an acid-activating and/or dehydrating agent such as thionyl chloride, ethyl chloroformate, carbonyl diimidazole, N,N'-dicyclohexylcarbodiimide, or the isourea ether thereof, optionally in the presence of a reaction accelerator such as copper chloride, or by transesterification, for example, with a corresponding carbonic acid diester, at temperatures of from about 0° to 100° C., preferably, however, at temperatures between about 20° C. and the boiling temperature of the corresponding solvent.

The subsequent amidation is appropriately carried out in a solvent such as methylene chloride, chloroform, carbon tetrachloride, ether, tetrahydrofuran, dioxane, benzene, toluene, acetonitrile, or dimethyl formamide, optionally in the presence of an acid activating agent or a dehydrating agent, for example, in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole, or triphenyl phosphine/carbon tetrachloride, or of an agent activating an amino group, for example, phosphorus trichloride, and optionally in the presence of an inorganic base such as sodium carbonate or a tertiary organic base such as triethylamine or pyridine, which simultaneously may serve as solvent, at temperatures of from about −25° C. to 250° C., preferably, however, at temperatures between about −10° and the boiling temperature of the solvent used. The reaction can also be carried out without a solvent; moreover, the water which is formed during the reaction can be separated by means of azeotropic distillation, for example, by heating with toluene in a water separator funnel or by addition of a drying agent such as magnesium sulfate or a molecular sieve.

The subsequent reduction of the nitro compound is preferably carried out in a solvent such as water, water/ethanol, methanol, glacial acetic acid, ethyl acetate, or dimethyl formamide conveniently with hydrogen in the presence of a hydrogenation catalyst such as Raney nickel, platinum, or palladium/charcoal, with metals such as iron, tin, or zinc in the presence of an acid, with metal salts such as iron (II) sulfate, tin (II) chloride, or sodium dithionite, or with hydrazine in the presence of Raney nickel at temperatures of from about 0° to 50° C., preferably, however, at room temperature.

The subsequent reaction of the diazonium salt, for example, the fluoroborate, the hydrosulfate in sulfuric acid, the hydrochloride, the hydrobromide, or the hydroiodide can be carried out in the presence of copper or a corresponding copper (I) salt such as copper (I) chloride/hydrochloric acid, copper (I) bromide/hydrobromic acid, or trisodium copper (I) tetracyanide at a pH of 7 or an alkalixanthogenat, or of copper (II) chloride/sulfur dioxide in glacial acetic acid optionally by the addition of magnesium chloride, at slightly elevated temperatures, for example, at temperatures of from about 15° to 100° C. The subsequent reaction with hypophosphorous acid is preferably carried out at from about −5° to 0° C. The hereto necessary diazonium salt is conveniently prepared in a suitable solvent, for example, in water/hydrochloric acid, methanol/hydrochloric acid, ethanol/hydrochloric acid, or dioxane/hydrochloric acid, by means of diazotization of a corresponding amino compound with a nitrite, for example, sodium nitrite, or an ester of nitrous acid, at lower temperatures, for example, at temperatures of from about −10° to 5° C.

The subsequent acylation is preferably carried out in a solvent such as methylene chloride, ether, or tetrahydrofuran, or in an excess of the acylating agent used, for example, formic acid, acetic acid, or propionic acid or their anhydrides, acid chlorides, or esters, optionally in the presence of an inorganic or tertiary organic base, which simultaneously may serve as solvent, and optionally in the presence of an acid-activating agent or of a dehydration agent at temperatures of from about −25° to 150° C., preferably, however, at temperatures between about −10° and the boiling temperature of the reaction mixture.

The subsequent N-alkylation is appropriately carried out with a corresponding halogenide or sulfonic acid ester, for example, with methyl iodide, dimethyl sulfate, ethyl bromide, or p-toluene-sulfonic acid ethyl ester, optionally in the presence of a base such as sodium hydride, potassium hydroxide, or potassium-tert.butylate and preferably in a solvent such as diethyl ether, tetrahydrofuran, dioxane, ethanol, pyridine, or dimethyl formamide at temperatures of from about 0° to 75° C., preferably, however, at room temperature. The methylation can furthermore be carried out with formaldehyde/formic acid at the boiling temperature of the reaction mixture, and the alkylation can be carried out with a corresponding carbonyl compound in the presence of a hydride such as sodium cyanoborohydride in a solvent such as acetonitrile/acetic acid or dimethyl formamide/acetic acid, preferably at a pH of 7 and at temperatures of from about 0° to 50° C.

The subsequent O-alkylation is preferably carried out with a corresponding halogenide, sulfonic acid ester, or diazoalkane, for example, with methyl iodide, dimethyl sulfate, ethyl bromide, p-toluene-sulfonic acid ethyl ester, methanesulfonic acid isopropyl ester, or diazomethane, optionally in the presence of a base such as sodium hydride, potassium hydroxide, or potassium-tert.butylate and preferably in a solvent such as diethyl ether, tetrahydrofuran, dioxane, methanol, ethanol, pyridine, or dimethyl formamide at temperatures of from about 0° to 75° C., preferably, however, at room temperature.

The subsequent dehalogenation, hydrogenation, or debenzylation is preferably carried out in a solvent such as methanol, ethanol, ethyl acetate, glacial acetic acid, or dimethyl formamide by means of catalytically activated hydrogen, for example, with hydrogen in the presence of platinum or palladium/charcoal, at temperatures of from about 0° to 75° C., preferably, however, at room temperature, and at a hydrogen pressure of from about 1 to 5 bar.

The subsequent hydrolysis is preferably carried out either in the presence of an acid such as hydrochloric acid sulfuric acid, phosphoric acid, polyphosphoric acid, or trifluoroacetic acid or in the presence of a base such as sodium hydroxide or potassium hydroxide in a suitable solvent such as water, ethanol, water/ethanol, water/isopropanol, or water/dioxane at elevated temperatures, for example, at the boiling temperature of the reaction mixture. The hydrolysis can, however, be also carried out with a nitrite, for example, sodium nitrite, in the presence of an acid such as sulfuric acid, whereby this may appropriately serve simultaneously as solvent, at temperatures of from about 0° to 50° C. The subsequent alcoholysis is appropriately carried out in the presence of a hydrogen halogenide, for example, hydrogen chloride, at temperatures between about 20° C. and the boiling temperature of the alcohol used.

The subsequent reduction is preferably carried out with a metallic hydride, for example, with a complex metallic hydride such as lithium aluminium hydride, in a suitable solvent such as diethyl ether, tetrahydrofuran, or dioxane at temperatures of from about 0° to 100° C., preferably, however, at temperatures of from about 20° to 60° C.

The subsequent conversion of a hydroxymethyl group into a halogenmethyl group is carried out with a halogenation agent such as thionyl chloride, phosphorus trichloride, phosphorus tribromide, or phosphorus pentachloride in a solvent such as methylene chloride, carbon tetrachloride, benzene, or nitro-benzene and their subsequent reaction with a malonic acid ester, for example, with an alkali metal salt of the malonic acid diethyl ester, at temperatures of from about 0° to 100° C., preferably, however, at temperatures of from about 20° to 50° C.

The subsequent condensation of a formyl compound is preferably carried out in a solvent such as pyridine or tetrahydrofuran with malonic acid, with a malonic acid ester, with a dialkylphosphonoacetic acid ester or an alkoxycarbonylmethylene-triphenyl-phosphorane, optionally in the presence of a base as condensation agent, for example, in the presence of piperidine, potassium-tert.butylate, or sodium hydride, at temperatures of from about 0° to 100° C. The desired acid is obtained by subsequent acidification, for example, with hydrochloric acid or sulfuric acid, or by subsequent alkaline hydrolysis.

The subsequent hydrolysis and decarboxylation is preferably carried out in the presence of an acid such as hydrochloric acid, sulfuric acid, phosphoric acid, polyphosphoric acid, or trifluoroacetic acid in a suitable solvent such as water, ethanol, water/ethanol, water-/isopropanol, or water/dioxane at elevated temperatures, for example, at the boiling temperature of the reaction mixture.

The subsequent disproportionation of a sulfonic acid hydrazide, which is obtained by reacting a corresponding hydrazine with a corresponding reactive carboxylic acid derivative, is carried out in the presence of a base such as sodium carbonate in a solvent such as ethylene glycol at temperatures of from about 100° to 200° C., preferably, however, at from about 160° to 170° C.

The subsequent dehydration is carried out with a dehydrating agent such as phosphorus pentoxide, sulfuric acid, or p-toluene-sulfonic acid chloride, optionally in a solvent such as methylene chloride or pyridine, at temperatures of from about 0° to 100° C., preferably, at temperatures of from about 20° to 80° C.

Moreover, the obtained compounds of Formula I containing an asymmetric carbon atom can be resolved into their enantiomers according to known methods, for example, by column chromatography on a chiral phase.

The compounds of Formula I obtained may furthermore be converted into their addition salts, especially into their pharmaceutically acceptable salts with inorganic or organic acids and also bases. Suitable acids may be, for example, hydrochloric acid, hydrobromic acid, sulfuric acid, phosphoric acid, lactic acid, citric acid, tartaric acid, succinic acid, maleic acid, or fumaric acid, and suitable bases may be, for example, sodium hydroxide, potassium hydroxide, cyclohexylamine, 2-hydroxyethyl-amine, bis(2-hydroxyethyl)-amine, or tris(2-hydroxyethyl)-amine.

The compounds of Formulas II to XIV used as starting materials are partly known from the literature, and other such compounds not previously known can be readily prepared according to known methods.

Thus, for example, a compound of Formula II wherein A represents a single bond can be obtained by reduction of a corresponding nitro compound, for example, by means of catalytically activated or nascent hydrogen or by means of sodium dithionite, or by reaction of a corresponding compound according to Hofmann, Curtius, Lossen, or Schmidt.

In an additional example, a compound of Formula II wherein A represents a vinylidene group, or the tautomeric ketimine, can be obtained by reaction of a corresponding nitrile with a corresponding Grignard or lithium compound and subsequent hydrolysis or by reaction of a corresponding ketone with a corresponding amine in the presence of titane tetrachloride. For further reaction with a compound of Formula III or reactive derivatives thereof, especially the acid chlorides, the metal organic ketimine complex can also be used.

A compound of Formula II wherein A does not represent a single bond, a vinylidene group, or a methylene group substituted by a carboxyl, alkoxycarbonyl, aminocarbonyl, or cyano group can be obtained, for example, by reduction of a corresponding nitrile with lithium aluminium hydride, by reaction of a corresponding nitrile with a corresponding Grignard or lithium compound, and optionally by subsequent lithium aluminium hydride reduction or subsequent hydrolysis to the ketimine, which subsequently is reduced with catalytically activated hydrogen, by hydrolysis or by hydrazinolysis of a corresponding phthalimido compound, by reaction of a corresponding ketone with ammonium formiate and subsequent hydrolysis or with an ammonium salt in the presence of sodium cyanoborohydride, by reduction of a corresponding oxime with lithium aluminium hydride, with catalytically activated or nascent hydrogen, by reduction of a corresponding N-benzyl or N-1-phenylethyl ketimine, for example, with catalytically activated hydrogen or with a complex metallic hydride in ether or tetrahydrofuran at temperatures between about −78° C. and the boiling temperature of the solvent used and subsequent cleavage of the benzyl or 1-phenylethyl group by means of catalytic hydrogenation, by Ritter reaction of a corresponding alcohol and potassium cyanide in sulfuric acid, or by reaction according to Hofmann, Curtius, Lossen or Schmidt of a corresponding compound. A compound of Formula II, wherein A represents a group of formula

can be obtained by reacting a corresponding aldehyde with ammonium cyanide or by reacting a corresponding cyano-hydrine with ammonia. A thus obtained amine of Formula II with the proviso that it contains an asymmetric carbon atom, can be resolved, for example, by fractionated crystallization of the diastereoisomeric salts with optically active acids and subsequent decomposition of the salts, or by column chromatography on a chiral phase, or by the formation of diastereoisomeric compounds, their separation, and subsequent cleavage into its enantiomers.

Furthermore, an optically active amine of Formula II can also be prepared by enantioselective reduction of a corresponding ketimine by means of complex boron or aluminium hydrides, in which some of the hydride hydrogen atoms are replaced by optically active alcoholate radicals, or by means of hydrogen in the presence of a suitable chiral hydrogenation catalyst, or in analogous manner starting from a corresponding N-benzyl or optionally optically active N-1-phenethyl ketimine or from a corresponding N-acyl-ketimine or enamide and optionally subsequent cleavage of the benzyl, 1-phenethyl, or acyl radical.

An optically active amine of Formula II can be furthermore obtained by diastereoselective reduction of a ketimine or hydrazone correspondingly chiral substituted at the nitrogen atom by means of a complex or non-complex boron or aluminum hydride, wherein optionally a part of the hydride atoms are replaced by corresponding alcoholate, phenolate or alkyl radicals, or by means of hydrogen in the presence of a suitable hydrogenation catalyst and subsequent optional cleavage of the chiral auxiliary radical by means of catalytic hydrogenation or hydrolysis.

An optionally active amine of Formula II can be furthermore obtained by diastereoselective addition of a corresponding metalorganic compound, preferably a Grignard or lithium compound, to a corresponding aldimine correspondingly chiral substituted at the nitrogen atom, subsequent hydrolysis, and subsequent optional cleavage of the chiral auxiliary radical by means of catalytic hydrogenation or of hydrolysis.

A compound of Formula II wherein $R_4$ represents a lower alkyl radical can be obtained by reduction of a corresponding N-acyl compound, for example, by means of lithium aluminium hydride.

The compounds of Formula IV, V, and VII to X used as starting materials can be obtained by reaction of a corresponding amine with a corresponding carboxylic acid or reactive derivatives thereof and optionally subsequent hydrolysis. A compound of Formula VIII can be obtained by Friedel-Crafts acetylation of a corresponding compound.

A compound of Formula XIIa or XIIb used as starting material can be preferably obtained by acylation of a corresponding ketimine or of a metalorganic complex thereof with a corresponding carboxylic acid or reactive derivatives thereof, optionally under tautomerization.

A compound of Formula XIII Used as starting material can be obtained by reduction of a corresponding carbonyl compound or by reaction of a corresponding carbonyl compound with a corresponding Grignard or lithium reagent and subsequent hydrolysis.

As already mentioned before, the novel compounds of Formula I exhibit valuable pharmacological properties, especially an affect on the intermediary metabolism. More particularly, the compounds of Formula I possess a bloodsugar lowering activity.

For example, the compounds

A=(Z)-4-[(1-(2-Piperidino-phenyl)-1-buten-1yl)-aminocarbonylmethyl]-benzoic acid,
B=(Z)-4-[(1-(2-Piperidino-phenyl)-1-buten-1-yl)-aminocarbonylmethyl]-benzoic acid ethyl ester,
C=(E)-4-[(1-(2-Piperidino-phenyl)-1-buten-1-yl)-aminocarbonylmethyl]-benzoic acid,
D=4-[(2-Methyl-1-(2-piperidino-phenyl)-1-propen-1-yl)-aminocarbonylmethyl]-benzoic acid,
E=(Z)-4-[(1-(2-Piperidino-phenyl)-1-hexen-1-yl)-aminocarbonylmethyl]-benzoic acid ethyl ester,
F=(Z)-4-[(3-Phenyl-1-(2-piperidino-phenyl)-1-propen-1-yl)-aminocarbonylmethyl]-benzoic acid,
G=(Z)-4-[(1-(2-(3,3-Dimethyl-piperidino)-phenyl)-1-buten-1-yl)-aminocarbonylmethyl]-benzoic acid,
H=4-[(1-(2-Pyrrolidino-phenyl)-1-butyl)-aminocarbonylmethyl]-benzoic acid,
J=(±)-4-[(1-(2-Piperidino-phenyl)-1-butyl)-aminocarbonylmethyl]-benzoic acid,
K=(+)-4-[(1-(2-Piperidino-phenyl)-1-butyl)-aminocarbonylmethyl]-benzoic acid,
L=(+)-4-[(1-(2-Piperidino-phenyl)-1-butyl)-aminocarbonylmethyl]-benzoic acid ethyl ester,
M=4-[(1-(2-Hexahydroazepino-phenyl)-1-butyl)-aminocarbonylmethyl]-benzoic acid,
N=4-[(1-(2-Piperidino-phenyl)-1-hexyl)-aminocarbonylmethyl]-benzoic acid,
O=4-[(3-Phenyl-1-(2-piperidino-phenyl)-1-propyl)-aminocarbonylmethyl]-benzoic acid,
P=4-[(2-Methoxy-1-(2-piperidino-phenyl)-1-ethyl)-aminocarbonylmethyl]-benzoic acid,
Q=4-[(α-Cyano-2-piperidino-benzyl)-aminocarbonylmethyl]-benzoic acid,
R=4-[(1-(2-Piperidino-phenyl)-1-butyl)-aminocarbonylmethyl]-benzyl alcohol,
S=4-[(1-(2-Piperidino-phenyl)-1-butyl)-aminocarbonylmethyl]-phenyl-acetic acid,
T=4=[(1-(2-Piperidino-phenyl)-1-butyl)-aminocarbonylmethyl]-cinnamic acid,
U=4-[(1-(2-Piperidino-phenyl)-1-butyl)-aminocarbonylmethyl]-benzoic acid 2,3-dihydroxy-propyl ester,
V=4-[(1-(4-Fluoro-2-piperidino-phenyl)-1-butyl)-aminocarbonylmethyl]-benzoic acid,
W=4-[(1-(4-Methoxy-2-piperidino-phenyl)-1-butyl)-aminocarbonylmethyl]-benzoic acid,
X=4-[(1-(2-Octahydroazonino-phenyl)-1-ethenyl)-aminocarbonylmethyl]-benzoic acid,
Y=4-[(1-(3-Chloro-2-piperidino-phenyl)-1-ethyl)-aminocarbonylmethyl]-benzoic acid,
Z=4-[(1-(3-Methyl-2-piperidino-phenyl)-1-ethyl)-aminocarbonylmethyl]-benzoic acid,
AA=4-[(α-(4-Methyl-phenyl)-2-piperidino-benzyl)-aminocarbonylmethyl]-benzoic acid,
AB=4-[(α-(3-Methyl-phenyl)-2-piperidino-benzyl)-aminocarbonylmethyl]-benzoic acid,
AC=4-[(α-(4-Fluoro-phenyl)-2-piperidino-benzyl)-aminocarbonylmethyl]-benzoic acid,
AD=4-[(α-(2-Fluoro-phenyl)-2-piperidino-benzyl)-aminocarbonylmethyl]-benzoic acid,
AE=4-[(α-(4-Chloro-phenyl)-2-piperidino-benzyl)-aminocarbonylmethyl]-benzoic acid,
AF=4-[(α-(3-Chloro-phenyl)-2-piperidino-benzyl)-aminocarbonylmethyl]-benzoic acid,
AG=4-[(2-Piperidino-α-(2-pyridyl)-benzyl)-aminocarbonylmethyl]-benzoic acid,
AH=4-[(2-Piperidino-α-(4-pyridyl)-benzyl)-aminocarbonylmethyl]-benzoic acid,
AJ=4-[(6-Chloro-α-phenyl-2-piperidino-benzyl)-aminocarbonylmethyl]-benzoic acid,
AK=4-[(α-Phenyl-2-piperidino-benzyl)-aminocarbonylmethyl]-cinnamic acid,
AL=3-{4-[(α-Phenyl-2-piperidino-benzyl)-aminocarbonylmethyl]-phenyl}-propionic acid,
AM=4-[(4-Chloro-α-phenyl-2-piperidino-benzyl)-aminocarbonylmethyl]-benzoic acid, AN=4-[(6-Methyl-α-phenyl-2-piperidino-benzyl)-aminocarbonylmethyl]-benzoic acid,
AO=4-[(4-Methyl-α-phenyl-2-piperidino-benzyl)-aminocarbonylmethyl]-benzoic acid,
AP=4-[(α-Phenyl-2-piperidino-benzyl)-aminocarbonylmethyl]-benzaldehyde,
AQ=4-[(2-(2-Methyl-piperidino)-α-phenyl-benzyl)-aminocarbonylmethyl]-benzoic acid,
AR=4-[(2-(3-Methyl-piperidino)-α-phenyl-benzyl)-aminocarbonylmethyl]-benzoic acid,
AS=4-[(3-Chloro-α-phenyl-2-piperidino-benzyl)-aminocarbonylmethyl]-benzoic acid,
AT=(±)-4-[(1-(2-Piperidino-phenyl)-1-ethyl)-aminocarbonylmethyl]-benzoic acid,
AU=(+)-4-[(1-(2-Piperidino-phenyl)-1-ethyl)-aminocarbonylmethyl]-benzoic acid,
AV=(±)-4-[(2-Piperidino-benzhydryl)-aminocarbonylmethyl]-benzoic acid, and
AW=(−)-4-[(2-Piperidino-benzhydryl)-aminocarbonylmethyl]-benzoic acid
were tested in the following manner:

1. Blood-sugar lowering activity

The blood-sugar lowering activity of the test compounds was determined in home-bred female rats with weights of from 180 to 220 grams. Twenty-four hours before starting the test the animals were starved. Before the test the compounds were suspended in 1.5% methyl cellulose and administered to the animals by means of an esophageal tube.

Blood was taken from the retroorbital plexus vein before administration of the test compounds as well as each of 1, 2, 3, and 4 hours after administration. Fifty microliters of each sample were deproteinized with 0.5 ml of 0.33N perchloric acid and centrifuged. The glucose content was determined in the supernatant according to the Hexokinase method by means of an analysis photometer. The statistical evaluation was performed with the t-test according to Student with $p=0.05$.

The values obtained, iin percent as compared with the controls, are set forth in the following table:

TABLE 1

| Test Compound | 5 mg/kg # | | | | 1 mg/kg # | | | |
|---|---|---|---|---|---|---|---|---|
| | 1 | 2 | 3 | 4 | 1 | 2 | 3 | 4 |
| A | | | | | −43 | −40 | −33 | −35 |
| B | −44 | −39 | −26 | −35 | −39 | −19 | −26 | −30 |
| C | | | | | −43 | −43 | −37 | −38 |
| D | | | | | −36 | −32 | −27 | −25 |
| E | −46 | −40 | −38 | −26 | −23 | −23 | −12 | −18 |
| F | −43 | −42 | −39 | −32 | | | | |
| G | | | | | −44 | −42 | −37 | −31 |
| H | −50 | −46 | −44 | −45 | | | | |
| J | −44 | −37 | −42 | −42 | −38 | −32 | −34 | −29 |
| K | | | | | −41 | −43 | −38 | −31 |
| L | −42 | −45 | −31 | −22 | −14 | −18 | −14 | n.s. |
| M | −46 | −43 | −40 | −36 | −33 | −30 | −21 | n.s. |
| N | −42 | −42 | −37 | −33 | | | | |
| O | −38* | −31* | n.s.* | n.s.* | | | | |
| P | −49 | −43 | −34 | −22 | −37 | −19 | n.s. | n.s. |
| Q | −28 | −13 | n.s. | n.s. | | | | |
| R | −38 | −40 | −35 | −29 | −39 | −34 | −29 | −24 |
| S | −49 | −42 | −30 | −17 | −29 | −20 | −10 | n.s. |
| T | −48 | −46 | −42 | −40 | −42 | −42 | −40 | −32 |
| U | −43 | −43 | −49 | −45 | −39 | −35 | −29 | −24 |
| V | −45 | −41 | −46 | −40 | −37 | −23 | −30 | −18 |
| W | −46 | −45 | −39 | −37 | −36 | −25 | −16 | n.s. |
| X | −34* | −21* | −17* | −14* | | | | |
| Y | −32 | −24 | −16 | −18 | | | | |
| Z | −22 | −33 | −28 | −26 | | | | |
| AA | −30 | −33 | −14 | n.s. | −15 | −15 | −13 | n.s. |
| AB | −43 | −38 | −36 | −27 | −26 | −15 | n.s. | n.s. |
| AC | −36 | −37 | −36 | −33 | | | | |
| AD | −28 | −32 | −27 | −28 | −16 | −20 | −17 | −14 |
| AE | −30 | −28 | −39 | −36 | −21 | −20 | −22 | n.s. |
| AF | −43 | −39 | −30 | −26 | −17 | −19 | n.s. | n.s. |
| AG | −49* | −50* | −36* | −31* | −18 | n.s. | n.s. | n.s. |
| AH | −41 | −37 | −20 | n.s. | −26 | −14 | n.s. | n.s. |
| AJ | −44 | −40 | −39 | −40 | −35 | −34 | −28 | −20 |
| AK | −48* | −47* | −40* | −45* | −32 | −19 | −10 | −17 |
| AL | −43* | −41* | −38* | −34* | −40 | −31 | −23 | −12 |
| AM | −34 | −35 | −32 | −29 | −11 | −13 | n.s. | n.s. |
| AN | −39 | −35 | −27 | −26 | −27 | −24 | n.s. | n.s. |
| AO | −37 | −34 | −32 | −31 | −21 | −17 | −15 | −11 |
| AP | | | | | −26 | −28 | −22 | −17 |
| AQ | −32 | −31 | −24 | −19 | −16 | −11 | n.s. | n.s. |
| AR | −35 | −30 | −29 | −31 | −13 | −9 | n.s. | n.s. |
| AS | −45 | −44 | −42 | −32 | −21 | −13 | n.s. | n.s. |
| AT | −45 | −45 | −36 | −32 | −34 | −26 | n.s. | −11 |
| AU | | | | | −41 | −22 | −17 | −15 |
| AV | −44 | −38 | −41 | −37 | −41 | −38 | −26 | −24 |
| AW | | | | | −40** | −34** | −31** | −26** |

Dose of test compound orally administered.
n.s. = Not statistically significant
*Dose: 10 mg/kg
**Dose: 0.6 mg/kg

2. Acute Toxicity

The acute toxicity was determined in home-bred female and male mice having body weights of from 20 to 26 gm after oral administration (suspension in a 1% methyl cellulose solution) of a single dose. Observation time: 14 days.

The following table sets forth the values obtained:

TABLE 2

| Test Compound | Peroral Toxicity |
| --- | --- |
| A | > 1000 mg/kg (0 out of 6 animals died) |
| C | > 2000 mg/kg (0 out of 6 animals died) |
| D | > 500 mg/kg (0 out of 6 animals died) |
| J | > 2000 mg/kg (0 out of 10 animals died) |
| AA | > 1000 mg/kg (0 out of 10 animals died) |
| AB | > 1000 mg/kg (0 out of 10 animals died) |
| AC | > 1000 mg/kg (0 out of 10 animals died) |
| AD | > 1000 mg/kg (0 out of 10 animals died) |
| AE | > 1000 mg/kg (0 out of 10 animals died) |
| AG | > 1000 mg/kg (0 out of 10 animals died) |
| AT | > 2000 mg/kg (1 out of 10 animals died) |
| AV | > 2000 mg/kg (0 out of 10 animals died) |

Based on their pharmacological properties, the compounds of general Formula I prepared according to the invention and their pharmaceutically acceptable salts are suitable for the treatment of diabetes mellitus. They can be incorporated, optionally in combination with other active ingredients, into the usual pharmaceutical preparations such as tablets, coated tablets, capsules, powders, or suspensions. The single dose for adults is from about 1 to 50 mg (from about 0.014 to 0.7 mg/kg), preferably, however, from about 2.5 to 20 mg (from about 0.036 to 0.29 mg/kg), 1 or 2 times daily. Dependent upon the type and body weight of the patient to be treated, upon the type and severity of the disease, upon the type of preparation, and upon the route of administration as well as upon the period or interval over which the administration takes place, it may, however, be necessary to deviate from the above dosages. Thus, it may be sufficient in some cases to administer more or less than the above-mentioned amounts of active ingredient. The optimum dosage and route of administration of the active ingredients which are necessary in each case can easily be determined by one skilled in the art.

The following examples are intended to illustrate the invention and should not be construed as limiting the invention thereto.

EXAMPLES

Example 1

4-[(1-(5-Chloro-2-dimethylamino-phenyl)-1-ethyl)-aminocarbonylmethyl]-benzoic acid methyl ester An amount of 1.67 gm (0.0103 mol) of carbonyl diimidazole was added with stirring at 20° C. to a solution of 2.00 gm (0.0103 mol) of 4-methoxycarbonyl-phenyl acetic acid in 13.5 ml of absolute tetrahydrofuran. Subsequently the mixture was heated to reflux temperature for 45 minutes in the absence of moisture. After cooling to room temperature, 2.05 gm (0.0103 mol of 1-(5-chloro-2-dimethylaminophenyl)-ethylamine in 7 ml of absolute tetrahydrofuran were added, and the reaction mixture was stirred overnight at 20° C. After evaporation in vacuo the evaporation residue was purified by column chromatography on silica gel (toluene/acetone=10:1).

Yield: 2.6 gm (66.7% of theory),

M.p.: 153°–155° C. (from ether)

| | | | | | | | | |
| --- | --- | --- | --- | --- | --- | --- | --- | --- |
| Calc.: | C | 64.08 | H | 6.18 | Cl | 9.46 | N | 7.47 |
| Found: | | 64.30 | | 6.04 | | 9.70 | | 7.39 |

By use of procedures analogous to that of Example 1 the following compounds were prepared:

(a)

4-[(1-(5-Chloro-2-dipropylamino-phenyl)-1-ethyl)-aminocarbonylmethyl]-benzoic acid methyl ester Yield: 42% of theory, M.p.: 135°–137° C. (from ether/petroleum ether)

| | | | | | | | | |
| --- | --- | --- | --- | --- | --- | --- | --- | --- |
| Calc.: | C | 66.83 | H | 7.25 | Cl | 8.23 | N | 6.50 |
| Found: | | 66.95 | | 7.35 | | 8.35 | | 6.05 |

(b)

4-[1-(5-Chloro-2-dibutylamino-phenyl)-1-ethyl-amicarbonylmethyl]-benzoic acid methyl ester Yield: 64.8% of theory, M.p.: 110°–112° C.

| | | | | | | | | |
| --- | --- | --- | --- | --- | --- | --- | --- | --- |
| Calc.: | C | 68.03 | H | 7.69 | Cl | 7.72 | N | 6.10 |
| Found: | | 67.86 | | 7.61 | | 7.73 | | 6.17 |

(c)

4-[(1-(5-Chloro-2-N-cyclohexyl-N-methylamino-phenyl)-1-ethyl)-aminocarbonylmethyl]-benzoic acid methyl ester Yield: 63.9% of theory, M.p.: 152°–153° C. (ether)

| | | | | | | | | |
| --- | --- | --- | --- | --- | --- | --- | --- | --- |
| Calc.: | C | 67.78 | H | 7.05 | Cl | 8.00 | N | 6.32 |
| Found: | | 67.70 | | 6.92 | | 8.24 | | 6.46 |

(d)

4-[(5-Chloro-2-pyrrolidino-benzyl)-aminocarbonylmethyl-benzoic acid methyl ester Yield: 68.1% of theory, M.p.: 139°–141° C. (methanol)

| | | | | | | | | |
| --- | --- | --- | --- | --- | --- | --- | --- | --- |
| Calc.: | C | 65.19 | H | 5.99 | Cl | 9.17 | N | 7.24 |
| Found: | | 65.46 | | 5.91 | | 9.26 | | 7.41 |

(e)

4-[(1-(5-Chloro-2-pyrrolidino-phenyl)-1-ethyl)-aminocarbonylmethyl]-benzoic acid methyl ester Yield: 58.3% of theory, M.p.: 133°–135° C. (methanol)

| | | | | | | | | |
| --- | --- | --- | --- | --- | --- | --- | --- | --- |
| Calc. | C | 65.91 | H | 6.29 | Cl | 8.84 | N | 6.99 |
| Found: | | 66.24 | | 6.19 | | 8.75 | | 7.13 |

(f)

4-[(5-Chloro-2-piperidino-benzyl)-aminocarbonylmethyl]-benzoic acid methyl ester Yield: 75.1% theory, M.p.: 123°–125° C. (ether)

| Calc. | C | 65.91 | H | 6.29 | Cl | 8.84 | N | 6.99 |
|---|---|---|---|---|---|---|---|---|
| Found: | | 66.05 | | 6.13 | | 8.86 | | 7.21 |

(g)
4-[(1-(5-Chloro-2-piperidino-benzyl)-aminocarbonyl)-1-ethyl]-benzoic acid methyl ester Yield: 70.4% of theory,
M.p.: 142°–144° C. (ether)

| Calc.: | C | 66.57 | H | 6.56 | Cl | 8.55 | N | 6.75 |
|---|---|---|---|---|---|---|---|---|
| Found: | | 66.50 | | 6.49 | | 8.44 | | 6.86 |

(h)
4-[(1-(5-Chloro-2-piperidino-phenyl)-1-ethyl)-aminocarbonylmethyl]-benzoic acid methyl ester Yield: 69.5% of theory,
M.p.: 147°–149° C. (ether)

| Calc.: | C | 66.57 | H | 6.56 | Cl | 8.55 | N | 6.75 |
|---|---|---|---|---|---|---|---|---|
| Found: | | 66.33 | | 6.54 | | 8.67 | | 6.85 |

(i)
4-[(1-(5-Chloro-2-(3-methyl-piperidino)-phenyl)-1-ethyl)-aminocarbonylmethyl]-benzoic acid methyl ester Yield: 54.3% of theory,
M.p.: 160°–162° C. (methanol)

| Calc.: | C | 67.20 | N | 6.81 | Cl | 8.27 | N | 6.53 |
|---|---|---|---|---|---|---|---|---|
| Found: | | 67.27 | | 6.81 | | 8.13 | | 6.45 |

(j)
4-[(1-(5-Chloro-2-(3,5-cis-dimethyl-piperidino)-phenyl)-1-ethyl)-aminocarbonylmethyl]-benzoic acid methyl ester Yield: 44% of theory,
M.p. 190°–193° C. (methanol)

| Calc.: | C | 67.78 | H | 7.05 | Cl | 8.00 | N | 6.32 |
|---|---|---|---|---|---|---|---|---|
| Found: | | 67.50 | | 7.05 | | 8.25 | | 6.48 |

(k)
4-[(1-(5-Chloro-2-piperidino-phenyl)-1-propyl)-aminocarbonylmethyl]-benzoic acid methyl ester Yield: 65.9% of theory,
M.p.: 142°–144° C. (ether)

| Calc. | C | 67.20 | H | 6.81 | Cl | 8.26 | N | 6.53 |
|---|---|---|---|---|---|---|---|---|
| Found: | | 67.45 | | 6.63 | | 8.38 | | 6.63 |

(l)
4-[(1-(5-Chloro-2-piperidino-phenyl)-2-methyl-1-propyl)-aminocarbonylmethyl]-benzoic acid methyl ester Yield: 61.4% of theory,
M.p.: 156°–158° C. (ether)

| Calc.: | C | 67.78 | H | 7.05 | Cl | 8.00 | N | 6.32 |
|---|---|---|---|---|---|---|---|---|
| Found: | | 67.80 | | 7.17 | | 7.89 | | 6.28 |

(m)
4-[(1-(5-Chloro-2-morpholino-phenyl)-1-ethyl)-aminocarbonylmethyl]-benzoic acid methyl ester Yield: 69.8% of theory,
M.p.: 156°–158° C. (ether)

| Calc.: | C | 63.38 | H | 6.04 | Cl | 8.50 | N | 6.72 |
|---|---|---|---|---|---|---|---|---|
| Found: | | 63.24 | | 6.12 | | 8.70 | | 6.85 |

(n)
4-[(1-(5-Chloro-2-thiomorpholino-phenyl)-1-ethyl-aminocarbonylmethyl]-benzoic acid methyl ester Yield: 68.2% of theory,
M.p.: 167°–169° C. (ether)

| Calc.: | C | 61.03 | H | 5.82 | Cl | 8.19 | N | 6.47 | S | 7.41 |
|---|---|---|---|---|---|---|---|---|---|---|
| Found | | 60.83 | | 5.77 | | 8.33 | | 6.49 | | 7.39 |

(o)
4-[(1-(5-Chloro-2-(hexahydro-1H-azepino)-phenyl)-1-ethyl-aminocarbonylmethyl]-benzoic acid methyl ester Yield: 41.7% of theory,
M.p.: 146°–147° C. (methylene chloride/petroleum ether)

| Calc.: | C | 67.19 | H | 6.81 | Cl | 8.27 | N | 6.53 |
|---|---|---|---|---|---|---|---|---|
| Found: | | 66.90 | | 6.66 | | 8.30 | | 6.39 |

(p)
4-[(1-(5-Chloro-2-octahydroazocino-phenyl)-1-ethyl)-aminocarbonylmethyl-benzoic acid methyl ester Yield: 30% of theory,
M.p.: 154°–156° C.

| Calc.: | mol peak m/e = 442/444 (1 chlorine) |
|---|---|
| Found: | m/e = 442/444 (1 chlorine) |

(q)
4-[(1-(5-Chloro-2-(octahydro-1H-azonino)-phenyl-1-ethyl)-aminocarbonylmethyl]-benzoic acid methyl ester Yield: 38% of theory,
M.p.: 184°–185° C. (chloroform/toluene)

| Calc.: | C | 68.32 | H | 7.28 | N | 6.13 |
|---|---|---|---|---|---|---|
| Found: | | 68.10 | | 7.30 | | 6.28 |

(r)
4-[(2-(5-Chloro-2-piperidino-phenyl)-2-propyl)-aminocarbonylmethyl]-benzoic acid methyl ester Yield: 84.4% of theory,
M.p.: 162°–164° C.

| Calc.: | mol peak m/e = 428/430 (1 chlorine) |
| Found: | m/e = 428/430 (1 chlorine) |

(s)
4-[(1-(5-Nitro-2-piperidino-phenyl)-1-ethyl)-aminocarbonylmethyl]-benzoic acid methyl ester Yield: 68.3% of theory,
M.p.: 178°-180° C. (toluene)

| Calc.: | C | 64.93 | H | 6.40 | N | 9.88 |
| Found: | | 65.05 | | 6.43 | | 9.87 |

(t)
4-[(1-(2-Piperidino-phenyl)-1-ethyl)-aminocarbonylmethyl]-benzoic acid methyl ester Yield: 59.1% of theory,
M.p.: 145°-147° C.

| Calc.: | C | 72.61 | H | 7.42 | N | 7.36 |
| Found: | | 72.35 | | 7.39 | | 7.40 |

(u)
4-[(5-Methyl-2-piperidino-benzyl)-aminocarbonylmethyl]-benzoic acid methyl ester Yield: 32.9% of theory,
M.p.: 124°-126° C. (pertoleum ether/acetone)

| Calc.: | mol peak m/e = 380 |
| Found: | m/e = 380 |

(v)
N-(4-Nitro-phenacetyl)-N-[1-(2-piperidino-phenyl)-ethyl]-amine

Yeild: 62.4% of theory,
M.p.: 165°-167° C. (ether)

| Calc.: | C | 68.64 | H | 6.86 | N | 11.44 |
| Found: | | 68.73 | | 6.88 | | 11.63 |

(w)
N-(4-Acetyl-phenacetyl)-N-[1-(2-piperidino-phenyl)-ethyl]-amine

Yield: 32.4% of theory,
M.p.: 162°-164° C. (ether)

| Calc.: | C | 75.79 | H | 7.74 | N | 7.69 |
| Found: | | 75.51 | | 7.86 | | 7.38 |

(x)
N-(4-Acetyl-phenacetyl)-N-[1-(5-chloro-2-piperidino-phenyl)-ethyl]-amine Yield: 50.3% of theory,
M.p.: 162°-164° C. (ether)

| Calc.: | C | 69.24 | H | 6.82 | N | 7.02 |

| Found: | 68.88 | 6.63 | 6.70 |

(y)
2-[(1-(2-Piperidino-phenyl)-1-ethyl)-aminocarbonylmethyl]-benzoic acid methyl ester Yield: 82% of theory,
M.p.: 107°-108° C.

| Calc.: | C | 72.60 | H | 7.42 | N | 7.36 |
| Found: | | 72.79 | | 7.38 | | 7.53 |

(z)
3-[(1-(2-Piperidino-phenyl)-1-ethyl)-aminocarbonylmethyl]-benzoic acid ethyl ester Yield: 47% of theory,
M.p.: 155° C.

| Calc.: | C | 73.07 | H | 7.67 | N | 7.10 |
| Found: | | 73.30 | | 7.58 | | 7.17 |

(aa)
3-Chloro-4-[(1-(2-piperidino-phenyl)-1-ethyl)-aminocarbonylmethyl]-benzoic acid ethyl ester Yield: 63% of theory,
M.p.: 123°-124° C.

| Calc.: | C | 67.20 | H | 6.81 | Cl | 8.27 | N | 6.53 |
| Found: | | 67.28 | | 6.84 | | 8.36 | | 6.50 |

(bb)
4-[(1-(2-(1,2,3,4-Tetrahydro-isoquinoline-2-yl)-phenyl)-1-ethyl)-aminocarbonylmethyl]-benzoic acid ethyl ester Yield: 43% of theory,
M.p.: 142°-144° C.

| Calc.: | C | 75.99 | H | 6.83 | N | 6.33 |
| Found: | | 75.64 | | 6.75 | | 6.35 |

(cc)
4-[(1-(2-Piperidino-phenyl)-1-ethyl)-aminocarbonylmethyl]-toluene

Yield: 59% of theory,
M.p.: 136°-138° C.

| Calc.: | C | 78.53 | H | 8.39 | N | 8.33 |
| Found: | | 78.58 | | 8.16 | | 8.26 |

(dd)
4-[(5-Chloro-2-piperidino-anilino)-carbonylmethyl]-benzoic acid methyl ester Yield: 40.3% of theory,
M.p.: 156°-158° C. (methanol/toluene)

| Calc.: | C | 65.19 | H | 5.99 | Cl | 9.16 |

| Found: | 65.20 | 6.15 | 9.40 |
|---|---|---|---|

(ee) 4-[2-(Piperidino-anilino-carbonyl)-1-ethyl]-benzoic acid methyl ester

Yield: 26.9% of theory,
M.p.: 71°–73° C. (petroleum ether)

| Calc.: | C | 72.10 | H | 7.15 | N | 7.65 |
|---|---|---|---|---|---|---|
| Found: | | 72.00 | | 7.09 | | 7.94 |

(ff) 4-[(1-(2-(1,2,3,6-Tetrahydro-pyridino)-phenyl)-1-ethyl)-aminocarbonylmethyl]-benzoic acid ethyl ester Yield: 63.4% of theory,
M.p.: 125°–127° C. (ether)

| Calc.: | C | 73.44 | H | 7.19 | N | 7.14 |
|---|---|---|---|---|---|---|
| Found: | | 73.38 | | 7.13 | | 7.13 |

(gg) 4-[(2-(5-Chloro-2-piperidino-phenyl)-1-ethyl)-aminocarbonylmethyl]-benzoic acid ethyl ester ield: 68% of theory,
M.p.: 95°–97° C. (ethanol)

| Calc.: | C | 67.20 | H | 6.81 | Cl | 8.27 | N | 6.53 |
|---|---|---|---|---|---|---|---|---|
| Found: | | 67.75 | | 6.76 | | 8.22 | | 6.24 |

(hh) 4-[(1-(5-Fluoro-2-piperidino-phenyl)-1-ethyl)-aminocarbonylmethyl]-benzoic acid ethyl ester Yield: 47.3% of theory,
M.p.: 138°–140° C. (ether)

| Calc.: | C | 69.88 | H | 7.99 | N | 6.79 |
|---|---|---|---|---|---|---|
| Found: | | 70.10 | | 7.10 | | 6.87 |

(ii) 4-[(1-(5-Nitro-2-piperidino-phenyl)-1-ethyl)-aminocarbonylmethyl]-benzoic acid ethyl ester
Yield: 56.5% of theory,
M.p.: 144°–147° C. (ethanol)

| Calc.: | C | 65.59 | H | 6.65 | N | 9.56 |
|---|---|---|---|---|---|---|
| Found: | | 65.78 | | 6.56 | | 9.73 |

(jj) 4-[(2-(1-(2-Piperidino-phenyl)-1-ethyl)-aminocarbonylethyl]-benzoic acid methyl ester
Yield: 90% of theory,
M.p.: 129°–131° C.

| Calc.: | C | 73.06 | H | 7.67 | N | 7.10 |
|---|---|---|---|---|---|---|
| Found: | | 72.61 | | 7.77 | | 7.52 |

(kk) 4-[(2-Hydroxy-1-(2-piperidino-phenyl)-1-ethyl)-aminocarbonylmethyl]-benzoic acid ethyl ester
Yield: 44.4% of theory,
M.p.: 132°–135° C. (petroleum ether/acetone)

| Calc.: | C | 70.22 | H | 7.37 | N | 6.82 | m/e = 410 |
|---|---|---|---|---|---|---|---|
| Found: | | 70.02 | | 7.25 | | 6.77 | m/e = 410 |

(ll) 4-[(1-(5-Hydroxy-2-piperidino-phenyl)-1-ethyl)-aminocarbonylmethyl]-benzoic acid ethyl ester
Yield: 64.2% of theory,
M.p.: 150°–151° C. (ether)

| Calc.: | C | 70.22 | H | 7.37 | N | 6.82 | m/e = 410 |
|---|---|---|---|---|---|---|---|
| Found: | | 70.37 | | 7.17 | | 6.82 | m/e = 410 |

(mm) 4-[(α-Methoxycarbonyl-2-piperidino-benzyl)-aminocarbonylmethyl]-benzoic acid ethyl ester
Yield: 59% of theory,
M.p.: 110°–112° C. (petroleum ether/acetone)

| Calc.: | C | 68.47 | H | 6.90 | N | 6.39 | m/e = 438 |
|---|---|---|---|---|---|---|---|
| Found: | | 68.57 | | 6.64 | | 6.46 | m/e = 438 |

(nn) 4-[(1-(5-Chloro-2-(2-methyl-piperidino)-phenyl)-1-ethyl)-aminocarbonylmethyl]-benzoic acid ethyl ester
Yield: 71.3% of theory,
M.p.: <20° C.

| Calc.: | m/e = 442/444 (1 chlorine) |
|---|---|
| Found: | m/e = 442/444 (1 chlorine) |

(oo) 4-[(1-(2-Hexahydroazapino-phenyl)-1-ethyl)-aminocarbonylmethyl]-benzoic acid ethyl ester
Yield: 68% of theory,
M.p.: 145°–148° C. (toluene)

| Calc.: | C | 73.50 | H | 7.90 | N | 6.86 |
|---|---|---|---|---|---|---|
| Found: | | 73.35 | | 8.04 | | 6.89 |

(pp) 4-[(1-(2-(1,4-Dioxa-8-azaspiro[4,5]decyl-(8))-phenyl)-1-ethyl)-aminocarbonylmethyl]-benzoic acid ethyl ester
Yield: 64.3% of theory,
M.p.: 143–145° C. (petroleum ether/acetone)

| Calc.: | C | 69.01 | H | 7.13 | N | 6.19 |
|---|---|---|---|---|---|---|
| Found: | | 69.30 | | 7.38 | | 6.21 |

(qq) 4-[(1-(2-(2-Methyl-pyrrolidino)-phenyl)-1-ethyl)-aminocarbonylmethyl]-benzoic acid ethyl ester
Yield: 72% of theory,
M.p.: 94°–97° C.

| Calc.: | C | 73.07 | H | 7.66 | N | 7.10 |
|---|---|---|---|---|---|---|
| Found: | | 72.25 | | 7.67 | | 7.11 |

(rr) 4-[(1-(3-Methyl-2-piperidino-phenyl)-1-ethyl)-aminocarbonylmethyl]-benzoic acid ethyl ester
Yield: 39.5% of theory,
M.p.: 178°–179° C.

| Calc.: | m/e = 408 |
|---|---|

-continued

| | |
|---|---|
| Found: | m/e = 408 |

(ss)  4-[(1-(3-Chloro-2-piperidino-phenyl)-1-ethyl)-aminocarbonylmethyl]-benzoic acid ethyl ester
Yield: 52.6% of theory,

| | | |
|---|---|---|
| Calc.: | m/e = | 428/430 (1 chlorine) |
| Found: | m/e = | 428/430 (1 chlorine) |

Example 2

(+)
4-[(1-(2-Piperidino-phenyl)-1-ethyl)-aminocarbonylmethyl]-benzoic acid ethyl ester A quantity of 231.4 mg (1.43 m mol) of carbonyl diimidazole was added to a solution of 290.9 mg (1.40 m mol) of 4-ethoxycarbonyl-phenyl acetic acid in 6 ml of tetrahydrofuran. Subsequently the mixture was heated to reflux temperature for 1.5 hours in the absence of moisture. After cooling to room temperature, 0.385 ml (≐2.78 m mol) of triethylamine (dried over potassium hydroxide) and 360 mg (1.30 m mol) of (+) 1-(2-piperidino-phenyl)-ethyl-amine dihydrochloride [m.p. 242° C. (decomp.); $[\alpha]_D^{20}$ = +14.8° (c=1; methanol)] together with 2 ml of tetrahydrofuran were added, and the mixture was sitrred for four hours in a 50° C. warm oil bath. After evaporation in vacuo the evaporation residue was distributed between chloroform and water. The chloroform extract was dried over sodium sulfate, filtered through a G3-glass frit, and evaporated in vacuo to dryness. The residue obtained was purified by column chromatography on silica gel (chloroform/methanol=6:1).

Yield: 229 mg (44.7% of theory),
M.p.: 89°–90° C. (ether)
$[\alpha]_D^{20}$=8.2° (c=1; methanol)

| | | | | | | | | |
|---|---|---|---|---|---|---|---|---|
| Calc.: | C | 73.07 | H | 7.66 | N | 7.10 | m/e = | 394 |
| Found: | | 73.20 | | 7.68 | | 7.14 | m/e = | 394 |

By use of a procedure analogous to that of Example 2, the following was prepared:

(−)4-[(1-(2-Piperidino-phenyl)-1-ethyl)-aminocarbonylmethyl]-benzoic acid ethyl ester Prepared from (−) 1-(2-piperidino-phenyl)-ethylamino-dihydrochloride [m.p.: 239°–242° C. (decomp.); $[\alpha]_D^{20}$: −19.6° (c=1; methanol)].

Yield: 41.1% of theory),
M.p.: 77°–79° C. (ether/cyclohexane)
$[\alpha]_D^{20}$= −6.2° (c=1; methanol)

| | | | | | | | | |
|---|---|---|---|---|---|---|---|---|
| Calc.: | C | 73.07 | H | 7.66 | N | 7.10 | m/e = | 394 |
| Found: | | 72.67 | | 7.75 | | 6.82 | m/e = | 394 |

Example 3

4-[(1-(4-Chloro-2-piperidino-phenyl)-1-ethyl)-aminocarbonylmethyl]-benzoic acid ethyl ester An amount of 2.3 ml (0.023 mol) of carbon tetrachloride was added to a solution of 5.5 gm (0.032 mol) of 1-(4-chloro-2-piperidino-phenyl)-ethylamine, 4.8 gm (0.032 mol) of 4-ethoxycarbonyl-phenyl acetic acid, 7.3 gm (0.028 mol) of triphenyl phosphine, and 3.2 ml (0.023 mol) of triethylamine in 50 ml of acetonitrile, and the mixture was stirred for 24 hours at room temperature. After evaporation in vacuo the evaporation residue was distributed between 100 ml of water and ethyl acetate. The combined organic extracts, which were dried over sodium sulfate, were filtered and evaporated in vacuo, and the evaporation residue was purified by column chromatography on silica gel (toluene/ethyl acetate=4:1).

Yield: 6.1 gm (62% of theory),
M.p.: 126°–128° C.

| | | | | | | | | |
|---|---|---|---|---|---|---|---|---|
| Calc.: | C | 67.20 | H | 6.81 | Cl | 8.27 | N | 6.53 |
| Found: | | 67.43 | | 6.97 | | 8.16 | | 6.40 |

By use of procedures analogous to that of Example 3, the following compounds were prepared:

(a)  4-[(1-(4-Methyl-2-piperidino-phenyl)-1-ethyl)-aminocarbonylmethyl]-benzoic acid ethyl ester
Yield: 48.2% of theory,
M.p.: 120°–122° C. (ether)

| | | | | | | |
|---|---|---|---|---|---|---|
| Calc.: | C | 73.50 | H | 7.89 | N | 6.86 |
| Found: | | 73.61 | | 7.95 | | 6.73 |

(b)  4-[(1-(2-(4-Methyl-piperidino)-phenyl)-1-ethyl)-aminocarbonylmethyl]-benzoic acid ethyl ester
Yield: 55.8% of theory,
M.p.: 125°–128° C. (ether)

| | | | | | | |
|---|---|---|---|---|---|---|
| Calc.: | C | 73.50 | H | 7.90 | N | 6.86 |
| Found: | | 73.30 | | 7.99 | | 7.20 |

(c)  4-[(1-(2-Piperidino-phenyl)-1-ethyl)-aminocarbonylmethyl]-benzoic acid ethyl ester
Yield: 71% of theory,
M.p.: 147°–148° C.

| | | | | | | |
|---|---|---|---|---|---|---|
| Calc.: | C | 73.06 | H | 7.67 | N | 7.10 |
| Found: | | 73.54 | | 8.04 | | 6.95 |

(d) 4-[(1-(2-Piperidino-phenyl)-1-ethyl)-aminocarbonylmethyl]-phenyl acetic acid
Prepared from 1-(2-piperidino-phenyl)-ethylamine and p-phenylene diacetic acid.
Yield: 27% of theory,
M.p.: 186°–189° C.

| | | | | | | |
|---|---|---|---|---|---|---|
| Calc.: | C | 72.60 | H | 7.42 | N | 7.36 |
| Found: | | 72.75 | | 7.65 | | 7.11 |

(e)  4-[(2-Piperidino-benzhydryl)-aminocarbonylmethyl]-benzoic acid ethyl ester
Yield: 87.4% of theory,
M.p.: 160°–162° C.

| | | | | | | |
|---|---|---|---|---|---|---|
| Calc.: | C | 76.29 | H | 7.06 | N | 6.14 |
| Found: | | 76.44 | | 7.08 | | 6.17 |

(f)  4-[(5-Chloro-2-piperidino-benzhydryl)-aminocarbonylmethyl]-benzoic acid ethyl ester
Yield: 78% of theory, M.p.: 202°–204° C.

| Calc.: | C | 70.93 | H | 6.36 | Cl | 7.22 | N | 5.71 |
|---|---|---|---|---|---|---|---|---|
| Found: | | 70.85 | | 6.40 | | 7.11 | | 5.45 |

(g) 4-[(1-(4-Piperidino-phenyl)-1-ethyl)-aminocarbonylmethyl]-benzoic acid ethyl ester
Yield: 39% of theory,
M.p.: 118°–120° C.

| Calc.: | C | 73.07 | H | 7.67 | N | 7.10 |
|---|---|---|---|---|---|---|
| Found: | | 73.20 | | 7.78 | | 7.11 |

(h) 4-[(1-(2-(4-Methyl-piperazino)-phenyl)-1-ethyl)-aminocarbonylmethyl]-benzoic acid ethyl ester
Yield: 53% of theory,
M.p.: 130°–132° C.

| Calc.: | C | 70.38 | H | 7.63 | N | 10.26 |
|---|---|---|---|---|---|---|
| Found: | | 70.41 | | 7.53 | | 10.13 |

(i) 4-[(1-(2-(4-Benzyl-piperazino)-phenyl)-1-ethyl)-aminocarbonylmethyl]-benzoic acid ethyl ester
Yield: 75% of theory,
M.p.: 135°–136° C.

| Calc.: | C | 74.20 | H | 7.26 | N | 8.66 |
|---|---|---|---|---|---|---|
| Found: | | 74.45 | | 7.34 | | 8.54 |

(j) 4-[(1-(2-(4-p-chlorophenyl-piperiazino)-phenyl)-1-ethyl)-aminocarbonylmethyl]-benzoic acid ethyl ester
Yield: 48.5% of theory,
M.p.: 178°–180° C.

| Calc.: | C | 68.83 | H | 6.37 | N | 8.30 | Cl | 7.01 |
|---|---|---|---|---|---|---|---|---|
| Found: | | 68.71 | | 6.22 | | 8.41 | | 6.82 |

(k) 4-[(α-Cyclohexyl-2-piperidino-benzy)-aminocarbonylmethyl]-benzoic acid ethyl ester
Yield: 75% of theory,
M.p.: 135° C.

| Calc.: | C | 75.29 | H | 8.28 | N | 6.06 |
|---|---|---|---|---|---|---|
| Found: | | 75.11 | | 8.13 | | 5.99 |

(l) N-(4-Chloro-phenacetyl)-N-[1-(2-piperidino-phenyl)-ethyl]-amine
Yield: 79% of theory,
M.p.: 150°–152° C.

| Calc.: | C | 70.67 | N | 7.06 | Cl | 9.93 | N | 7.85 |
|---|---|---|---|---|---|---|---|---|
| Found: | | 70.95 | | 7.84 | | 10.09 | | 7.90 |

(m) 4-[(2-Pyrrolidino-benzhydryl)-aminocarbonylmethyl]-benzoic acid ethyl ester
Yield: 57% of theory,
M.p.: 168°–165° C.

| Calc.: | C | 75.99 | H | 6.83 | N | 6.33 |
|---|---|---|---|---|---|---|
| Found: | | 75.45 | | 7.52 | | 6.10 |

(n) 4-[(2-Hexamethyleneimino-benzhydryl)-aminocarbonylmethyl]-benzoic acid ethyl ester
Yield: 68% of theory,
M.p.: 151°–154° C.

| Calc.: | C | 76.56 | H | 7.28 | N | 5.95 |
|---|---|---|---|---|---|---|
| Found: | | 76.43 | | 7.19 | | 6.01 |

(o) (−)-4-[(2-Piperidino-benzhydryl)-aminocarbonylmethyl]-benzoic acid ethyl ester
Prepared from (−)-α-phenyl-2-piperidino-benzylamine [[α]$_D^{20}$=−62.9° (c=1, methanol); ee=99.4 (HPLC, after reaction with (−)-1-phenylethylisocyanate)] and 4-ethoxycarbonylphenyl acetic acid.
Yield: 71.8% of theory,
M.p.: 164°–165° C.

| Calc.: | C | 76.29 | H | 7.06 | N | 6.14 |
|---|---|---|---|---|---|---|
| Found: | | 76.35 | | 7.10 | | 6.05 |

[α]$_D^{20}$=−2.9° (c=1, methanol)

(p) (+)-4-[(2-Piperidino-benzhydryl)-aminocarbonylmethyl]-benzoic acid ethyl ester
Prepared from (+)-α-phenyl-2-piperidino-benzylamine [[α]$_D^{20}$=55.2° (c=1, methanol); ee=96.6 (HPLC, after reaction with (−)-1-phenylethylisocyanate)] and 4-ethoxycarbonylphenyl acetic acid.
Yield: 71% of theory,
M.p.: 161°–162° C.

| Calc.: | C | 76.29 | H | 7.06 | N | 6.14 |
|---|---|---|---|---|---|---|
| Found: | | 76.41 | | 7.15 | | 6.10 |

[α]$_D^{20}$=+2.6° (c=1, methanol)

Example 4

4-[(1-(2-Piperidino-phenyl)-1-ethenyl-aminocarbonylmethyl]-benzoic acid ethyl ester Seventeen grams (0.0647 mol) of triphenyl phosphine, 11.2 gm (0.0539 mol) of 4-ethoxycarbonylphenylacetic acid, 22.6 ml (0.162 mol) of triethylamine, and 5.2 ml (0.0539 mol) of carbon tetrachloride were successively added under stirring to a solution of 10.9 gm (0.0539 mol) of freshly prepared (2-piperidinophenyl)-methyl-ketimine in 100 ml of acetonitrile. The solution, which was clear after a short time, was stirred for 20 hours at 20° C. The resultant precipitate (triethylamine hydrochloride) was filtered off, and the filtrate was evaporated in vacuo. The evaporation residue was purified by column chromatography on silica gel (toluene/acetone=10:1).
Yield: 15 gm (70.1% of theory
M.p.: 112°–115° C. (ether)

| Calc.: | C | 73.44 | H | 7.19 | N | 7.14 |
|---|---|---|---|---|---|---|
| Found: | | 73.28 | | 7.32 | | 6.96 |

By use of procedures analogous to that of Example 4, the following compounds were prepared:

(a) 4-[(α-Cyclohexylidene-2-piperidino-benzyl)-aminocarbonylmethyl]-benzoic acid ethyl ester
Yield: 24% of theory,
M.p.: 131°–133° C.

| Calc.: | C | 75.62 | H | 7.88 | N | 6.08 |
|---|---|---|---|---|---|---|
| Found: | | 75.59 | | 7.47 | | 6.01 |

(b) 4-[1-(2-Piperidino-phenyl)-1-propenyl)-aminocarbonylmethyl]-benzoic acid ethyl ester
Yield: 65.0% of theory (E- and Z-isomeric mixture)
M.p.: of the polar isomer: 82–84° C. (Z-form)

| Calc.: | C | 73.86 | H | 7.44 | N | 6.89 |
|---|---|---|---|---|---|---|
| Found: | | 73.73 | | 7.57 | | 7.01 |

Example 5

4-[(1-(2-Piperidino-phenyl)-1-ethyl)-aminocarbonylmethyl]-benzoic acid ethyl ester A solution of 60.6 gm (0.267 mol) of 4-ethoxycarbonyl phenacetyl chloride in 120 ml of methylene chloride was added dropwise with slight ice cooling to a stirred solution of 49.6 gm (0.243 mol) of 1-(2-piperidino-phenyl)-ethylamine [b.p. 0.6: 100°–107° C.; m.p. of the dihydrochloride: 234°–237° C. (decomp.)] and 37.3 ml (0.267 mol) of triethylamine in 245 ml of methylene chloride at an internal temperature of 20°–30° C. After stirring for two hours at room temperature, the resultant precipitate was filtered off and washed one time with methylene chloride, and the combined methylene chloride phases were extracted successively twice with water, once with 10% aqueous ammonia, twice with water, once with 100 ml of 3% hydrochloric acid, and twice with water. The methylene chloride phase was dried over sodium sulfate and evaporated in vacuo. The evaporation residue was crystallized from ether.
Yield: 88.8 gm (92.7% of theory),
M.p.: 148°–150° C.

By use of procedures analogous to that of Example 5, the following compounds were prepared:

(a) 4-[5-Methyl-2-piperidino-benzyl)-aminocarbonylmethyl]-benzoic acid ethyl ester
Yield: 22.5% of theory,
M.p.: 116.5°–117° C. (ethanol/petroleum ether)

| Calc.: | C | 73.07 | H | 7.66 | N | 7.10 |
|---|---|---|---|---|---|---|
| Found: | | 73.48 | | 7.62 | | 7.15 |

(b) 4-[(1-(5-Methyl-2-piperidino-phenyl)-1-ethyl)-aminocarbonylmethyl]-benzoic acid ethyl ester
Yield: 20.2% of theory,
M.p.: 132°–132.5° C. (ethanol)

| Calc.: | C | 73.50 | H | 7.90 | N | 6.86 |
|---|---|---|---|---|---|---|
| Found: | | 73.49 | | 7.74 | | 6.94 |

(c) 4-[(1-(5-Methoxy-2-piperidino-phenyl)-1-ethyl)-aminocarbonylmethyl]-benzoic acid ethyl ester
Yield: 35.8% of theory,
M.p.: 131°–132° C. (ethanol)

| Calc.: | C | 70.73 | H | 7.60 | N | 6.60 |
|---|---|---|---|---|---|---|
| Found: | | 70.98 | | 7.59 | | 6.38 |

(d) 4-[(1-(2-Piperidino-phenyl)-1-ethyl)-N-methylaminocarbonylmethyl]-benzoic acid ethyl ester
Yield: 65.2% of theory,
M.p.: <20° C.

| Calc.: | C | 73.50 | H | 7.90 | N | 6.86 |
|---|---|---|---|---|---|---|
| Found: | | 72.99 | | 7.60 | | 6.87 |

(e) 4-[(1-(2-Decahydro-isoquinoline-2-yl)-phenyl)-1-ethyl)-aminocarbonylmethyl]-benzoic acid ethyl ester
Yield: 44% of theory,
M.p.: 159° C.

| Calc.: | C | 74.96 | H | 8.08 | N | 6.24 |
|---|---|---|---|---|---|---|
| Found: | | 75.09 | | 8.01 | | 6.01 |

(f) 4-[(1-(2-(1,2,3,4,5,6,7,8-Octahydro-isoquinoline-2-yl)-phenyl)-1-ethyl)-aminocarbonylmethyl]-benzoic acid ethyl ester
Yield: 35% of theory,
M.p.: 115°–117° C.

| Calc.: | C | 75.30 | H | 7.67 | N | 6.27 |
|---|---|---|---|---|---|---|
| Found: | | 75.18 | | 7.37 | | 5.89 |

(g) 4-[(1-(2-Octahydro-isoindole-2-yl)-phenyl)-1-ethyl)-aminocarbonylmethyl]-benzoic acid ethyl ester
Yield: 36% of theory,
M.p.: 141° C.

| Calc.: | C | 74.62 | H | 7.88 | N | 6.44 |
|---|---|---|---|---|---|---|
| Found: | | 74.70 | | 7.97 | | 6.42 |

(h) 4-[(1-(3-Piperidino-phenyl)-1-ethyl)-aminocarbonylmethyl]-benzoic acid ethyl ester
Yield: 24% of theory,
M.p.: 164° C.

| Calc.: | C | 73.07 | H | 7.66 | N | 7.10 |
|---|---|---|---|---|---|---|
| Found: | | 72.80 | | 7.48 | | 7.13 |

(i) 4-[(1-(6-Chloro-2-piperidino-phenyl)-1-ethyl)-aminocarbonylmethyl]-benzoic acid ethyl ester
Yield: 17% of theory,
M.p.: <20° C.

| Calc.: | C | 67.20 | H | 6.81 | Cl | 8.26 | N | 6.53 | m/e 428/30 |
|---|---|---|---|---|---|---|---|---|---|
| Found: | | 67.96 | | 6.56 | | 8.80 | | 6.67 | m/e 428/30 |

(j) 4-[(1-(6-Methyl-2-piperidino-phenyl)-1-ethyl)-aminocarbonylmethyl]-benzoic acid ethyl ester
Yield: 3.5% of theory,
M.p.: <20° C.

| Calc.: | C | 73.49 | H | 4.89 | N | 6.85 | m/e = 408 |
|---|---|---|---|---|---|---|---|

-continued

| Found: | 73.80 | 7.61 | 7.01 | m/e = 408 |

(k) 4-[(1-(2-(3-Aza-bicyclo[3.2.2]nonane-3-yl)-phenyl)-1-ethyl)-aminocarbonylmethyl]-benzoic acid ethyl ester
Yield: 0.5% of theory,
M.p.: <20° C.

| Calc.: | m/e 434 |
| Found: | m/e 434 |

(l) N-[1-(5-Chloro-2-piperidino-phenyl)-ethyl]-N-phenacetylamine
Yield: 53.5% of theory,
M.p.: 134°–136° C. (ethanol)

| Calc.: | C | 70.67 | H | 7.06 | Cl | 9.94 | N | 7.85 |
| Found: | | 70.40 | | 7.32 | | 9.77 | | 7.68 |

Example 6

4-[(1-(2-Piperidino-phenyl)-1-ethenyl)-aminocarbonylmethyl]-benzoic acid ethyl ester A solution of 2.49 gm (0.011 mol) of 4-ethoxycarbonylphenacetyl chloride in 10 ml of methylene chloride was added dropwise with ice cooling within 15 minutes to a stirred solution of 2.02 gm (0.010 mol) of freshly prepared methyl-(2-piperidino-phenyl)-ketimine and 1.53 ml of (0.011 mol) of triethylamine in 10 ml of methylene chloride at an internal temperature of 1° to 6° C. The reaction mixture was stirred for 20 minutes at 20° C. and poured into cold sodium bicarbonate solution. After extraction several times the organic extract was washed once with water, dried over sodium sulfate, filtered, and evaporated in vacuo. The evaporation residue was purified by column chromatography on silica gel (toluene/acetone=50:1).
Yield: 1.86 gm (47.7% of theory),
M.p.: 113°–116° (ethanol)

| Calc.: | C | 73.44 | H | 7.19 | N | 7.14 | m/e 392 |
| Found: | | 72.95 | | 6.98 | | 7.22 | m/e 392 |

By use of procedures analogous to that of Example 6, the following compounds were prepared:
(a) 4-[(1-(6-Chloro-2-piperidino-phenyl)-1-ethenyl)-aminocarbonylmethyl]-benzoic acid ethyl ester
Yield: 37% of theory,
M.p.: 102°–105° C.

| Calc.: | C | 67.51 | H | 6.37 | Cl | 8.30 | N | 6.56 | m/e 426/28 |
| Found: | | 67.86 | | 6.39 | | 8.58 | | 6.23 | m/e 426/28 |

(b) 4-[(1-(6-Methyl-2-piperidino-phenyl)-1-ethenyl)-aminocarbonylmethyl]-benzoic acid ethyl ester
Yield: 41% of theory,
M.p.: 116°–118° C.

| Calc.: | C | 73.86 | H | 7.43 | N | 6.89 |
| Found: | | 73.75 | | 7.43 | | 6.77 |

Example 7

4-[(1-(2-Piperidino-phenyl)-1-ethenyl)-aminocarbonylmethyl-benzoic acid ethyl ester A solution of 1.55 gm (6.86 m mol) of 4-ethoxycarbonylphenacetyl chloride in 5 ml of methylene chloride was added dropwise under stirring to a suspension of 2.20 gm (6.24 m mol) of magnesium iodide-[methyl-(2-piperidino-phenyl)-ketimino]-complex in 15 ml of methylene chloride, whereby the internal temperature rose from 20° to 30° C. After stirring for two hours at room temperature, the reaction mixture was mixed with water under stirring and extracted several times with methylene chloride. The methylene chloride solution was washed thrice with water, dried over sodium sulfate, filtered, and evaporated in vacuo. The evaporation residue was purified by column chromatography on silica gel (toluene/acetone=50:2).
Yield: 1.1 gm (45.8% of theory),
M.p.: 115°–118° C. (ethanol)

| Calc.: | C | 73.44 | H | 7.19 | N | 7.14 |
| Found: | | 73.30 | | 7.06 | | 7.16 |

By use of a procedure analogous to that of Example 7, the following compound was prepared:
4-[(1-(5-Chloro-2-piperidino-phenyl)-1-ethenyl)-aminocarbonylmethyl]-benzoic acid ethyl ester
Yield: 39.5% of theory,
M.p.: 142°–145° C. (ethanol)

| Calc.: | C | 67.51 | H | 6.37 | Cl | 8.30 | N | 6.56 |
| Found: | | 67.51 | | 6.37 | | 8.36 | | 6.59 |

Example 8

4-[(1-(5-Chloro-2-dimethylamino-phenyl)-1-ethyl)-aminocarbonylmethyl]-benzoic acid A solution of 2.0 gm (0.00534 mol) of 4-[(1-(5-chloro-2-dimethylamino-phenyl)-ethyl)-aminocarbonylmethyl]-benzoic acid-methyl ester and 0.32 gm (0.00801 mol) of sodium hydroxide in 23 ml of ethanol and 7 ml of water was stirred for two hours at 50° C. After evaporation in vacuo, water was added, and the reaction mixture was adjusted to pH 6 by means of 2N hydrochloric acid and extracted with ethyl acetate. The organic phase was extracted with water, dried over sodium sulfate, filtered, and evaporated in vacuo. The evaporation residue was recrystallized from ether.
Yield: 1.7 gm (88% of theory),
M.p.: 190°–192° C.

| Calc.: | C | 63.24 | H | 5.87 | Cl | 9.83 | N | 7.76 |
| Found: | | 62.90 | | 5.81 | | 10.02 | | 7.90 |

By a procedure analogous to that of Example 8, the following compounds were prepared:
(a) 4-[(1-(5-Chloro-2-dipropylamino-phenyl)-1-ethyl)-aminocarbonylmethyl]-benzoic acid
Yield: 87.6% of theory,
M.p.: 203°–205° C.

| Calc.: | C | 66.25 | H | 7.01 | Cl | 8.50 | N | 6.72 |

Found: 65.97 6.96 8.52 6.55

(b) 4-[(1-(5-Chloro-2-dibutylamino-phenyl)-1-ethyl)-aminocarbonylmethyl]-benzoic acid
Yield: 77.3% of theory,
M.p.: 200°–202° C.

| Calc.: | C | 67.47 | H | 7.48 | Cl | 7.97 | N | 6.30 |
|---|---|---|---|---|---|---|---|---|
| Found: | | 67.45 | | 7.60 | | 8.28 | | 6.44 |

(c) 4-[(1-(5-Chloro-2-N-cyclohexyl-N-methylamino-phenyl)-1-ethyl)-aminocarbonylmethyl]-benzoic acid
Yield: 88.2% of theory,
M.p.: 198°–200° C. (ether)

| Calc.: | C | 67.20 | H | 6.81 | Cl | 8.27 | N | 6.53 |
|---|---|---|---|---|---|---|---|---|
| Found: | | 67.10 | | 6.73 | | 8.16 | | 6.47 |

(d) 4-[(5-Chloro-2-pyrrolidino-benzyl)-amninocarbonylmethyl]-benzoic acid
Yield: 84.2% of theory,
M.p.: 208°–210° C. (ethyl acetate)

| Calc.: | C | 64.42 | H | 5.68 | Cl | 9.51 | N | 7.51 |
|---|---|---|---|---|---|---|---|---|
| Found: | | 64.70 | | 5.68 | | 9.58 | | 7.60 |

(e) 4-[(1-(5-Chloro-2-pyrrolidino-phenyl)-1-ethyl)-aminocarbonylmethyl]-benzoic acid
Yield: 81.1% of theory,
M.p.: 202°–204° C. (ethyl acetate)

| Calc.: | C | 65.20 | H | 5.99 | Cl | 9.17 | N | 7.24 |
|---|---|---|---|---|---|---|---|---|
| Found: | | 65.02 | | 6.12 | | 9.32 | | 7.10 |

(f) 4-[(5-Chloro-2-piperidino-benzyl)-aminocarbonylmethyl]-benzoic acid
Yield: 78% of theory,
M.p.: 164°–166° C.

| Calc.: | C | 65.19 | H | 5.99 | Cl | 9.17 | N | 7.24 |
|---|---|---|---|---|---|---|---|---|
| Found: | | 65.50 | | 5.76 | | 9.24 | | 7.36 |

(g) 4-[(1-(5-Chloro-2-piperidino-benzyl)-aminocarbonyl)-1-ethyl]-benzoic acid
Yield: 81.1% of theory,
M.p.: 213°–216° C. (acetone/ether)

| Calc.: | C | 65.90 | H | 6.29 | Cl | 8.84 | N | 6.99 |
|---|---|---|---|---|---|---|---|---|
| Found: | | 66.30 | | 6.40 | | 9.00 | | 7.05 |

(h) 4-[(1-(5-Chloro-2-piperidino-phenyl)-1-ethyl)-aminocarbonylmethyl]-benzoic acid
Yield: 84.9% of theory,
M.p.: 213°–215° C. (ether)

| Calc.: | C | 65.91 | H | 6.29 | Cl | 8.85 | N | 6.99 |
|---|---|---|---|---|---|---|---|---|
| Found: | | 66.18 | | 6.19 | | 8.88 | | 7.12 |

(i) 4-[(1-(5-Chloro-2-(3-methyl-piperidino)-phenyl)-1-ethyl)-aminocarbonylmethyl]-benzoic acid
Yield: 69.2% of theory,
M.p. 208°–210° C. (ethyl acetate)

| Calc.: | C | 66.57 | H | 6.56 | Cl | 8.55 | N | 6.75 |
|---|---|---|---|---|---|---|---|---|
| Found: | | 66.36 | | 6.77 | | 8.58 | | 6.80 |

(j) 4-[(1-(5-Chloro-2-(3,5-cis-dimethyl-piperidino)-phenyl-1-ethyl)-aminocarbonylmethyl]-benzoic acid
Yield: 82.2% of theory,
M.p.: 212°–214° C. (ether)

| Calc.: | C | 67.20 | H | 6.81 | Cl | 8.26 | N | 6.53 |
|---|---|---|---|---|---|---|---|---|
| Found: | | 66.95 | | 6.69 | | 8.43 | | 6.68 |

(k) 4-[(1-(5-Chloro-2-piperidino-phenyl)-1-propyl)-aminocarbonylmethyl]-benzoic acid
Yield: 81.5% of theory,
M.p.: 200°–203° C. (ether)

| Calc.: | C | 66.57 | H | 6.56 | Cl | 8.55 | N | 6.75 |
|---|---|---|---|---|---|---|---|---|
| Found: | | 66.74 | | 6.35 | | 8.59 | | 6.45 |

(l) 4-[(1-(5-Chloro-2-piperidino-phenyl)-2-methyl-1-propyl)-aminocarbonylmethyl]-benzoic acid
Yield: 82.7% of theory,
M.p.: 236°–240° C. (ethyl acetate)

| Calc.: | C | 67.20 | H | 6.81 | Cl | 8.27 | N | 6.53 |
|---|---|---|---|---|---|---|---|---|
| Found: | | 67.19 | | 6.56 | | 8.14 | | 6.39 |

(m) 4-[(1-(5-Chloro-2-morpholino-phenyl)-1-ethyl)-aminocarbonylmethyl]-benzoic acid
Yield: 85.6% of theory,
M.p.: 201°–203° C. (ether)

| Calc.: | C | 62.60 | H | 5.75 | Cl | 8.80 | N | 6.95 |
|---|---|---|---|---|---|---|---|---|
| Found: | | 62.30 | | 5.82 | | 8.83 | | 6.85 |

(n) 4-[(1-(5-Chloro-2-thiomorpholino-phenyl)-1-ethyl)-aminocarbonylmethyl]-benzoic acid
Yield: 87.6% of theory,
M.p.: 216°–217° C. (ether)

| Calc.: | C | 60.20 | H | 5.53 | Cl | 8.46 | N. | 6.69 |
|---|---|---|---|---|---|---|---|---|
| Found: | | 59.90 | | 5.51 | | 8.61 | | 6.53 |

(o) 4-[(1-(5-Chloro-2-hexahydro-1H-azepino)-phenyl)-1-ethyl)-aminocarbonylmethyl]-benzoic acid
Yield: 81.2% of theory,
M.p.: 202°–204° C. (chloroform/toluene)

| Calc.: | C | 66.58 | H | 6.56 | Cl | 8.55 | N | 6.75 |
|---|---|---|---|---|---|---|---|---|
| Found: | | 66.60 | | 6.37 | | 8.50 | | 6.59 |

(p) 4-[(1-(5-Chloro-2-octahydroazocino-phenyl)-1-ethyl)-aminocarbonylmethyl]-benzoic acid
Yield: 44.4% of theory,
M.p.: 196°–197° C. (chloroform/petroleum ether)

| Calc.: | C | 67.19 | H | 6.81 | N | 6.53 |
|---|---|---|---|---|---|---|
| Found: | | 67.10 | | 6.97 | | 6.37 |

(q) 4-[(1-(5-Chloro-2-(octahydro-1H-azonino)-phenyl)-1-ethyl)-aminocarbonylmethyl]-benzoic acid
Yield: 74.7% of theory,
M.p.: 204°–206° C. (ethyl acetate/petroleum ether)

| Calc.: | C | 67.78 | H | 7.05 | N | 6.32 |
|---|---|---|---|---|---|---|
| Found: | | 67.50 | | 7.03 | | 6.04 |

(r) 4-[(2-(5-Chloro-2-piperidino-phenyl)-2-propyl)-aminocarbonylmethyl]-benzoic acid
Yield: 82.9% of theory,
M.p.: 227°–229° C. (acetone)

| Calc.: | C | 66.57 | H | 6.56 | Cl | 8.55 | N | 6.75 |
|---|---|---|---|---|---|---|---|---|
| Found: | | 66.03 | | 6.66 | | 8.67 | | 6.59 |

(s) 4-[(1-(5-Nitro-2-piperidino-phenyl)-1-ethyl)-aminocarbonylmethyl]-benzoic acid
Yield: 95.6% of theory,
M.p.: 252°–254° C. (ether)

| Calc.: | C | 64.22 | H | 6.12 | N | 10.21 |
|---|---|---|---|---|---|---|
| Found: | | 64.20 | | 6.17 | | 10.12 |

(t) 4-[(1-(2-Piperidino-phenyl)-1-ethyl)-aminocarbonylmethyl]-benzoic acid
Yield: 85% of theory,
M.p.: 170°–172° C.

| Calc.: | C | 72.11 | H | 7.15 | N | 7.64 |
|---|---|---|---|---|---|---|
| Found: | | 71.94 | | 7.03 | | 7.72 |

(u) 4-[(2-(2-Piperidino-phenyl)-2-propyl)-aminocarbonylmethyl]-benzoic acid
Yield: 72.7% of theory,
M.p.: 213°–215° C.

| Calc.: | C | 72.61 | H | 7.42 | N | 7.36 |
|---|---|---|---|---|---|---|
| Found: | | 72.52 | | 7.31 | | 7.45 |

(v) 4-[(5-Methyl-2-piperidino-benzyl)-aminocarbonylmethyl]-benzoic acid
Yield: 64.6% of theory,
M.p.: 120°–122° C.

| Calc.: | C | 72.11 | H | 7.15 | N | 7.64 | m/e | 366 |
|---|---|---|---|---|---|---|---|---|
| Found: | | 72.42 | | 7.38 | | 7.54 | m/e | 366 |

M.p.: of the hydrochloride: 266° C. (decomp).

| Calc.: | C | 65.58 | H | 6.76 | Cl | 8.80 | N | 6.95 |
|---|---|---|---|---|---|---|---|---|
| Found: | | 65.00 | | 6.62 | | 9.40 | | 7.00 |

(w) 4-[(2-Piperidino-anilino)-carbonylmethyl]-benzoic acid×0.25HCl
Yield: 72.5% of theory,
M.p.: 216°–217° C.

| Calc.: | (×0.25 HCl) | C | 69.11 | H | 6.45 | Cl | 2.55 | N | 8.06 |
|---|---|---|---|---|---|---|---|---|---|
| Found: | | | 69.40 | | 6.32 | | 3.08 | | 8.37 |

(x) 4-[(5-Chloro-2-piperidino-anilino)-carbonylmethyl]-benzoic acid hydrochloride
Yield: 51.3% of theory,
M.p.: 232° C. (decomp.)

| Calc.: | C | 58.68 | N | 5.42 | Cl | 17.32 | N | 6.84 |
|---|---|---|---|---|---|---|---|---|
| Found | | 58.26 | | 5.44 | | 17.97 | | 6.74 |

(y) 4-[2-(2-Piperidino-anilino-carbonyl)-1-ethyl]-benzoic acid-semihydrate
Yield: 69.9% of theory,
M.p.: 151°–153° C. (petroleum ether/acetone)

| Calc.: | (×0.5 H₂O) | C | 69.78 | H | 6.97 | N | 7.75 |
|---|---|---|---|---|---|---|---|
| Found | | | 69.30 | | 6.82 | | 7.46 |

(z) 4-[(2-(1-(2-Piperidino-phenyl)-1-ethyl)-aminocarbonyl)-ethyl]-benzoic acid×0.2H₂O
Yield: 71.4% of theory,
M.p.: 171°–172° C. (acetone/petroleum ether)

| Calc.: | (×0.2 H₂O) | C | 71.91. | H | 7.45 | N | 7.29 |
|---|---|---|---|---|---|---|---|
| Found: | | | 71.90 | | 7.30 | | 7.03 |

Example 9

4-[(1-(5-Benzyloxy-2-piperidino-phenyl)-1-ethyl)-aminocarbonylmethyl]-benzoic acid Two hundred forty-four milligrams (0.487 m mol) of 4-[(1-5-benzyloxy-2-piperidino-phenyl)-ethyl)-aminocarbonylmethyl]benzoic acid ethyl ester in 2.5 ml of ethanol were heated under stirring with 0,73 ml of 1N sodium hydroxide solution in a bath of 50° C., until (after 3 hours) no ester could be detected in the thin layer chromatogram. After addition of 0.73 ml of 1N hydrochloric acid, the reaction mixture was evaporated in vacuo and distributed between ethyl acetate and water. The organic extract was dried over sodium sulfate filtered, and evaporated in vacuo. The evaporation residue was recrystallized from methanol.
Yield: 191 mg (83% of theory),
M.p.: 220°–222° C.

| Calc.: | C | 73.71 | H | 6.83 | N | 5.93 |
|---|---|---|---|---|---|---|
| Found: | | 73.21 | | 6.67 | | 5.80 |

By use of a procedure analogous to that of Example 9, the following compounds were prepared:
(a) 4-[(1-(2-Hexahydroazepino-phenyl)-1-ethyl)-aminocarbonylmethyl]-benzoic acid
Yield: 68.2% of theory,
M.p.: 174°–176° C. (ethyl acetate)

| Calc.: | C | 72.61 | H | 7.42 | N | 7.36 |
|---|---|---|---|---|---|---|
| Found: | | 72.36 | | 7.34 | | 7.38 |

(b) 4-[(1-(2-(1,2,3,6-Tetrahydro-pyridino)-phenyl)-1-ethyl)-aminocarbonylmethyl]-benzoic acid
Yield: 68.2% of theory,
M.p.: 158°–160° C. (ethyl acetate)

| Calc.: | C | 72.51 | H | 6.64 | N | 7.69 |
|---|---|---|---|---|---|---|

(c)  4-[(2-(5-Chloro-2-piperidino-phenyl)-1-ethyl)-aminocarbonylmethyl]-benzoic acid
Yield; 75% of theory,
M.p.: 192°–195° C. (ethyl acetate)

| Calc.: | C | 65.91 | H | 6.29 | Cl | 8.84 | N | 6.99 |
|---|---|---|---|---|---|---|---|---|
| Found: | | 66.39 | | 6.17 | | 8.45 | | 6.78 |

(d)  4-[(1-(5-Fluoro-2-piperidino-phenyl)-1-ethyl)-aminocarbonylmethyl]-benzoic acid
Yield: 52.9% of theory
M.p.: 174°–176° C. (ethyl acetate)

| Calc.: | C | 68.75 | H | 6.55 | N | 7.29 |
|---|---|---|---|---|---|---|
| Found: | | 68.30 | | 6.48 | | 7.45 |

(e)  4-[(5-Methyl-2-piperidino-benzyl)-aminocarbonylmethyl]-benzoic acid
Yield: 53.9% of theory,
M.p.: 120°–122° C. (ethanol)

| Calc.: | C | 72.11 | H | 7.15 | H | 7.64 | m/e = 366 |
|---|---|---|---|---|---|---|---|
| Found: | | 72.45 | | 7.04 | | 7.64 | m/e = 366 |

(f)  4-[(1-(5-Cyano-2-piperidino-phenyl)-1-ethyl)-aminocarbonylmethyl]-benzoic acid
Yield: 71.6% of theory,
M.p.: 198°–200° C. (ether)

| Calc.: | C | 70.57 | H | 6.44 | N | 10.73 |
|---|---|---|---|---|---|---|
| Found: | | | | 6.38 | | 11.00 |

(g)  4-[(1-(5-Carboxy-2-piperidino-phenyl)-1-ethyl)-aminocarbonylmethyl]-benzoic acid
Prepared from the corresponding diethyl ester by saponification with 2.5 equivalents of sodium hydroxide.
Yield: 83.5% of theory,
M.p.: 260° (decomp.)

| Calc.: | C | 67.30 | H | 6.38 | N | 6.82 |
|---|---|---|---|---|---|---|
| Found: | | 67.76 | | 6.62 | | 6.85 |

(h)  4-[(1-(2-(1,4-Dioxa-8-azaspiro[4,5]decane-8-yl)-phenyl)-1-ethyl)-aminocarbonylmethyl]-benzoic acid semihydrate
Yield: 85.7% of theory,
M.p.: 130°–135° C. (petroleum ether/acetone)

| Calc.: | (× 0.5 H₂O) | C | 66.49 | H | 6.74 | N | 6.46 |
|---|---|---|---|---|---|---|---|
| Found: | | | 66.56 | | 6.65 | | 6.46 |

(i)  4-[2-Hydroxy-1-(2-piperidino-phenyl)-1-ethyl)-aminocarbonylmethyl]-benzoic acid
Yield: 65% of theory,
M.p.; 155°–157° (decomp.; petroleum ether/acetone)

| Calc.: | m/e = 382 |
|---|---|
| Found: | m/e = 382 |

(j)  4-[(1-(5-Chloro-2-(2-methyl-piperidino)-phenyl)-1-ethyl)-aminocarbonylmethyl]-benzoic acid
Yield: 64.1% of theory,
M.p.: 195°–198° C. (ethyl acetate)

| Calc.: | C | 66.57 | H | 6.56 | Cl | 8.54 | N | 6.75 |
|---|---|---|---|---|---|---|---|---|
| Found: | | 66.01 | | 6.25 | | 8.32 | | 6.90 |

(k)  4-[(1-(5-Aminocarbonyl-2-piperidino-phenyl)-1-ethyl)-aminocarbonylmethyl]-benzoic acid
Yield: 86% of theory,
M.p.: 231°–235° C. (ethyl acetate)

| Calc.: | C | 67.45 | H | 6.65 | N | 10.26 |
|---|---|---|---|---|---|---|
| Found: | | 67.96 | | 6.68 | | 10.11 |

(l)  4-[(1-(2-(4-Methyl-piperidino)-phenyl)-1-ethyl)-aminocarbonylmethyl]-benzoic acid
Yield: 67.7% of theory,
M.p.: 173°–175° C. (chloroform)

| Calc.: | C | 72.61 | H | 7.42 | N | 7.36 |
|---|---|---|---|---|---|---|
| Found: | | 72.20 | | 7.36 | | 7.45 |

(m)  4-[(1-(2-Piperidino-phenyl)-1-ethyl)-N-methylaminocarbonylmethyl]-benzoic acid hydrochloride
Conversion of the viscous betain (75% crude) into the hydrochloride by means of hydrochloric acid in isopropanolic solution.
Yield: 32% of theory,
M.p.: 222°–230° C. (decomp.) (ethanol)

| Calc.: | C | 66.25 | H | 7.01 | Cl | 8.50 | N | 6.71 |
|---|---|---|---|---|---|---|---|---|
| Found: | | 66.07 | | 6.37 | | 8.37 | | 6.58 |

(n)  2-[(1-(2-Piperidino-phenyl)-1-ethyl)-aminocarbonylmethyl]-benzoic acid
Yield: 7% of theory,
M.p.: 135° C. (decomp.)

| Calc.: | C | 72.10 | H | 7.15 | N | 7.64 |
|---|---|---|---|---|---|---|
| Found: | | 72.29 | | 7.03 | | 7.37 |

(o)  3-[(1-(2-Piperidino-phenyl)-1-ethyl)-aminocarbonylmethyl]-benzoic acid
Yield: 86% of theory,
M.p.: 205°–207° C.

| Calc.: | C | 72.11 | H | 7.15 | N | 7.64 |
|---|---|---|---|---|---|---|
| Found: | | 72.30 | | 7.29 | | 7.71 |

(p)  3-Chloro-4-[(1-(2-piperidino-phenyl)-1-ethyl)-aminocarbonylmethyl]-benzoic acid
Yield: 38% of theory,
M.p.: from 175° C. sintering, from 190° C. clear melt

| Calc.: | C | 65.91 | H | 6.29 | Cl | 8.84 | N | 6.99 |
|---|---|---|---|---|---|---|---|---|
| Found: | | 65.42 | | 6.32 | | 9.05 | | 6.77 |

(q) 4-[(1-(2-(1,2,3,4-Tetrahydro-isoquinoline-2-yl)-phenyl)-1-ethyl)-aminocarbonylmethyl]-benzoic acid
Yield: 59% of theory,
M.p.: 207°–209° C.

| Calc.: | C | 75.34 | H | 6.32 | N | 6.76 |
|---|---|---|---|---|---|---|
| Found: | | 75.30 | | 6.29 | | 6.67 |

(r) 4-[(1-(3-Piperidino-phenyl)-1-ethyl)-aminocarbonylmethyl]-benzoic acid
Yield: 33% of theory,
M.p.: 206°–208° C.

| Calc.: | C | 72.09 | H | 7.15 | N | 7.64 |
|---|---|---|---|---|---|---|
| Found: | | 72.04 | | 7.14 | | 7.57 |

(s) 4-[(1-(6-Chloro-2-piperidino-phenyl)-1-ethyl)-aminocarbonylmethyl]-benzoic acid
Yield: 35% of theory,
M.p.: 148°–150° C.

| Calc.: | C | 65.91 | H | 6.28 | Cl | 8.84 | N | 6.98 |
|---|---|---|---|---|---|---|---|---|
| Found: | | 65.45 | | 6.36 | | 9.63 | | 6.84 |

(t) 4-[(1-(6-Methyl-2-piperidino-phenyl)-1-ethyl)-aminocarbonylmethyl]-benzoic acid
Yield: 33% of theory,
M.p.: 170° C.

| Calc.: | C | 72.60 | H | 7.41 | N | 7.36 |
|---|---|---|---|---|---|---|
| Found: | | 72.45 | | 7.34 | | 7.32 |

(u) 4-[(1-(2-(octahydro-isoindole-2-yl)-phenyl)-1-ethyl)-aminocarbonylmethyl]-benzoic acid
Yield: 64% of theory,
M.p.: 130° C.

| Calc.: | C | 73.86 | H | 7.43 | N | 6.89 |
|---|---|---|---|---|---|---|
| Found: | | 73.60 | | 7.47 | | 6.72 |

(v) 4-[(1-(2-Decahydro-isoquinoline-2-yl)-phenyl)-1-ethyl)-aminocarbonylmethyl]-benzoic acid
Yield: 71% of theory,
M.p.: 220°–221° C.

| Calc.: | C | 74.25 | H | 7.66 | N | 6.66 | m/e = 420 |
|---|---|---|---|---|---|---|---|
| Found: | | 74.45 | | 7.50 | | 6.58 | m/e = 420 |

(w) 4-[(1-(2-(1,2,3,4,5,6,7,8-Octahydro-isoindole-2-yl)-phenyl)-1-ethyl)-aminocarbonylmethyl]-benzoic acid
Yield: 99% of theory,
M.p.: 70° C. (decomp.)

| Calc.: | (× 0.5 H₂O) | C 73.05 | H | 7.30 | N | 6.54 | m/e = 418 |
|---|---|---|---|---|---|---|---|
| Found: | | 73.00 | | 7.16 | | 5.98 | m/e = 418 |

(x) 4-[(1-(4-Chloro-2-piperidino-phenyl)-1-ethyl)-aminocarbonylmethyl]-benzoic acid
Yield: 82.1% of theory,
M.p.: 200°–202° C.

| Calc.: | C | 65.91 | H | 6.29 | Cl | 8.84 | N | 6.99 |
|---|---|---|---|---|---|---|---|---|
| Found: | | 66.06 | | 6.40 | | 9.01 | | 6.93 |

(y) 4-[(1-(4-Methyl-2-piperidino-phenyl)-1-ethyl)-aminocarbonylmethyl]-benzoic acid
Yield: 66.5% of theory,
M.p.: 110°–115° C.

| Calc.: | C | 72.60 | H | 7.42 | N | 7.36 |
|---|---|---|---|---|---|---|
| Found | | 72.50 | | 7.52 | | 7.46 |

(z) 4-[(2-Piperidino-benzhydryl)-aminocarbonylmethyl]-benzoic acid
Yield: 88% of theory,
M.p.: 232°–234° C.

| Calc.: | C | 75.68 | H | 6.59 | N | 6.54 |
|---|---|---|---|---|---|---|
| Found: | | 72.16 | | 6.52 | | 6.74 |

(aa) 4-[(5-Chloro-2-piperidino-benzyhydryl)-aminocarbonylmethyl]-benzoic acid
Yield: 78.5% of theory,
M.p.: 255°–260° C.

| Calc.: | C | 70.05 | H | 5.88 | Cl | 7.66 | N | 6.05 |
|---|---|---|---|---|---|---|---|---|
| Found: | | 70.50 | | 5.76 | | 7.36 | | 6.06 |

(bb) 4-[(1-(4-Piperidino-phenyl)-1-ethyl)-aminocarbonylmethyl]-benzoic acid
Yield: 81% of theory,
M.p.: 208°–210° C.

| Calc.: | C | 72.11 | H | 7.15 | N | 7.64 |
|---|---|---|---|---|---|---|
| Found: | | 72.24 | | 7.26 | | 7.54 |

(cc) 4-[(1-(2-(4-Methyl-piperazino)-phenyl)-1-ethyl)-aminocarbonylmethyl]-benzoic acid
Yield: 65% of theory,
M.p.: 150°–153° C.

| Calc.: | C | 69.27 | H | 7.13 | N | 11.02 |
|---|---|---|---|---|---|---|
| Found: | | 69.62 | | 7.65 | | 10.64 |

(dd) 4-[(1-(2-(4-Benzyl-piperazino)-phenyl)-1-ethyl)-aminocarbonylmethyl]-benzoic acid hydrochloride
Yield: 32% of theory,
M.p.: 180° C.

| Calc.: | C | 68.07 | H | 6.53 | Cl | 7.18 | N | 8.51 |
|---|---|---|---|---|---|---|---|---|
| Found: | | 67.85 | | 6.56 | | 7.18 | | 8.51 |

(ee) 4-[(1-(2-(4-p-Chlorophenyl-piperazino)-phenyl)-1-ethyl)-aminocarbonylmethyl]-benzoic acid
Yield: 75% of theory,
M.p.: 212° C. (decomp.)

| Calc.: | C | 67.84 | H | 5.90 | Cl | 7.42 | N | 8.79 |
|---|---|---|---|---|---|---|---|---|
| Found: | | 67.74 | | 6.22 | | 7.59 | | 8.82 |

(ff) 4-[(α-Cyclohexyl-2-piperidino-benzyl)-aminocarbonylmethyl]-benzoic acid
Yield: 33% of theory,
M.p.: 199°–202° C.

| Calc.: | C | 74.62 | H | 7.89 | N | 6.45 |
|---|---|---|---|---|---|---|
| Found: | | 74.60 | | 7.54 | | 6.66 |

(gg) (+)-4-[(1-(2-Piperidino-phenyl)-1-ethyl)-aminocarbonylmethyl]-benzoic acid × 0.3H$_2$O
Yield: 40% of theory,
M.p.: 107° C. (decomp. (isopropanol/ether)
$[\alpha]_D^{20} = +7.3°$ (c=1; methanol)

| Calc.: | (× 0.3 H$_2$O) | C 71.02 | H 7.25 | N 7.52 | m/e = 366 |
|---|---|---|---|---|---|
| Found: | | 70.90 | 7.22 | 7.42 | m/e = 366 |

(hh) (−)-4-[(1-(2-Piperidino-phenyl)-1-ethyl)-aminocarbonylmethyl]-benzoic acid sodium salt
Crude yield of betain: 77% of theory,

| Calc.: | m/e = 366 |
|---|---|
| Found: | m/e = 366 |

Conversion into the sodium salt by means of 1 equivalent of sodium hydroxide solution in ethanol. M.p.: of the sodium salt: 190° C. (decomp.)
(ii) 4-[(1-(2-Piperidino-phenyl)-1-ethenyl)-aminocarbonylmethyl]-benzoic acid
Yield: 53.6% of theory,
M.p.: 158°–160° C. (ethanol)

| Calc.: | C | 72.51 | H | 6.64 | N | 7.69 |
|---|---|---|---|---|---|---|
| Found: | | 72.40 | | 6.34 | | 7.51 |

(jj) 4-[(1-(5-Chloro-2-piperidino-phenyl)-1-ethenyl)-aminocarbonylmethyl]-benzoic acid
Yield: 78.7% of theory,
M.p.: 198°–200° C. (acetone)

| Calc.: | C | 66.24 | H | 5.81 | Cl | 8.88 | N | 7.02 |
|---|---|---|---|---|---|---|---|---|
| Found: | | 65.74 | | 5.72 | | 9.37 | | 7.10 |

(kk) 4-[(α-Cyclohexylidene-2-piperidino-benzyl)-aminocarbonylmethyl]-benzoic acid
Yield: 21% of theory,
M.p.: 213°–216° C.

| Calc.: | C | 74.97 | H | 7.46 | N | 6.48 |
|---|---|---|---|---|---|---|
| Found: | | 74.73 | | 7.52 | | 6.48 |

(ll) 4-[(1-(6-Chloro-2-piperidino-phenyl)-1-ethenyl)-aminocarbonylmethyl]-benzoic acid
Yield: 39% of theory,
M.p.: 162° C.

| Calc.: | C 66.24 | H 5.81 | Cl 8.88 | N 7.02 | m/e = 398/400 |
|---|---|---|---|---|---|

| Found: | 66.48 | 5.84 | 8.88 | 6.85 | m/e = 398/400 |
|---|---|---|---|---|---|

(mm) 4-[(1-(6-Methyl-2-piperidino-phenyl)-1-ethenyl)-aminocarbonylmethyl]-benzoic acid
Yield: 49% of theory,
M.p.: 128°–130° C.

| Calc.: | m/e = 378 |
|---|---|
| Found: | m/e = 378 |

(nn) 4-[(1-(2-Piperidino-phenyl)-1-propenyl)-aminocarbonylmethyl]-benzoic acid
Yield: 65% of theory,
M.p.: 185°–187° C. (ethyl acetate) (Z-Form); 178°–180° C. (E-Form)

| Calc.: | C | 72.99 | H | 6.92 | N | 7.40 |
|---|---|---|---|---|---|---|
| Found: | | 73.10 | | 6.99 | | 7.56 |

(oo) 4-[(1-(5-Hydroxy-2-piperidino-phenyl)-1-ethyl)-aminocarbonylmethyl]-benzoic acid semihydrate
Saponification with 2.5 equivalents of sodium hydroxide.
Yield: 55.9% of theory,
Foam (from ether)

| Calc.: | (× 0.5 H$_2$O) | C | 67.50 | H | 6.95 | N | 7.16 |
|---|---|---|---|---|---|---|---|
| Found: | | | 67.11 | | 7.15 | | 6.87 |

(pp) 4-[(1-(2-(2-Methyl-pyrrolidino)-phenyl)-1-ethyl)-aminocarbonylmethyl]-benzoic acid
Yield: 62% of theory,
M.p.: 169°–172° C.

| Calc.: | C | 72.11 | H | 7.15 | N | 7.64 |
|---|---|---|---|---|---|---|
| Found: | | 71.96 | | 6.82 | | 7.51 |

(qq) 4-[(1-(5-Aminosulfonyl-2-piperidino-phenyl)-1-ethyl)-aminocarbonylmethyl]-benzoic acid
Yield: 19.2% of theory,
M.p.: 210° C. (decomp.)

| Calc.: | C | 59.30 | H | 6.11 | N | 9.43 | m/e = 445 |
|---|---|---|---|---|---|---|---|
| Found: | | 58.80 | | 5.87 | | 9.06 | m/e = 445 |

(rr) 4-[(1-(2-Piperidino-phenyl)-1-propyl)-aminocarbonylmethyl]-benzoic acid
Yield: 71.4% of theory,
M.p.: 208°–210° C. (ethanol)

| Calc.: | C | 72.61 | H | 7.42 | N | 7.36 |
|---|---|---|---|---|---|---|
| Found: | | 72.30 | | 7.44 | | 7.45 |

(ss) (−)-4-[(2-Piperidino-benzhydryl)-aminocarbonylmethyl]-benzoic acid
Yield: 86.8% of theory,
M.p.: 181°–182° C.

| Calc.: | C | 75.68 | H | 6.59 | N | 6.54 |
|---|---|---|---|---|---|---|

| -continued | | | |
|---|---|---|---|
| Found: | 75.33 | 6.45 | 6.33 |

$[\alpha]_D^{20} = -6.3°$ (c=1, methanol)

(tt) (+)-4-[(2-Piperidino-benzhydryl)-aminocarbonyl-methyl]-benzoic acid
Yield: 79.4% of theory,
M.p.: 180°–182° C.

| Calc.: | C | 75.68 | H | 6.59 | N | 6.54 |
|---|---|---|---|---|---|---|
| Found: | | 75.75 | | 6.73 | | 6.68 |

$[\alpha]_D^{20} = +5.8°$ (c=1, methanol)

Example 10

4-[(1-(2-Piperidino-phenyl)-1-ethyl)-aminocarbonylmethyl]-benzoic acid

A solution of 13.5 gm (0.338 mol) of sodium hydroxide in 50 ml of water was added to 88.8 gm (0.225 mol) of 4-[(1-(2-piperidino-phenyl)-ethyl)-aminocarbonylmethyl]-benzoic acid ethyl ester in 890 ml of ethanol, and the mixture was stirred at an internal temperature of 60° C. until no starting product could be detected in the thin layer chromatogram (approximately 45 minutes). After addition of 400 ml of water the reaction mixture was adjusted to 25° C. to a pH of 5.8 under pH-metric control by means of semi-concentrated hydrochloric acid. After a short time crystallization began. After standing overnight at 20° C., the precipitate was filtered off, and the crystals obtained were washed several times with water. Subsequently, the crystals were dissolved in methylene chloride and washed with a small amount of water. After drying of the organic phase over sodium sulfate, the solution was filtered, and the solvent was removed in vacuo, whereby a solid evaporation residue of 57.5 gm was obtained.

The ethanolic-hydrochloric filtrate (pH=5.8) was adjusted to a pH of 5.0 by means of semi-concentrated hydrochloric acid, and then the ethanol was distilled off in vacuo and the evaporated solution was cooled in ice. The resultant precipitate was filtered off, dissolved in methylene chloride, and separated from the aqueous phase, and the methylene chloride solution was dried, filtered, and evaporated in vacuo. The solid evaporation residue obtained was 13.0 gm. Both evaporation residues (a total of 70.5 gm) were recrystallized from a 5- to 6-fold amount of ethanol/water (80:20) under addition of activated charcoal.
Yield: 62% of theory,
M.p.: 163°–164° C.

| Calc.: | C | 72.11 | H | 7.15 | N | 7.64 |
|---|---|---|---|---|---|---|
| Found: | | 72.13 | | 7.25 | | 7.75 |

When, in a modified procedure, after saponification the pH was adjusted to 5.0 immediately after addition of water and cooling to 25° C., then, as described before, 75.9% of the dried evaporation residue were obtained without further processing of the ethanolic hydrochloric filtrate. Already before the final recrystallization, the residue supplied a correct elementary analysis.
M.p.: 172°–176° C.

| Calc.: | C | 72.11 | H | 7.15 | N | 7.64 |
|---|---|---|---|---|---|---|

| -continued | | | |
|---|---|---|---|
| Found: | 71.90 | 7.08 | 7.52 |

By use of procedures analogous to that of Example 10, the following compounds were prepared:

(a) 4-[(1-(5-Methyl-2-piperidino-phenyl)-1-ethyl)-aminocarbonylmethyl]-benzoic acid
Yield: 56.5% of theory,
M.p.: 215°–217° C. (ethanol)

| Calc.: | C | 72.61 | H | 7.42 | N | 7.36 |
|---|---|---|---|---|---|---|
| Found: | | 72.71 | | 7.49 | | 7.25 |

(b) 4-[(α-Carboxy-2-piperidino-benzyl)-aminocarbonylmethyl]-benzoic acid×0.66H$_2$O Prepared by saponification of the 4-[(α-methoxycarbonyl-2-piperidino-benzyl)-aminocarbonylmethyl]-benzoic acid ethyl ester with 2.5 equivalents of sodium hydroxide.
Yield: 72.2% of theory,
M.p.: 235°–240° C. (decomp.) (methanol/chloroform)

| Calc.: | (× 0.66 H$_2$O) | C | 64.69 | H | 6.33 | N | 6.85 |
|---|---|---|---|---|---|---|---|
| Found: | | | 64.64 | | 6.23 | | 6.61 |

Example 11

4-[(1-(2-Piperidino-phenyl)-1-ethyl)-aminocarbonylmethyl]-benzoic acid sodium salt monohydrate Five hundred milligram (1.26 mmol) of 4-[(2-piperidino-phenyl)-ethyl)-aminocarbonylmethyl]-benzoic acid ethyl ester in 5 ml of ethanol were stirred together with 1.26 ml of 1N sodium hydroxide solution for one hour at 50° C. After cooling to 0° C., the precipitated crystals were filtered off and washed with cold ethanol and with ether.
Yield: 238 mg (48.6% of theory),
M.p.: 245°–250° C.

| Calc.: | (× 1 H$_2$O) | C | 65.01 | H | 6.69 | N | 6.89 |
|---|---|---|---|---|---|---|---|
| Found: | | | 65.40 | | 6.83 | | 6.72 |

By use of procedures analogous to that of Example 11, the following compounds were prepared:

4-[(1-(5-Methoxy-2-piperidino-phenyl)-1-ethyl)-aminocarbonylmethyl]-benzoic acid sodium salt monohydrate
Yield: 17.5% of theory,
M.p.: 212°–215° C.

| Calc.: | (× 1 H$_2$O) | C | 63.28 | H | 6.70 | N | 6.42 |
|---|---|---|---|---|---|---|---|
| Found: | | | 63.20 | | 6.82 | | 6.51 |

Analogously to Example 9, the corresponding acid was obtained from the sodium salt as the monohydrate:
M.p.: 187°–189° C. (ethanol/water)

| Calc.: | (× 1 H$_2$O) | C | 66.40 | H | 7.29 | N | 6.76 |
|---|---|---|---|---|---|---|---|
| Found: | | | 66.87 | | 6.97 | | 6.80 |

Example 12

4-[(1-(2-Piperidino-phenyl)-1-ethyl)-aminocarbonylmethyl]-benzoic acid sodium salt×0.6H₂O An amount of 8.4 gm (0.0229 mol) of 4-[(1-(2-piperidino-phenyl)-ethyl)-aminocarbonylmethyl]-benzoic acid was dissolved at 60° to 65° C. in 80 ml of ethanol. To this solution 22.9 ml of 1N sodium hydroxide solution were added under stirring, and stirring was continued for 30 minutes. After cooling to 20° C., a precipitate was thereby obtained. After further cooling to 0° C., the precipitate was filtered and washed with cold ethanol and ether. The precipitate thus obtained (m.p.: 250°–251° C.) was recrystallized from ethanol/water (7:3).

Yield: 7.2 gm (78.6% of theory),
M.p.: 253°–255° C.

| Calc.: | (× 0.6 H₂O) | C | 66.18 | H | 6.61 | N | 7.02 |
|---|---|---|---|---|---|---|---|
| Found: | | | 66.10 | | 6.64 | | 7.13 |

Example 13

4-[(1-(2-Piperidino-phenyl)-1-ethyl)-aminocarbonylmethyl]-benzoic acid

One hundred milligrams (0.237 mmol) of 4-[(1-(2-piperidino-phenyl)-ethyl)-aminocarbonylmethyl]-benzoic acid-tert.butyl ester in 5 ml of benzene were heated together with some crystals of p-toluene-sulfonic acid hydrate to reflux temperature for half a day. According to the thin layer chromatogram no starting product could be then detected; however, according to the R$_f$-value and mass spectrum the desired product was formed.

M.p.: 163°–165° C.

| Calc.: | m/e = 366 |
|---|---|
| Found: | m/e = 366 |

Example 14

4-[(1-(2-Piperidino-phenyl)-1-ethyl)-aminocarbonylmethyl]-benzoic acid

A quantity of 0.46 gm (1 mmol) of 4-[(1-(2-piperidino-phenyl)-ethyl)-aminocarbonylmethyl]-benzoic acid benzyl ester in 20 ml of ethanol was hydrogenated at 0.25 gm of palladium/charcoal at 50° C. and a hydrogen pressure of 5 bar. After five hours the catalyst was filtered off over celite, and the filtrate was evaporated in vacuo. The evaporation residue was recrystallized from ethanol/water (8:2).

Yield: 0.26 gm (71% of theory),
M.p.: 163°–165° C.

| Calc.: | C | 72.11 | H | 7.15 | N | 7.64 |
|---|---|---|---|---|---|---|
| Found: | | 72.30 | | 7.25 | | 7.81 |

Example 15

4-[(1-(5-Chloro-2-piperidino-phenyl)-1-ethyl)-aminocarbonylmethyl]-benzoic acid An amount of 2.54 gm (0.02 mol) of oxalyl chloride was added dropwise at 0° to 5° C. to a stirred solution of 3.57 gm (0.01 mol) of N-[1-(5-chloro-2-piperidinophenyl)-ethyl]-N-[phenacetyl]-amine in 16 ml of carbon disulfide, and subsequently 2.67 gm 0.02 mol) of aluminium chloride were added. After one hour the same amounts of oxalyl chloride and aluminium chloride were added, and the mixture was subsequently heated for three hours up to 50° C. After cooling, ice water and hydrochloric acid were added, and the reaction mixture was extracted with chloroform. The organic extract was dried, filtered, and evaporated in vacuo. The evaporation residue was purified by column chromatography on silica gel (chloroform/methanol=10:1).

Yield: 0.60 gm (15% of theory),
M.p.: 213°–214° C. (ether)

| Calc.: | C | 65.91 | H | 6.29 | Cl | 8.85 | N | 6.99 |
|---|---|---|---|---|---|---|---|---|
| Found: | | 66.13 | | 6.05 | | 8.97 | | 7.25 |

Example 16

N-[4-Acetyl-phenacetyl]-N-[1-(5-chloro-2-piperidinophenyl)-ethyl]-amine

A solution of 0.6 ml (8.43 mmol) of acetyl chloride in 5 ml of methylene chloride was added at an internal temperature of 0° to 5° C. to 1.12 gm (8.43 mmol) of aluminium chloride in 10 ml of methylene chloride. Subsequently, at 0° to 5° C. the solution of 1 gm (2.81 mmol) of N-[1-(5-chloro-2-piperidino-phenyl)-ethyl]-N-[phenacetyl]-amine in 5 ml of methylene chloride was added under stirring. The reaction mixture was stirred for one hour at 3° C. and for two days at 20° C. After decomposition under cooling with ice water and hydrochloric acid, the methylene chloride phase was separated, and the aqueous phase was extracted with chloroform. The combined organic phases were dried over sodium sulfate, filtered, and evaporated in vacuo. The evaporation residue was purified by column chromatography on silica gel (toluene/acetone=4:1).

Yield: 0.28 gm (25% of theory),
M.p.: 160°–161° C.

| Calc.: | C 69.24 | H 6.82 | Cl 8.89 | N 7.02 | m/e = 398/400 |
|---|---|---|---|---|---|
| Found: | 69.55 | 6.99 | 9.45 | 6.85 | m/e = 398/400 |

Example 17

4-[(1-(5-Chloro-2-piperidino-phenyl)-1-ethyl)-aminocarbonylmethyl]-benzoic acid A solution of 1.23 gm (0.0031 mol) of N-[4-acetyl-phenacetyl]-N-[1-(5-chloro-2-piperidino-phenyl)-ethyl]-amine in 12 ml of dioxane was added dropwise within 15 minutes at 35° to 40° C. to a stirred sodium hypobromite solution [prepared from 1.84 gm (0.046 mol) of sodium hydroxide, dissolved in 9 ml of water, and 0.72 ml (0.014 mol) of bromine under ice cooling]. After 40 minutes at 35° to 40° C. aqueous sodium bisulfite solution and water were added, and the mixture was evaporated in vacuo. The residue was dissolved with water, acidified under cooling with 2N hydrochloric acid, and extracted with ether/ethyl acetate. The organic phase was dried, filtered, and evaporated in vacuo. The evaporation residue was recrystallized from ether.

Yield: 0.14 gm (11% of theory),
M.p.: 213°–215° C.

| Calc.: | C | 65.91 | H | 6.29 | Cl | 8.85 | N | 6.99 |
|--------|---|-------|---|------|----|----|---|------|
| Found: |   | 65.78 |   | 5.98 |    | 8.95 |   | 7.17 |

By use of a procedure analogous to that of Example 17, the following compound was prepared:
4-[(1-(2-Piperidino-phenyl)-1-ethyl)-aminocarbonylmethyl]-benzoic acid
Yield: 15% of theory,
M.p.: 170°–171° C.

| Calc.: | C | 72.11 | H | 7.15 | N | 7.64 |
|--------|---|-------|---|------|---|------|
| Found: |   | 72.45 |   | 7.01 |   | 7.48 |

Example 18

4-[(1-(2-Piperidino-phenyl)-1-ethyl)-aminocarbonylmethyl]-benzaldehyde

The above compound was prepared from 4-[(1-(2-piperidinophenyl)-ethyl)-aminocarbonylmethyl]-benzyl alcohol by oxidation with active manganese dioxide in absolute acetone and subsequent purification by column chromatography on silica gel (chloroform/acetone=20:1).
Yield: 4% of theory,
M.p.: 159° C.

| Calc.: | C | 75.40 | H | 7.48 | N | 7.99 |
|--------|---|-------|---|------|---|------|
| Found: |   | 75.05 |   | 7.18 |   | 7.67 |

Example 19

4-[(1-(2-Piperidino-phenyl)-1-ethyl)-aminocarbonylmethyl]-benzoic acid

The above compound was prepared from 4-[(1-(2-piperidinophenyl)-ethyl)-aminocarbonylmethyl]-benzaldehyde by heating with silver oxide in the presence of 1N sodium hydroxide solution for 20 minutes in a steam bath, subsequent acidification with 2N sulfuric acid at a pH of 5, extraction with ethyl acetate, and purification by column chromatography on silica gel (toluene/acetone=1:1).
Yield: 3% of theory,
M.p.: 168°–170° C.

| Calc.: | m/e = 366 |
|--------|-----------|
| Found: | m/e = 366 |

Example 20

4-[(1-(2-Piperidino-phenyl)-1-ethyl)-aminocarbonylmethyl]-benzoic acid ethyl ester An amount of 5.5 gm (0.014 mol) of 4-[(1-(2-piperidinophenyl)-ethenyl)-aminocarbonylmethyl]-benzoic acid ethyl ester in 110 ml of ethanol was hydrogenated in the presence of 1.5 gm of palladium/charcoal (10%) at 20° C. and a hydrogen pressure of 5 bar. After 30 minutes the catalyst was filtered off over celite, and the filtrate was evaporated in vacuo to a volume of 20 ml. One hundred milliliters of petroleum ether were added, and the mixture was cooled to 0° C.
Yield: 4.7 gm (85.5% of theory),
M.p.: 152°–154° C.

| Calc.: | C | 73.07 | H | 7.66 | N | 7.10 |
|--------|---|-------|---|------|---|------|
| Found: |   | 72.80 |   | 7.63 |   | 7.08 |

By use of a procedure analogous to that of Example 20, the following compound was prepared:
4-[(1-(2-Piperidino-phenyl)-1-propyl)-aminocarbonylmethyl]-benzoic acid ethyl ester
Yield: 70.8% of theory,
M.p.: 132°–134° C. (ether)

| Calc.: | C | 73.50 | H | 7.50 | N | 6.86 |
|--------|---|-------|---|------|---|------|
| Found: |   | 73.71 |   | 7.88 |   | 6.77 |

Example 21

4-[(1-(2-Piperidino-phenyl)-1-ethyl)-aminocarbonylmethyl]-benzoic acid

One hundred milligrams (0.2744 m mol) of 4-[(1-(2-piperidino-phenyl)-ethenyl)-aminocarbonylmethyl]-benzoic acid in 5 ml of absolute ethanol were hydrogenated in the presence of 50 mg of palladium/charcoal (10%) at 20° C. and at a hydrogen pressure of 1 bar under shaking. After 1.5 hours the catalyst was filtered off, and the filtrate was evaporated in vacuo.
Yield: 91% of theory,
M.p.: 170°–171° C.

| Calc.: | m/e = 366 |
|--------|-----------|
| Found: | m/e = 366 |

Example 22

4-[(1-(2-Piperidino-phenyl)-1-ethyl)-aminocarbonylmethyl]-benzoic acid semihydrate Two hundred milligrams (0.5014 m mol) of 4-[(1-(5-chloro-2-piperidino-phenyl)-ethenyl)-aminocarbonylmethyl)-benzoic acid in 10 ml of absolute ethanol were hydrogenated in the presence of 100 mg of palladium/charcoal (10%) at 50° C. and at a hydrogen pressure of 1 bar under shaking. After 1.5 hours the catalyst was filtered off, 5 ml of water were added, the mixture was adjusted to a pH of 6 by means of 1N sodium hydroxide solution, and the ethanol was evaporated in vacuo. A colorless precipitate was obtained, which was filtered off after cooling.
Yield: 100 mg (53.1% of theory),
M.p.: 135° C.

| Calc.: | (× 0.5 H₂O) | C | 70.36 | H | 7.24 | N | 7.46 | m/e = 366 |
|--------|-------------|---|-------|---|------|---|------|-----------|
| Found: |             |   | 70.31 |   | 7.44 |   | 7.78 | m/e = 366 |

Example 23

4-[(1-(2-Piperidino-phenyl)-1-ethyl)-aminocarbonylmethyl]-benzoic acid ethyl ester An amount of 1.6 ml of conc. sulfuric acid was added in small drops to a mixture of 2 gm (9.74 m mol) of 1-(2-piperidino-phenyl)-ethanol and 4 gm (21.1 m mol) of 4-cyanomethylbenzoic acid ethyl ester under stirring and cooling with ice by keeping the internal temperature at 35° to 40° C. Subsequently, the mixture was heated for 2.5 hours in a bath of 80° C., a further 2 gm (10.5 m mol) of 4-cyanomethyl benzoic acid ethyl ester and 0.8 ml of conc. sulfuric acid were added, and heating was continued for one hour at 80° C. and for three hours at 100° C. After that time no starting alcohol could be detected in a thin layer chromatogram. After cooling to 20° C. the mixture was layered with ethyl acetate, and under stirring and cooling ice water was added. After extraction several times with ethyl acetate, the organic extract was dried over sodium sulfate, filtered, and evaporated in vacuo. The evaporation residue was purified by column chromatography on silica gel (toluene/acetone=10:1). From the pre-fractions 0.5 gm of 2-piperidino-styrol was isolated.

Yield: 0.66 gm (17.4% of theory),
M.p.: 147°-150° C. (ethanol)

| Calc.: | C | 73.07 | H | 7.66 | N | 7.10 |
|---|---|---|---|---|---|---|
| Found: |  | 73.26 |  | 7.55 |  | 6.90 |

Example 24

4-[(1-(5-Chloro-2-piperidino-phenyl)-1-ethyl)-aminocarbonylmethyl]-benzoic acid

A quantity of 0.4 ml (5.55 m mol) of thionyl chloride was added dropwise to a stirred solution of 1 gm (5.55 m mol) of 4-carboxy-phenyl-acetic acid and of 1.32 gm (5.55 m mol) of 1-(5-chloro-2-piperidino-phenyl)-ethylamine in 10 ml of absolute pyridine, whereby the internal temperature rose from 20° C. to 35° C. The deep-brown reaction mixture was stirred for three hours at 20° C. and evaporated in vacuo. The evaporation residue was distributed between water (at pH=3 after addition of 2N hydrochloric acid) and chloroform. The organic extract was dried, filtered, and evaporated in vacuo. The evaporation residue was purified by column chromatography on silica gel (chloroform/methanol=10:1).

Yield: 1.06 gm (48% of theory),
M.p.: 212°-214° C. (ether)

| Calc.: | C | 65.91 | H | 6.29 | Cl | 8.85 | N | 6.99 |
|---|---|---|---|---|---|---|---|---|
| Found: |  | 65.79 |  | 6.01 |  | 8.69 |  | 6.87 |

By use of procedures analogous to that of Example 24, the following compounds were obtained:

(a) 4-[(1-(2-Piperidino-phenyl)-1-ethyl)-aminocarbonylmethyl]-benzoic acid
Yield: 52% of theory,
M.p.: 169°-171° C.

| Calc.: | C | 72.11 | H | 7.15 | N | 7.64 |
|---|---|---|---|---|---|---|
| Found: |  | 71.84 |  | 6.87 |  | 7.72 |

(b) 4-[(1-(2-(4-Oxo-piperidino)-phenyl)-1-ethyl)-aminocarbonylmethyl]-benzoic acid
Yield: 32% of theory,
M.p.: 177°-180° C. (decomp.) (acetone/petroleum ether)

| Calc.: | C | 69.46 | H | 6.36 | N | 7.36 |
|---|---|---|---|---|---|---|
| Found: |  | 69.62 |  | 6.41 |  | 7.50 |

(c) 4-[(1-(2-(4-Hydroxy-piperidino)-phenyl)-1-ethyl)-aminocarbonylmethyl]-benzoic acid×0.66 H$_2$O
Yield: 23.5% of theory,
M.p.: 176°-179° C. (decomp.) (acetone/petroleum ether)

| Calc.: | (×0.66 H$_2$O) | C | 66.97 | H | 6.81 | N | 7.10 |
|---|---|---|---|---|---|---|---|
| Found: |  |  | 67.12 |  | 6.78 |  | 7.26 |

(d) 4-[(1-(2-Piperidino-phenyl)-1-ethyl)-aminocarbonylmethyl]-benzonitrile
Prepared from 4-cyano-phenyl acetic acid.
Yield: 51% of theory,
M.p.: 155°-157° C. (ethyl acetate)

| Calc.: | C | 76.05 | H | 7.25 | N | 12.09 |
|---|---|---|---|---|---|---|
| Found: |  | 76.41 |  | 7.10 |  | 12.20 |

EXAMPLE 25

4-[(1-(2-Piperidino-phenyl)-1-ethyl)-aminocarbonylmethyl]-benzyl alcohol

Prepared from 4-[(1-(2-piperidino-phenyl)-ethyl)-aminocarbonylmethyl]-benzoic acid ethyl ester by lithium aluminum hydride reduction in tetrahydrofuran.
Yield: 39% of theory,
M.p.: 104°-106° C.

| Calc.: | C | 74.96 | H | 8.00 | N | 7.94 |
|---|---|---|---|---|---|---|
| Found: |  | 74.80 |  | 7.80 |  | 7.80 |

Example 26

4-[(1-(2-Piperidino-phenyl)-1-ethyl)-aminocarbonylmethyl]-benzyl malonic acid diethyl ester A solution of 3.7 gm (10 m mol) of 4-[(1-(2-piperidinophenyl)-ethyl)-aminocarbonylmethyl]-benzyl chloride [m.p.: 123°-125° C.; prepared from the alcohol described in Example 25 by means of thionyl chloride in chloroform] in 35 ml of absolute ethanol was added dropwise to a solution of sodium malonic acid diethyl ester [prepared from 0.7 gm (30 m mol) of sodium in 25 ml of absolute ethanol and 4.8 gm (30 m mol) of malonic acid diethyl ester]. A catalytic amount of potassium iodide was added, and the mixture was refluxed for 16 hours. After evaporation in vacuo, the evaporation residue was adjusted neutral by means of hydrochloric acid and extracted with methylene chloride. The organic extract was dried over sodium sulfate, filtered, and evaporated in vacuo. The evaporation residue was purified by column chromatography on silica gel (toluene/acetone=6:1).
Yield: 3.0 gm (60% of theory),
M.p.: <20° C.

| Calc.: | m/e = 494 |
|---|---|
| Found: | m/e = 494 |

Example 27

3-[4-[(1-(2-Piperidino-phenyl)-1-ethyl)-aminocarbonylmethyl]-phenyl]-propionic acid Five milliliters of 1N sodium hydroxide solution were added to a solution of 0.85 gm (1.7 m mol) of 4-[(1-(2-piperidino-phenyl)-ethyl)-aminocarbonylmethyl]-benzyl malonic acid diethyl ester in 18 ml of ethanol. After stirring for two hours at 50° C., the mixture was evaporated in vacuo, and water and 5 ml of 1N hydrochloric acid were added. The precipitate formed was filtered off, dried in vacuo, and heated for 30 minutes up to 120° C., whereby carbon dioxide was split off. The product obtained was purified by column chromatography on silica gel (chloroform/methanol=20:1).
Yield: 0.15 gm (22.4% of theory),
M.p.: 68°-70° C.

| Calc.: | C | 73.06 | H | 7.67 | N | 7.10 | m/e = 394 |
|---|---|---|---|---|---|---|---|
| Found: | | 72.64 | | 7.42 | | 6.81 | m/e = 394 |

Example 28
4-[(1-(2-Piperidino-phenyl)-1-ethyl)-aminocarbonylmethyl]-benzaldehyde The above compound was prepared by the heating of crude N¹-[4-[(1-(2-piperidino-phenyl)-ethyl)-aminocarbonylmethyl]benzoyl]-N²-tosyl-hydrazine with anhydrous sodium carbonate at 160°-170° C. in ethylene glycol [prepared from 4-[(1-(2-piperidino-phenyl)-ethyl)-aminocarbonylmethyl]-benzoic acid and tosylhydrazine with carbonyl diimidazole in tetrahydrofuran].
Yield: 10% of theory,
M.p.: 159° C.

| Calc.: | C | 75.40 | H | 7.48 | N | 7.99 |
|---|---|---|---|---|---|---|
| Found: | | 74.99 | | 7.24 | | 7.60 |

Example 29
4-[(1-(2-Piperidino-phenyl)-1-ethyl)-aminocarbonylmethyl]-benzoic acid An amount of 0.50 gm (1.247 m mol) of 4-[(1-(5-chloro-2-piperidino-phenyl)-ethyl)-aminocarbonylmethyl]-benzoic acid in 20 ml of absolute ethanol were hydrogenated at 0.25 gm of palladium/charcoal (10%) at 50° C. and a hydrogen pressure of 5 bar. After two hours the catalyst was filtered off over celite, and after evaporation in vacuo the residue was distributed at a pH of 6 between water and ethyl acetate. The organic extract was washed with water, dried, filtered, and evaporated in vacuo.
Yield: 0.31 gm (67% of theory),
M.p.: 170°-172° C. (ether)

| Calc.: | C | 72.11 | H | 7.15 | N | 7.64 |
|---|---|---|---|---|---|---|
| Found: | | 71.76 | | 6.98 | | 7.51 |

By use of procedures analogous to that of Example 29, the following compounds were prepared:
(a) 4-[(2-(2-Piperidino-phenyl)-2-propyl)-aminocarbonylmethyl]-benzoic acid
Yield: 68.5% of theory,
M.p.: 213°-215° C.

| Calc.: | C | 72.61 | H | 7.42 | N | 7.36 |
|---|---|---|---|---|---|---|
| Found: | | 72.43 | | 7.25 | | 7.40 |

(b) 4-[(1-(2-Dimethylamino-phenyl)-1-ethyl)-aminocarbonylmethyl]-benzoic acid
Yield: 53.3% of theory,
M.p.: 165°-168° C. (acetone/petroleum ether)

| Calc.: | C | 69.92 | H | 6.79 | N | 8.59 |
|---|---|---|---|---|---|---|
| Found: | | 69.88 | | 6.83 | | 8.49 |

(c) 4-[(2-Pyrrolidino-benzyl)-aminocarbonylmethyl]-benzoic acid
Yield: 55% of theory,
M.p.: 212°-215° C. (methanol)

| Calc.: | C | 70.99 | H | 6.55 | N | 8.28 |
|---|---|---|---|---|---|---|
| Found: | | 70.97 | | 6.91 | | 8.15 |

(d) 4-[(1-(2-Pyrrolidino-phenyl)-1-ethyl)-aminocarbonylmethyl]-benzoic acid
Yield: 25% of theory,
M.p.: 155°-157° C. (acetone/ether)

| Calc.: | C | 71.57 | H | 6.86 | N | 7.95 |
|---|---|---|---|---|---|---|
| Found: | | 71.22 | | 7.75 | | 8.42 |

(e) 4-[(2-Piperidino-benzyl)-aminocarbonylmethyl]-benzoic acid
Yield: 60.4% of theory,
M.p.: 175°-177° C. (acetone)

| Calc.: | C | 71.57 | H | 6.86 | N | 7.95 |
|---|---|---|---|---|---|---|
| Found: | | 71.43 | | 7.00 | | 8.09 |

(f) 4-[(2-(2-Piperidino-phenyl)-1-ethyl)-aminocarbonylmethyl]-benzoic acid
Yield: 60.4% of theory,
M.p.: 164°-166° C. (ethyl acetate)

| Calc.: | C | 72.11 | H | 7.15 | N | 7.64 |
|---|---|---|---|---|---|---|
| Found: | | 72.35 | | 7.18 | | 7.76 |

(g) 4-[(1-(2-(2-Methyl-piperidino)-phenyl)-1-ethyl)-aminocarbonylmethyl]-benzoic acid
Yield: 90.9% of theory,
M.p.: 171°-173° C. (petroleum ether/acetone)

| Calc.: | C | 72.61 | H | 7.42 | N | 7.36 |
|---|---|---|---|---|---|---|
| Found: | | 72.30 | | 7.39 | | 7.43 |

(h) 4-[(1-(2-(3-Methyl-piperidino)-phenyl)-1-ethyl)-aminocarbonylmethyl]-benzoic acid
Yield: 86.3% of theory,
M.p.: 170°-173° C. (petroleum ether/acetone)

| Calc.: | C | 72.61 | H | 7.42 | N | 7.36 |
|---|---|---|---|---|---|---|
| Found: | | 72.20 | | 7.28 | | 7.12 |

(i) 4-[(1-(2-Dipropylamino-phenyl)-1-ethyl)-aminocarbonylmethyl]-benzoic acid
Yield: 51.1% of theory,
M.p.: 175°-178° C. (ethyl acetate)

| Calc.: | C | 72.22 | H | 7.91 | N | 7.32 |
|---|---|---|---|---|---|---|

| Found: | 72.10 | 8.05 | 7.69 |

(j) 4-[(1-(2-Piperidino-phenyl)-2-methyl-1-propyl)-aminocarbonylmethyl]benzoic acid
Yield: 86% of theory,
M.p.: 215°–217° C. (acetone)

| Calc.: | C | 73.06 | H | 7.67 | N | 7.10 |
| Found: | | 73.10 | | 7.55 | | 6.99 |

(k) 4-[(1-(2-Piperidino-phenyl)-1-ethyl)-aminocarbonylmethyl]-benzoic acid methyl ester
Prepared from 4-[(1-(5-chloro-2-piperidino-phenyl)-ethyl)aminocarbonylmethyl]-benzoic acid methyl ester.
Yield: 37.2% of theory,
M.p.: 145°–147° C.

| Calc.: | C | 72.61 | H | 7.42 | N | 7.36 |
| Found: | | 72.47 | | 7.30 | | 7.56 |

(l) 4-[(2-Piperidino-anilino)-carbonylmethyl]-benzoic acid methyl ester
Prepared from 4-[(5-chloro-2-piperidino-anilino)-carbonylmethyl]-benzoic acid methyl ester.
Yield: 60% of theory,
M.p.: 85°–86° C. (toluene/petroleum ether)

| Calc.: | C | 71.57 | H | 6.86 | N | 7.96 |
| Found: | | 71.48 | | 6.92 | | 8.39 |

(m) N-phenacetyl-N-[1-(2-piperidino-phenyl)-ethyl]-amine
Prepared from N-[1-(5-chloro-2-piperidino)-1-ethyl]-N-phenacetyl-amine.
Yield: 54.6% of theory,
M.p.: 120°–121° C. (petroleum ether/acetone)

| Calc.: | C | 78.22 | H | 8.13 | N | 8.69 |
| Found: | | 77.90 | | 8.24 | | 8.75 |

Example 30

4-[(1-(5-Amino-2-piperidino-phenyl)-1-ethyl)-aminocarbonylmethyl]-benzoic acid methyl ester Two grams (0.0047 mol) of 4-[(1-(5-nitro-2-piperidinophenyl)-ethyl)-aminocarbonylmethyl]-benzoic acid methyl ester in 20 ml of dimethyl formamide were hydrogenated in the presence of 0.2 gm of palladium charcoal (10%) in a Parr apparatus at 20° C. and a hydrogen pressure of 1 bar. When the hydrogen absorption was finished (2 hours), the catalyst was filtered off over celite and evaporated to dryness in vacuo.
Yield: 1.8 gm (95% of theory),
M.p.: 140°–142° C. (toluene).

By use of procedures analogous to that of Example 30, the following compounds were prepared:
(a) 4-[(1-(5-Amino-2-piperidino-phenyl)-1-ethyl)-aminocarbonylmethyl]-benzoic acid ethyl ester
Yield: 97.8% of theory,
M.p.: 148°–149.5° C. (cyclohexane)

| Calc.: | C | 70.39 | H | 7.63 | N | 10.26 |
| Found: | | 70.20 | | 7.67 | | 9.60 |

(b) 4-[(1-(5-Amino-2-piperidino-phenyl)-1-ethyl)-aminocarbonylmethyl]-benzoic acid
The above compound was prepared from 4-[(1-(5-nitro-2-piperidino-phenyl)-ethyl)-aminocarbonylmethyl]-benzoic acid.
Yield: 85.7% of theory,
M.p.: 223°–225° C. (ether)

| Calc.: | C | 69.27 | H | 7.13 | N | 11.02 |
| Found: | | 69.18 | | 7.04 | | 11.35 |

(c) N-[4-Amino-phenacetyl]-N-[1-(2-piperidino-phenyl)-1-ethyl]-amine-dihydrochloride semihydrate Prepared from N-[4-nitro-phenacetyl]-N-[1-(2-piperidinophenyl)-ethyl]-amine. Conversion of the crude amino compound into the dihydrochloride in ethanol by means of ethereal hydrochloric acid.
Yield: 17.5% of theory,
M.p.: 238° C. (decomp.)

| Calc.: | (× 2 HCL × 0.5 H₂O) | C | 60.12 | H | 7.21 | Cl | 16.91 |
| Found: | | | 60.52 | | 7.52 | | 17.05 |

Example 31

4-[(1-(5-Bromo-2-piperidino-phenyl)-1-ethyl)-aminocarbonylmethyl]-benzoic acid

A solution of 0.072 gm (1.05 m mol) of sodium nitrite in 0.5 ml of water was added dropwise at an internal temperature of 0° to 5° C. to 0.40 gm (1.05 m mol) of 4-[(1-(5-amino-2-piperidino-phenyl)-ethyl)-aminocarbonylmethyl]-benzoic acid in 2 ml of semi-concentrated aqueous hydrobromic acid. The thus obtained diazonium salt solution was then added dropwise to 0.196 gm of copper-(I) bromide in 2 ml of 48% hydrobromic acid, whereby strong formation of gas occurred. The reaction mixture was stirred for 1.5 hours at an internal temperature of 45° to 50° C., cooled, and adjusted to pH 4 by means of 4N sodium hydroxide solution. After extraction with warm ethyl acetate, the extract was washed with water, dried, and filtered. After evaporation in vacuo, the residue obtained was purified by column chromatography on silica gel (chloroform/methanol=7:1).
Yield: 0.08 gm (17% of theory),
M.p.: 212°–213° C. (ethyl acetate/petroleum ether)

| Calc.: | C | 59.32 | H | 5.66 | Br | 17.94 | N | 6.29 |
| Found: | | 59.30 | | 5.71 | | 17.85 | | 6.48 |

By use of a procedure analogous to that of Example 31, the following compound was prepared:
4-[(1-(5-Chloro-2-piperidino-phenyl)-1-ethyl)-aminocarbonylmethyl]-benzoic acid
Prepared by diazotization of 4-[(1-(5-amino-2-piperidino-phenyl)-ethyl)-aminocarbonylmethyl]-benzoic acid in conc. HCl and Sandmeyer reaction with copper-(I) chloride.

Yield: 25.2% of theory,
M.p.: 213°-215° C.

| Calc.: | 65.91 | H | 6.29 | Cl | 8.85 | N | 6.99 |
|---|---|---|---|---|---|---|---|
| Found: | 66.20 | | 6.31 | | 8.87 | | 6.82 |

If the reaction is carried out in hydrochloric acid without copper-(I) chloride, a yield of 19% of theory is obtained. Furthermore, 9% of the corresponding 5-hydroxy compound is obtained.

Example 32

4-[(1-(5-Iodo-2-piperidino-phenyl)-1-ethyl)-aminocarbonylmethyl]-benzoic acid ethyl ester A solution of 0.17 gm (2.44 m mol) of sodium nitrite in 0.52 ml of water was slowly added dropwise at 0° to 5° C. under stirring to 1.0 gm (2.44 m mol) of 4-[(1-(5-amino-2-piperidino-phenyl)-ethyl)-aminocarbonylmethyl]-benzoic acid ethyl ester in 1.9 ml of semi-concentrated hydriodic acid, and the solution was warmed to 20° C. within one hour. After heating for two hours at 100° C., the reaction mixture was cooled and extracted with ethyl acetate. The organic phase was washed with dilute sodium bicarbonate solution and with water, dried over sodium sulfate, filtered, and evaporated in vacuo. The evaporation residue was purified by column chromatography on silica gel (toluene/acetone=5:1).

Yield: 0.011 gm (0.93% of theory),
M.p.: 145°-147° C. (ether)

| Calc.: | C | 55.39 | H | 5.62 | N | 5.38 | m/e = 520 |
|---|---|---|---|---|---|---|---|
| Found: | | 55.95 | | 5.53 | | 5.05 | m/e = 520 |

Example 33

4-[(1-(5-Cyano-2-piperidino-phenyl)-1-ethyl)-aminocarbonylmethyl]-benzoic acid ethyl ester A solution of 0.34 gm (4.88 m mol) of sodium nitrite in 2.3 ml of water was added dropwise under stirring at −5° to 0° C. to 2.0 gm (4.88 m mol) of 4-[(1-(5-amino-2-piperidino-phenyl)-ethyl)-aminocarbonylmethyl]-benzoic acid ethyl ester in 4.0 ml of water and 3.5 ml of conc. hydrochloric acid. The mixture was stirred for 15 minutes and then neutralized with 1.1 gm of calcium carbonate. The suspension thus obtained was rinsed with 2×15 ml of water into a 0° C. solution, which was prepared from 0.568 gm (6.34 m mol) of copper-(I) cyanide, 1.24 gm (19 m mol) of potassium cyanide, and 5.8 ml of water, whereby a red-colored precipitate was immediately obtained. The reaction mixture was heated under stirring for 30 minutes at an internal temperature of 45° C., then for 30 minutes at 70° C. and for 60 minutes at 95° C. The red-colored spot was then no longer visible in the thin layer chromatogram.

The reaction mixture was cooled to 20° C. and extracted with ethyl acetate. The organic extract was dried over sodium sulfate, filtered, and evaporated in vacuo. The evaporation residue was purified by two column chromatographies on silica gel [(a) toluene/acetone=10:1, (b) methylene chloride/acetonitrile/glacial acetic acid=10:1:0.05]. In addition to the corresponding 5-Cl- and 5-H-compounds, the desired 5-cyano compound was obtained.

Yield: 0.186 gm (9% of theory),
M.p.: 165°-167° C. (ether)

| Calc.: | C | 71.58 | H | 6.96 | N | 10.02 | m/e = 419 |
|---|---|---|---|---|---|---|---|
| Found: | | 71.64 | | 6.94 | | 9.72 | m/e = 419 |

Example 34

4-[(1-(5-Aminosulfonyl-2-piperidino-phenyl)-1-ethyl)-aminocarbonylmethyl]-benzoic acid ethyl ester (a) A solution of 0.37 gm (5.36 m mol) of sodium nitrite in 0.7 ml of water was added dropwise under stirring at 4° to 6° C. to a suspension of 2.0 gm (4.88 m mol) of 4-[(1-(5-amino-2-piperidino-phenyl)-aminocarbonylmethyl]-benzoic acid ethyl ester in 2.02 ml of semi-concentrated hydrochloric acid. Subsequently, 0.37 gm (3.89 m mol) of magnesium chloride were added. The mixture thus obtained was subsequently added dropwise at 30° C. to a solution, which was prepared from 4.9 ml of glacial acetic acid (saturated with sulfur dioxide) and 0.27 gm of copper-(II) chloride dihydrate. Thereby the internal temperature rose to 40° C., and nitrogen was formed. After stirring for 15 minutes in a bath of 50° C., 7.5 ml of water were added, and the mixture was extracted with chloroform. The organic extract was dried over sodium sulfate, filtered, and evaporated in vacuo. The viscous, red-brown evaporation residue (2.7 gm still chloroform-containing) contained besides the corresponding 5-chloro-compound the desired 4-[(1-(5-chlorosulfonyl-2-piperidino-phenyl)-ethyl)-aminocarbonylmethyl]-benzoic acid ethyl ester.

(b) A solution of the evaporation residue obtained according to step (a) in 10 ml of chloroform was added dropwise at 2° C. under stirring to 50 ml of conc. ammonia. After 30 minutes saturated sodium chloride solution was added to obtain separation of the phases. After extraction with chloroform, the organic extract was dried, filtered, and evaporated in vacuo. The evaporation residue was purified by column chromatography on silica gel (chloroform/methanol=10:1). In addition to 55% of the corresponding 5-chloro-compound, the desired 5-aminosulfonyl compound was obtained as foam.

Yield: 32% of theory,

| Calc.: | m/e = 473 |
|---|---|
| Found: | m/e = 473 |

Example 35

4-[(1-(5-Dimethylamino-2-piperidino-phenyl)-1-ethyl)-aminocarbonylmethyl]-benzoic acid A tenth of a gram (1.589 m mol) of sodium cyanoborohydride and, after two minutes, 0.056 ml of glacial acetic acid were added at 20° C. to a stirred solution of 0.20 gm (0.5242 m mol) of 4-[(1-(5-amino-2-piperidino-phenyl)-ethyl)-aminocarbonylmethyl]-benzoic acid and 0.45 ml of 40% formalin in 2 ml of acetonitrile and 1 ml of absolute dimethyl formamide. After 1.5 hours the reaction mixture was evaporated in vacuo. The evaporation residue was dissolved in water by addition of hydrochloric acid at a pH of 2 to 3. After extraction with chloroform several times the aqueous phase was adjusted to a pH of 6 to 7 by means of saturated sodium bicarbonate solution and extracted several times with chloroform. This organic extract was dried and filtered.

After evaporation in vacuo the evaporation residue was recrystallized from isopropanol. The colorless crystals were washed with absolute ether.

Yield: 0.09 gm (42.8% of theory),
M.p.: 185° C. (decomp. from 175° C.)

| Calc.: | C | 70.39 | H | 7.63 | N | 10.26 |
|---|---|---|---|---|---|---|
| Found: |   | 70.10 |   | 7.63 |   | 10.47 |

Example 36

4-[(1-(5-Acetylamino-2-piperidino-phenyl)-1-ethyl)-aminocarbonylmethyl]-benzoic acid An amount of 0.10 gm (0.262 m mol) of 4-[(1-(5-amino-2-piperidino-phenyl)-ethyl)-aminocarbonylmethyl]-benzoic acid in 1 ml of acetic anhydride was stirred for six hours at 20° C., evaporated in vacuo, and distilled off several times with toluene, and the evaporation residue was recrystallized from ether.

Yield: 0.08 gm (72.7% of theory),
M.p.: 241°–243° C.

| Calc.: | C | 68.07 | H | 6.90 | N | 9.92 |
|---|---|---|---|---|---|---|
| Found: |   | 67.53 |   | 6.83 |   | 9.72 |

Example 37

4-[(1-(5-Benzoylamino-2-piperidino-phenyl)-1-ethyl)-aminocarbonylmethyl]-benzoic acid An amount of 0.30 ml (2.62 m mol) of benzoyl chloride was added dropwise to a solution of 1 gm (2.62 m mol) of 4-[(1-(5-amino-2-piperidino-phenyl)-ethyl)-aminocarbonylmethyl]-benzoic acid and of 0.37 ml (2.62 m mol) of triethylamine in 10 ml of anhydrous dimethyl formamide. After stirring for two hours at 20° to 30° C., the reaction mixture was evaporated in vacuo and distributed between water and ethyl acetate. The organic phase was dried, filtered, and evaporated in vacuo. The evaporation residue (1.12 gm) was recrystallized from ethanol by addition of activated charcoal.

Yield: 0.5 gm (39.4% of theory),
M.p.: 225°–227° C.

| Calc.: | C | 71.73 | H | 6.43 | N | 8.65 |
|---|---|---|---|---|---|---|
| Found: |   | 71.70 |   | 6.50 |   | 8.66 |

By use of a procedure analogous to that of Example 37, the following compound was prepared:
4-[(1-(5-Ethoxycarbonylamino-2-piperidino-phenyl)-1-ethyl)-aminocarbonylmethyl]-benzoic acid
Yield: 34.2% of theory,
M.p.: 220° C. (decomp.)

| Calc.: | C | 66.21 | H | 6.89 | N | 9.26 |
|---|---|---|---|---|---|---|
| Found: |   | 65.97 |   | 6.83 |   | 9.57 |

Example 38

4-[(1-(5-Methylsulfonylamino-2-piperidino-phenyl)-1 ethyl)-aminocarbonylmethyl]-benzoic acid A quantity of 0.20 ml (0.262 m mol) of mesyl chloride was added to a solution of 0.10 gm (0.262 m mol) of 4-[(1-(5-amino-2-piperidino-phenyl)-ethyl)-aminocarbonylmethyl]-benzoic acid in 1 ml of anhydrous pyridine. After the exothermic reaction was finished, the mixture was allowed to stand for four hours at 20° C. Subsequently the reaction mixture was evaporated in vacuo, and the evaporation residue was distributed at a pH of 2 to 3 between water and chloroform. The acidic aqueous phase was adjusted to a pH of 6 to 7 by means of sodium bicarbonate solution and extracted with chloroform. This chloroform extract was dried and filtered. The residue obtained after evaporation in vacuo was purified by column chromatography on silica gel (chloroform/methanol=4:1).

Yield: 0.03 gm (25% of theory),
M.p: 210°–220° C. (decomp.) (ether)

| Calc.: | mol peak | m/e = 459 |
|---|---|---|
| Found: |   | m/e = 459 |

Example 39

4-[(1-(5-Acetoxy-2-piperidino-phenyl)-1-ethyl)-aminocarbonylmethyl]-benzoic acid An amount of 0.35 gm (0.915 m mol) of 4-[(1-(5-hydroxy-2-piperidinophenyl)-ethyl)-aminocarbonylmethyl]-benzoic acid was heated together with 0.103 ml (1.098 m mol) of acetic anhydride on a steam bath, and after standing for four days at 20° C., the reaction mixture was recrystallized from methanol.

Yield: 0.16 gm (41.2% of theory),
M.p.: 218°–221° C.

| Calc.: | C | 67.91 | H | 6.65 | N | 6.60 |
|---|---|---|---|---|---|---|
| Found: |   | 67.70 |   | 6.95 |   | 6.55 |

Example 40

4-[(1-(5-Methoxy-2-piperidino-phenyl)-1-ethyl)-aminocarbonylmethyl]-benzoic acid methyl ester A solution of 60 mg (0.157 m mol) of 4-[(1-(5-hydroxy-2-piperidino-phenyl)-ethyl)-aminocarbonylmethyl]-benzoic acid in 1 ml of methanol (+1 drop of water) was added dropwise mixed with a etheral diazomethane solution, until no formation of gas took place. To destroy excess diazomethane, 2N acetic acid was added. After evaporation in vacuo, the evaporation residue was distributed between toluene/ether and dilute sodium hydroxide solution. After drying, filtering, and evaporating the organic phase in vacuo, the evaporation residue was purified by column chromatography on silica gel (chloroform/methanol=5:1).

Yield: 27% of theory,
M.p.: Foam

| Calc.: | mol peak | m/e = 410 |
|---|---|---|
| Found: |   | m/e = 410 |

Example 41

4-[(1-(5-Benzyloxy-2-piperidino-phenyl)-1-ethyl)-aminocarbonylmethyl]-benzoic acid ethyl ester A solution of 0.50 gm (1.218 m mol) of 4-[(1-(5-hydroxy-2-piperidino-phenyl)-ethyl)-aminocarbonylmethyl]-benzoic acid ethyl ester in 10 ml of anhydrous dimethyl formamide was quickly added dropwise to a suspension of 1.353 m mol of sodium hydride (32.5 mg of a 50% suspension of oil) in 2 ml of anhydrous dimethyl formamide. After stirring for 1.5 hours at 20° C., 0.16 ml (1.353 m mol) of benzyl bromide, dissolved in 2.3 ml of anhydrous dimethyl formamide, were added, and stirring was continued for 16 hours at 20° C. After evaporation in vacuo the residue was distributed between water and ether. The organic extract was dried, filtered, and evaporated in vacuo. The evaporation residue was purified by column chromatography on silica gel (toluene/acetone=10:1).

Yield: 0.34 gm (55.7% of theory),
M.p.: 155°–157° C. (ether)

| Calc.: | C | 74.37 | H | 7.25 | N | 5.60 |
|---|---|---|---|---|---|---|
| Found: | | 74.11 | | 7.41 | | 5.39 |

Example 42

4-[(1-(5-Aminocarbonyl-2-piperidino-phenyl-1-ethyl)-aminocarbonylmethyl]-benzoic acid ethyl ester Amounts of 3.8 gm (9.06 m mol) of 4-[(1-(5-cyano-2-piperidino-phenyl)-ethyl)-aminocarbonylmethyl]-benzoic acid ethyl ester and 38 gm of polyphosphoric acid were stirred for 2.5 hours at 80° to 90° C. Under ice-cooling water was added carefully, and the reaction mixture was layered with ethyl acetate and adjusted alkaline by means of conc. ammonia. The organic phase was washed with water, dried, and evaporated in vacuo. The evaporation residue was purified by column chromatography on silica gel (chloroform/methanol=20:1).

Yield: 1 gm (25.2% of theory),
M.p.: 188°–189° C. (ethanol)

| Calc.: | C | 68.63 | H | 7.14 | N | 9.60 |
|---|---|---|---|---|---|---|
| Found: | | 68.42 | | 6.95 | | 9.46 |

Example 43

4-[(1-(5-Ethoxycarbonyl-2-piperidino-phenyl)-1-ethyl)-aminocarbonylmethyl]-benzoic acid ethyl ester During refluxing dried hydrochloric acid was introduced into a solution of 1.1 gm (2.62 m mol) of 4-[(1-(5-cyano-2-piperidino-phenyl)-ethyl)-aminocarbonylmethyl]-benzoic acid ethyl ester in 22 ml of absolute ethanol until, after four hours, no nitrile could be detected. The reaction mixture was evaporated in vacuo, mixed with water and ether, and adjusted alkaline by means of sodium bicarbonate solution. The separated ether phase was extracted with water, dried, filtered, and evaporated in vacuo. The evaporation residue was purified by column chromatography on silica gel (methylene chloride/acetonitrile/glacial acetic acid=10:1:0.05).

Yield: 0.6 gm (49.2% of theory),
M.p.: 136°–138° C. (ether)

| Calc.: | C | 69.51 | H | 7.35 | N | 6.00 |
|---|---|---|---|---|---|---|
| Found: | | 69.28 | | 7.34 | | 5.83 |

Example 44

4-[(1-(2-(4-Oxo-piperidino)-phenyl)-1-ethyl)-aminocarbonylmethyl]-benzoic acid

A solution of 2.9 gm (6.86 m mol) of 4-[(1-(2-(1,4-dioxa-8-aza-spiro[4.5]decane-8-yl)-phenyl)-ethyl)-aminocarbonylmethyl]-benzoic acid semihydrate in 40 ml of acetone was adjusted to a pH of 2 by the addition of 2N hydrochloric acid. After stirring for six hours at 50° C., 5 drops of conc. hydrochloric acid were added, and the mixture was allowed to stand for 16 hours at 20° C. The reaction mixture was evaporated in vacuo, mixed with water and ethyl acetate, and adjusted to a pH of 6 by means of 2N ammonia. After extraction several times with ethyl acetate, the combined organic extracts were washed with water, dried, filtered, and evaporated in vacuo. The evaporation residue was recrystallized from acetone/petroleum ether.

Yield: 1.9 gm (73.1% of theory),
M.p.: 177°–180° C. (decomp.)

| Calc.: | C | 69.46 | H | 6.36 | N | 7.36 |
|---|---|---|---|---|---|---|
| Found: | | 69.75 | | 6.33 | | 7.29 |

Example 45

4-[(1-(2-(4-Hydroxy-piperidino)-phenyl)-1-ethyl)-aminocarbonylmethyl]-benzoic acid × 0.66H$_2$O An amount of 0.224 gm (5.92 m mol) of sodium borohydride was added in portions with stirring to a solution of 1 gm (2.63 m mol) of 4-[(1-(2-(4-oxo-piperidino)-phenyl)-ethyl)-aminocarbonylmethyl]-benzoic acid in 20 ml of absolute ethanol. After stirring for 1.5 hours at room temperature, the reaction mixture was adjusted acidic by means of 2N hydrochloric acid, evaporated in vacuo, mixed with water and ethyl acetate, and adjusted to a pH of 6 by means of 2N sodium hydroxide solution. After extraction several times with ethyl acetate, the organic phase was dried and filtered, and the extract was evaporated in vacuo. The evaporated in vacuo. The evaporation residue was recrystallized from petroleum ether.

Yield: 0.78 gm (75% of theory),
M.p.: 175°–180° C. (decomp.)

| Calc.: | (× 0.66 H$_2$O) | C | 66.97 | H | 6.81 | N | 7.10 |
|---|---|---|---|---|---|---|---|
| Found: | | | 66.72 | | 6.62 | | 6.98 |

Example 46

4-[(1-(2-Piperidino-phenyl-1-ethyl)-aminocarbonylmethyl]-benzoic acid propyl ester A quantity of 0.94 gm (5.80 m mol) of carbonyl diimidazole was added to a solution of 2 gm (5.46 m mol) of 4-[(1-(2-piperidino-phenyl)-ethyl)-aminocarbonylmethyl]-benzoic acid in 20 ml of absolute tetrahydrofuran, and the mixture was heated to reflux temperature for 30 minutes in the absence of moisture. Subsequently, 1.64 ml (22 m mol) of 1-propanol were added, and the reaction mixture was stirred for 18 hours at 20° C. and then heated for 8 hours to reflux temperature. After evaporation in vacuo, the evaporation residue was purified by column chromatography on silica gel (toluene/acetone=10:1).

Yield: 1.3 gm (58.3% of theory),
M.p.: 150°–151° C. (ethyl acetate)

| Calc.: | C | 73.51 | H | 7.90 | N | 6.86 |
|---|---|---|---|---|---|---|
| Found: | | 73.70 | | 7.78 | | 6.92 |

By use of procedures analogous to that of Example 46, the following compounds were prepared:

(a) 4-[(1-(2-Piperidino-phenyl)-1-ethyl)-aminocarbonylmethyl]-benozic acid isopropyl ester
Yield: 45% of theory,
M.p.: 141°–143° C. (ether)

| Calc.: | C | 73.51 | H | 7.90 | N | 6.86 |
|---|---|---|---|---|---|---|
| Found: | | 73.20 | | 7.79 | | 6.70 |

(b) 4-[(1-(2-Piperidino-phenyl)-1-ethyl)-aminocarbonylmethyl]-benzoic acid butyl ester
Yield: 49% of theory,
M.p.: 148° C. (ether/toluene)

| Calc.: | C | 73.90 | H | 8.11 | N | 6.63 |
|---|---|---|---|---|---|---|
| Found: | | 74.10 | | 7.99 | | 6.70 |

(c) 4-[(1-(5-Chloro-2-piperidino-phenyl)-1-ethyl)-aminocarbonylmethyl]-benzoic acid ethyl ester
Yield: 41% of theory,
M.p.: 130°–133° C. (ether)

| Calc.: | C | 67.21 | H | 6.81 | Cl | 8.26 | N | 6.53 |
|---|---|---|---|---|---|---|---|---|
| Found: | | 66.90 | | 6.65 | | 8.32 | | 6.67 |

(d) 4-[(1-(5-Chloro-2-piperidino-phenyl)-1-ethyl)-aminocarbonylmethyl]-benzoic acid butyl ester
Yield: 30.7% of theory,
M.p.: 115°–118° C.

| Calc.: | C | 68.33 | H | 7.27 | Cl | 7.75 | N | 6.12 |
|---|---|---|---|---|---|---|---|---|
| Found: | | 68.20 | | 7.23 | | 7.68 | | 5.95 |

(e) 4-[(1-(5-Chloro-2-piperidino-phenyl)-1-ethyl)-aminocarbonylmethyl]-benzoic acid tert.butyl ester
Yield: 1% of theory,

| Calc.: | mol peak | m/e = 456/8 |
|---|---|---|
| Found: | | m/e = 456/8 |

(f) 4-[(1-(2-Piperidino-phenyl)-1-ethyl)-aminocarbonylmethyl]-benzoic acid 2-methoxyethyl ester
Yield: 56% of theory,
M.p.: 155°–157° C. (ethyl acetate)

| Calc.: | C | 70.74 | H | 7.60 | N | 6.60 |
|---|---|---|---|---|---|---|
| Found: | | 70.55 | | 7.38 | | 6.47 |

(g) 4-[(1-(2-Piperidino-phenyl)-1-ethyl)-aminocarbonylmethyl]-benzoic acid (2,2-dimethyl-dioxolane-4-yl)-methyl ester
Yield: 30.5% of theory,
M.p.: 110°–112° C. (ether)

| Calc.: | C | 69.98 | H | 7.55 | N | 5.83 | m/e = 480 |
|---|---|---|---|---|---|---|---|
| Found: | | 69.80 | | 7.50 | | 5.76 | m/e = 480 |

(h) 4-[(1-(2-Piperidino-phenyl)-1-ethyl)-aminocarbonylmethyl]-benzoic acid benzyl ester
Yield: 73.7% of theory,
M.p.: 126°–128° C. (ethyl acetate)

| Calc.: | C | 76.28 | H | 7.06 | N | 6.14 |
|---|---|---|---|---|---|---|
| Found: | | 76.33 | | 7.20 | | 6.03 |

(i) 4-[(1-(2-Piperidino-phenyl)-1-ethyl)-aminocarbonylmethyl]-benzoic acid 2-hydroxy-ethyl ester
After addition of 10 equivalents of ethylene glycol, the reaction mixture was heated to reflux temperature for 17 hours.
Yield: 71.4% of theory,
M.p.: 128°–129° C. (ethyl acetate/ether)

| Calc.: | C | 70.21 | H | 7.36 | N | 6.82 | m/e = 410 |
|---|---|---|---|---|---|---|---|
| Found: | | 70.14 | | 7.42 | | 6.70 | m/e = 410 |

(j) 1,2-Bis-[4-[(1-(2-piperidino-phenyl)-1-ethyl)-aminocarbonylmethyl]-benzoyloxy]-ethane
After addition of 0.5 equivalents of ethylene glycol the reaction mixture was heated to reflux temperature for 17 hours.
Yield: 43.5% of theory,
M.p.: 188°–191° C. (toluene)

| Calc.: | C | 72.80 | H | 7.17 | N | 7.38 | m/e = 758 |
|---|---|---|---|---|---|---|---|
| Found: | | 72.85 | | 7.07 | | 7.37 | m/e = 758 |

(k) 4-[(1-(2-Piperidino-phenyl)-1-ethyl)-aminocarbonylmethyl]-benzoic acid 2-diethylamino-ethyl ester
Yield: 56.7% of theory,
M.p.: 99°–101° C. (petroleum ether)

| Calc.: | C | 72.23 | H | 8.44 | N | 9.03 |
|---|---|---|---|---|---|---|
| Found: | | 72.40 | | 8.37 | | 8.95 |

(l) 4-[(1-(2-Piperidino-phenyl)-1-ethyl)-aminocarbonylmethyl]-benzoic acid 2-(1,3-dimethyl-xanthine-7-yl)-ethyl ester
Absolute pyridine was used as solvent. After addition of 1 equivalent of 7-(2-hydroxy-ethyl)-theophylline and after addition of a small piece of metallic sodium, the reaction mixture was stirred for four hours in a bath of 130° C.
Yield: 40.9% of theory,
M.p.: 121°–123° C. (ether)

| Calc.: | C | 65.01 | H | 6.34 | N | 14.68 | m/e = 572 |
|---|---|---|---|---|---|---|---|
| Found: | | 64.78 | | 6.38 | | 14.90 | m/e = 572 |

Example 47

4-[(1-(2-Piperidino-phenyl)-1-ethyl)-aminocarbonylmethyl]-benzoic acid methyl ester A mixture of 2 gm (5.46 m mol) of 4-[(1-(2-piperidino-phenyl)-ethyl)-aminocarbonylmethyl]-benzoic acid, 0.53 gm of methanol, 0.38 ml of conc. sulfuric acid, and 1.65 ml of 1,2-dichloro-ethane was refluxed for 24 hours, then evaporated in vacuo, dissolved in chloroform, and extracted with dilute sodium bicarbonate solution. The organic phase was washed with water, dried, filtered, and evaporated in vacuo. The evaporation residue was purified by column chromatography on silica gel (toluene/acetone=5:1).
Yield: 0.93 gm (44.8% of theory), M.p.: 146°–147° C.

| Calc.: | C | 72.60 | H | 7.42 | N | 7.36 |
|---|---|---|---|---|---|---|
| Found: | | 72.19 | | 7.33 | | 7.01 |

Example 48

4-[(2-(2-Piperidino-phenyl)-2-propyl)-aminocarbonylmethyl]-benzoic acid ethyl ester Quantities of 0.20 gm (0.526 m mol) of 4-[(2-(2-piperidino-phenyl)-2-propyl)-aminocarbonylmethyl]-benzoic acid and 2 ml of 4N ethanolic hydrochloric acid were stirred at 20° C. After 36 hours, the reaction mixture was evaporated in vacuo, and the evaporation residue was distributed between water [at pH=8 by addition of ammonia (10%)] and ethyl acetate. The organic phase was washed with water, dried, filtered, and evaporated in vacuo. The evaporation residue was purified by column chromatography on silica gel (toluene/acetone=10:1).

Yield: 0.079 gm (36.7% of theory),
M.p.: 151°–153° C. (ether)

| Calc.: | C | 73.50 | H | 7.90 | N | 6.86 |
|---|---|---|---|---|---|---|
| Found: | | 73.40 | | 7.95 | | 6.96 |

Example 49

4-[(1-(2-Piperidino-phenyl)-1-ethyl)-aminocarbonylmethyl]-benzoic acid tert.butyl ester A mixture of 3.60 gm (17.4 m mol) of N,N'-dicyclohexylcarbodiimide, 1.9 ml (20.4 m mol) of tert-.butanol, and 0.036 gm (0.36 m mol) of copper-(I) chloride was stirred for three days at room temperature. Then, 12 ml of methylene chloride were added, and the solution thus obtained was added dropwise to a solution of 2 gm (5.46 m mol) of 4-[(1-(2-piperidino-phenyl)-ethyl)-aminocarbonylmethyl]-benzoic acid in 80 ml of methylene chloride. After stirring for 16 hours at 20° C., the resultant precipitate was filtered off and washed with methylene chloride, and the methylene chloride solution was evaporated in vacuo. The evaporation residue was purified by column chromatography on silica gel (toluene/acetone=15:1).

Yield: 0.45 gm (19.7% of theory),
M.p.: 125°–127° C. (ether)

| Calc.: | C | 73.90 | H | 8.11 | N | 6.63 |
|---|---|---|---|---|---|---|
| Found: | | 74.20 | | 8.09 | | 6.77 |

Example 50

4-[(1-(2-Piperidino-phenyl)-1-ethyl)-aminocarbonylmethyl]-benzoic acid 2-(nicotinoyloxy)-ethyl ester A solution of 0.16 gm (1.13 m mol) of nicotinic acid chloride in 5 ml of methylene chloride was quickly added dropwise to a solution of 0.45 gm (1.10 m mol) of 4-[(1-(2-piperidino-phenyl)-ethyl)-aminocarbonylmethyl]-benzoic acid (2-hydroxy-ethyl)ester and 0.16 ml (1.16 m mol) of triethylamine in 10 ml of methylene chloride. After stirring for four hours at 20° C., the reaction mixture was extracted with water and dried, and the methylene chloride solution was filtered and evaporated in vacuo. The evaporation residue was purified by column chromatography on silica gel (chloroform/acetone=3:1).

Yield: 0.34 gm (60% of theory),
M.p.: 103°–105° C. (ether)

| Calc.: | C | 69.88 | H | 6.45 | N | 8.15 |
|---|---|---|---|---|---|---|
| Found: | | 70.13 | | 6.55 | | 8.13 |

Example 51

4-[(1-(2-Piperidino-phenyl)-1-ethyl)-aminocarbonylmethyl]-benzamide

An amount of 2.3 gm (0.0142 mol) of carbonyl diimidazole was mixed with 4.76 gm (0.013 mol) of 4-[(1-(2-piperidinophenyl)-ethyl)-aminocarbonylmethyl]-benzoic acid in 60 ml of absolute pyridine, and the mixture was subsequently heated for 45 minutes to 50° C. After cooling in a carbon dioxide/methanol bath, 7 ml of liquid ammonia were added, and the mixture was heated for 20 hours to 80° C. in an autoclave. Subsequently the reaction mixture was cooled and evaporated in vacuo. The residue was dissolved in 50 ml of hot methanol, 200 ml of water were added, and the mixture was allowed to stand overnight. The crystalline precipitate was recovered by suction filtration and recrystallized from methanol by addition of activated charcoal.

Yield: 3.5 gm (73.6% of theory),
M.p.: 197°–199° C.

| Calc.: | C | 72.30 | H | 7.45 | N | 11.50 |
|---|---|---|---|---|---|---|
| Found: | | 72.30 | | 7.45 | | 11.32 |

Example 52

4-[(1-(2-Piperidino-phenyl)-1-ethyl)-aminocarbonylmethyl]-N-methylbenzamide

Two grams (5.46 m mol) of 4-[(1-(2-piperidinophenyl)-ethyl)-aminocarbonylmethyl]-benzoic acid and 0.94 gm (5.80 m mol) of carbonyl diimidazole in 20 ml of absolute pyridine were heated to reflux temperature for one hour. Subsequently, 0.41 gm (6.07 m mol) of methylamine hydrochloride were added, and the mixture was stirred for one hour at 20° C. and refluxed for two hours. After evaporation in vacuo, the residue was distributed between water and methylene chloride, and the organic extract was dried, filtered, and evaporated in vacuo. The evaporation residue was purified by column chromatography on silica gel (chloroform/methanol conc. ammonia=10:1:0.05).

Yield: 1.7 gm (82% of theory),
M.p.: 218°–220° C. (isopropanol)

| Calc.: | C | 72.77 | H | 7.70 | N | 11.07 |
|---|---|---|---|---|---|---|
| Found: | | 72.88 | | 7.67 | | 10.91 |

By use of a procedure analogous to Example 52, the following compound was prepared:

4-[(1-(2-Piperidino-phenyl)-1-ethyl)-aminocarbonylmethyl]-N,N-dimethyl-benzamide Yield: 52.5% of theory,
M.p.: 148°–150° C. (ethyl acetate)

| Calc.: | C | 73.26 | H | 7.94 | N | 10.68 |
|---|---|---|---|---|---|---|

| Found: | 73.60 | 7.85 | 10.73 |

Example 53

4-[(1-(2-Piperidino-phenyl)-1-ethyl)-aminocarbonylmethyl]-N-butyl-benzamide

An amount of 0.94 gm (5.80 m mol) of carbonyl diimidazole was added to the solution of 2 gm (5.46 m mol) of 4-[(1-(2-piperidino-phenyl)-ethyl)-aminocarbonylmethyl]-benzoic acid in 20 ml of absolute tetrahydrofuran. The mixture was heated to reflux temperature for 30 minutes, 0.44 gm (6.1 m mol) of 1-butylamine were added, and the reaction mixture was again refluxed for two hours. After evaporation in vacuo, the evaporation residue was purified by column chromatography on silica gel (chloroform/acetone=6:1).

Yield: 1.65 gm (71.7% of theory),
M.p.: 178°-181° C. (ethyl acetate)

| Calc.: | C | 74.09 | H | 8.37 | N | 9.97 |
| Found: | | 74.34 | | 8.26 | | 9.95 |

By use of a procedure analogous to that of Example 53, the following compounds were prepared:

(a) 4-[(1-(2-Piperidino-phenyl)-1-ethyl)-aminocarbonylmethyl]-benzoic acid piperidide Yield: 73.8% of theory,
M.p.: 131°-133° C. (toluene)

| Calc.: | C | 74.79 | H | 8.14 | N | 9.69 | m/e = 433 |
| Found: | | 75.13 | | 7.99 | | 9.48 | m/e = 433 |

(b) 4-[(1-(2-Piperidino-phenyl)-1-ethyl)-aminocarbonylmethyl]-benzoic acid morpholide Yield: 60.5% of theory,
M.p.: 148°-150° C. (ethyl acetate/ether)

| Calc.: | C | 71.69 | H | 7.64 | N | 9.65 |
| Found: | | 71.60 | | 7.80 | | 9.57 |

Example 54

4-[(1-(2-Piperidino-phenyl)-1-ethyl)-aminocarbonylmethyl]-benzonitrile

A quantity of 1.14 gm (6 m mol) of p-toluene-sulfonic acid chloride was added in two portions under stirring at room temperature to a mixture of 2.19 gm (6 m mol) of 4-[(1-(2-piperidino-phenyl)-ethyl)-aminocarbonylmethyl]-benzamide and 1.07 gm (13.5 m mol) of absolute pyridine. The reaction mixture was stirred for 15 minutes at 20° C. and then for two hours at 50° C. After cooling, water was added, and the mixture was adjusted alkaline by means of conc. ammonia and extracted thrice with chloroform. The combined chloroform extracts were washed with water, dried over sodium sulfate, filtered, and evaporated in vacuo. The evaporation residue was purified by column chromatography on silica gel (chloroform/ethyl acetate=4:1).

Yield: 1.15 gm (55.3% of theory),
M.p.: 155°-157° C. (ethyl acetate)

| Calc.: | C | 76.05 | H | 7.25 | N | 12.09 |
| Found: | | 76.30 | | 7.07 | | 11.90 |

Example 55

Ethyl 4-{N-[α-(4-methyl-phenyl)-2-piperidino-benzyl]-aminocarbonylmethyl}-benzoate

Amounts of 4.7 gm (18 m mol) of triphenylphosphine, 3 gm (30 m mol) of triethylamine, and 1.5 gm (15 m mol) of carbon tetrachloride were added successively to 4.2 gm (15 m mol) of α-(4-methyl-phenyl)-2-piperidino-benzylamine and 3.4 gm (16.5 m mol) of 4-ethoxycarbonyl-phenylacetic acid dissolved in 40 ml of acenitrile. The reaction mixture was stirred at 50° C. for two hours, concentrated by evaporation, and, after acidification with 6N hydrochloric acid, extracted with ethyl acetate. The acidic aqueous phase was then extracted several times with methylene chloride. The methylene chloride extracts were washed with sodium bicarbonate solution, dried over magnesium sulfate, and concentrated by evaporation. The evaporation residue was triturated with ethanol and subjected to suction filtration.

Yield: 4.55 gm (65% of theory),
M.p.: 177°-178° C.

| Calc.: | C | 76.57 | H | 7.28 | N | 5.95 |
| Found: | | 76.19 | | 7.16 | | 5.82 |

By use of procedures analogous to that of Example 55, the following compounds were prepared:

(a) Ethyl 4-{N-[α-(3-methyl-phenyl)-2-piperidino-benzyl]-aminocarbonylmethyl}-benzoate
Yield: 48% of theory,
M.p.: 159°-160° C.

| Calc.: | C | 76.57 | H | 7.28 | N | 5.95 |
| Found: | | 76.80 | | 7.35 | | 5.76 |

(b) Ethyl 4-{N-[α-2-methyl-phenyl)-2-piperidino-benzyl]-aminocarbonylmethyl}-benzoate
Yield: 35.4% of theory,
M.p.: 196°-198° C.

| Calc.: | C | 76.57 | H | 7.28 | N | 5.95 |
| Found: | | 76.65 | | 7.35 | | 5.90 |

(c) Ethyl 4-{N-[α-(4-methoxy-phenyl)-2-piperidino-benzyl]-aminocarbonylmethyl}-benzoate
Yield: 45% of theory,
M.p.: 167°-168° C.

| Calc.: | C | 74.05 | H | 7.04 | N | 5.76 |
| Found: | | 73.72 | | 6.99 | | 5.62 |

(d) Ethyl 4-{N-[α-(4-benzyloxy-phenyl)-2-piperidino-benzyl]-aminocarbonylmethyl}-benzoate
Yield: 96% of theory,
M.p.: 154°-155° C.

| Calc.: | C | 76.84 | H | 6.81 | N | 4.98 |
|---|---|---|---|---|---|---|
| Found: | | 76.68 | | 6.68 | | 5.03 |

(e) Ethyl 4-{N-[α-(4-fluoro-phenyl)-2-piperidino-benzyl]-aminocarbonylmethyl}-benzoate
Yield: 58% of theory,
M.p.: 174°–176° C.

| Calc.: | C | 73.40 | H | 6.58 | N | 5.90 |
|---|---|---|---|---|---|---|
| Found: | | 73.55 | | 6.72 | | 5.91 |

(f) Ethyl 4-{N-[α-[2-fluoro-phenyl)-2-piperidino-benzyl]-aminocarbonylmethyl}-benzoate
Yield: 83% of theory,
M.p.: 173°–175° C.

| Calc. | C | 73.40 | H | 6.58 | N | 5.90 |
|---|---|---|---|---|---|---|
| Found: | | 73.61 | | 6.62 | | 5.85 |

(g) Ethyl 4-{N-[α-(4-chloro-phenyl)-2-piperidino-benzyl]-aminocarbonylmethyl}-benzoate
Yield: 57% of theory,
M.p.: 178°–181° C.

| Calc.: | C | 70.94 | H | 6.36 | N | 5.71 | C | 7.22 |
|---|---|---|---|---|---|---|---|---|
| Found: | | 71.10 | | 6.56 | | 5.26 | | 7.11 |

(h) Ethyl 4-{N-[α-(3-chloro-phenyl)-2-piperidino-benzyl]-aminocarbonylmethyl}-benzoate
Yield: 71% of theory,
M.p.: 153°–156° C.

| Calc.: | C | 70.94 | H | 6.36 | N | 5.71 | Cl | 7.22 |
|---|---|---|---|---|---|---|---|---|
| Found: | | 70.86 | | 6.26 | | 5.65 | | 7.25 |

(i) Ethyl 4-{N-[α-(2-chloro-phenyl)-2-piperidino-benzyl]-aminocarbonylmethyl}-benzoate
Yield: 66% of theory,
M.p.: 196°–198° C.

| Calc.: | C | 70.94 | H | 6.36 | N | 5.71 | Cl | 7.22 |
|---|---|---|---|---|---|---|---|---|
| Found: | | 70.90 | | 6.30 | | 5.61 | | 7.10 |

(k) Ethyl 4-{N-[α-(4-methylmercapto-phenyl)-2-piperidinobenzyl]-aminocarbonylmethyl}-benzoate
Yield: 84% of theory,
M.p.: 173°–175° C.

| Calc.: | C | 71.68 | H | 6.82 | N | 5.57 | Cl | 6.38 |
|---|---|---|---|---|---|---|---|---|
| Found: | | 71.92 | | 6.97 | | 5.45 | | 6.21 |

(l) Ethyl 4-{N-[5-chloro-α-(2-chloro-phenyl)-2-piperidinobenzyl]-aminocarbonylmethyl}-benzoate
Yield: 92% of theory,
M.p.: 213°–215° C.

| Calc.: | C | 66.28 | H | 5.75 | N | 5.33 | Cl | 13.49 |
|---|---|---|---|---|---|---|---|---|
| Found: | | 66.45 | | 5.86 | | 5.25 | | 13.51 |

(m) Ethyl 4-{N-[2-piperidino-α-(2-pyridyl)-benzyl]-aminocarbonylmethyl}-benzoate
Yield: 51% of theory,
M.p.: 158°–159° C.

| Calc.: | C | 73.50 | H | 6.83 | N | 9.18 |
|---|---|---|---|---|---|---|
| Found: | | 73.40 | | 6.95 | | 9.10 |

(n) Ethyl 4-{N-[2-piperidino-α-(3-pyridyl)-benzyl]-aminocarbonylmethyl}-benzoate
Yield: 85% of theory,
M.p.: 172° C.

| Calc.: | C | 73.50 | H | 6.83 | N | 9.18 |
|---|---|---|---|---|---|---|
| Found: | | 73.42 | | 6.76 | | 9.25 |

(o) Ethyl 4-{N-[2-piperidino-α-(4-pyridyl)-benzyl]-aminocarbonylmethyl}-benzoate
Yield: 20% of theory,
M.p.: 150°–152° C.

| Calc.: | C | 73.50 | H | 6.83 | N | 9.18 |
|---|---|---|---|---|---|---|
| Found: | | 73.61 | | 6.91 | | 9.15 |

(p) Ethyl 4-[N-(6-chloro-α-phenyl-2-piperidino-benzyl)-aminocarbonylmethyl]-benzoate
Yield: 12% of theory,
M.p.: Oil

| Calc.: | molecular-ion peak m/e = 490/492 |
|---|---|
| Found: | molecular-ion peak m/e = 490/492 |

(q) Ethyl 4-[N-(4-chloro-α-phenyl-2-piperidino-benzyl)-aminocarbonylmethyl]-benzoate
Yield: 37% of theory,
M.p.: 148°–150° C.

| Calc.: | C | 70.94 | H | 6.36 | N | 5.71 | Cl | 7.22 |
|---|---|---|---|---|---|---|---|---|
| Found: | | 70.81 | | 6.25 | | 5.61 | | 7.12 |

(r) Ethyl 4-[N-(3-chloro-α-phenyl-2-piperidino-benzyl)-aminocarbonylmethyl]-benzoate
Yield: 74% of theory,
M.p.: 176°–178° C.

| Calc.: | C | 70.94 | H | 6.36 | N | 5.71 | Cl | 7.22 |
|---|---|---|---|---|---|---|---|---|
| Found: | | 70.59 | | 6.25 | | 5.68 | | 7.16 |

(s) Ethyl 4-[N-(6-methyl-α-phenyl-2-piperidino-benzyl)-aminocarbonylmethyl]-benzoate
Yield: 65% of theory,
M.p.: Oil

| Calc.: | molecular-ion peak m/e = 470 |
|---|---|
| Found: | molecular-ion peak m/e = 470 |

(t) Ethyl 4-[N-(5-methyl-α-phenyl-2-piperidino-benzyl)-aminocarbonylmethyl]-benzoate
Yield: 48% of theory,
M.p.: 171°–173° C.

| Calc.: | C | 76.57 | H | 7.28 | N | 5.95 |
|---|---|---|---|---|---|---|
| Found: | | 76.75 | | 7.35 | | 5.72 |

(u) Ethyl 4-[N-(4-methyl-α-phenyl-2-piperidino-benzyl)-aminocarbonylmethyl]-benzoate
Yield: 76% of theory,
M.p.: 133°–135° C.

| Calc.: | C | 76.57 | H | 7.28 | N | 5.95 |
|---|---|---|---|---|---|---|
| Found: | | 76.51 | | 7.16 | | 5.83 |

(v) Ethyl 4-[N-(5-methoxy-α-phenyl-2-piperidino-benzyl)-aminocarbonylmethyl]-benzoate
Yield: 10% of theory,
M.p.: 122°–125° C.

| Calc.: | molecular-ion peak m/e = 486 |
|---|---|
| Found: | molecular-ion peak m/e = 486 |

(w) Ethyl 4-[N-(6-methoxy-α-phenyl-2-piperidino-benzyl)-aminocarbonylmethyl]-benzoate
Yield: 97% of theory,
M.p.: Oil

| Calc.: | molecular-ion peak m/e = 486 |
|---|---|
| Found: | molecular-ion peak m/e = 486 |

(x) Ethyl 3-chloro-4-[N-(α-phenyl-2-piperidino-benzyl)-aminocarbonylmethyl]-benzoate
Yield: 42% of theory,
M.p.: 175°–176° C.

| Calc.: | C | 70.93 | H | 6.36 | N | 5.71 | Cl | 7.22 |
|---|---|---|---|---|---|---|---|---|
| Found: | | 70.65 | | 6.36 | | 5.50 | | 7.29 |

(y) Ethyl 4-[N-(2-dimethylamino-α-phenyl-benzyl)-aminocarbonylmethyl]-benzoate
Yield: 67% of theory,
M.p.: 116°–118° C.

| Calc.: | C | 74.97 | H | 6.77 | N | 6.73 |
|---|---|---|---|---|---|---|
| Found: | | 75.13 | | 6.60 | | 6.78 |

(z) Ethyl 4-[N-(2-di-n-propylamino-α-phenyl-benzyl)-aminocarbonylmethyl]-benzoate
Yield: 76% of theory,
M.p.: 138°–139° C.

| Calc.: | C | 76.24 | H | 7.68 | N | 5.93 |
|---|---|---|---|---|---|---|
| Found: | | 76.41 | | 7.79 | | 5.81 |

(aa) Ethyl 4-{N-[2-(octahydro-1H-azonino)-α-phenyl-benzyl]aminocarbonylmethyl}-benzoate
Yield: 71% of theory,
M.p.: Oil

| Calc.: | molecular-ion peak m/e = 498 |
|---|---|
| Found: | molecular-ion peak m/e = 498 |

(bb) Ethyl 4-{N-[5-chloro-2-(2-methyl-piperidino)-α-phenylbenzyl]-aminocarbonylmethyl}-benzoate
Yield: 36.5% of theory,
M.p.: 171°–173° C.

| Calc.: | C | 71.24 | H | 6.58 | N | 5.54 | Cl | 7.01 |
|---|---|---|---|---|---|---|---|---|
| Found: | | 71.45 | | 6.68 | | 5.59 | | 7.20 |

(cc) Ethyl 4-{N-[2-(3,3-dimethyl-piperidino)-α-phenyl-benzyl]-aminocarbonylmethyl}-benzoate
Yield: 91% of theory,
M.p.: 146°–148° C.

| Calc.: | C | 76.82 | H | 7.49 | N | 5.78 |
|---|---|---|---|---|---|---|
| Found: | | 76.91 | | 7.55 | | 5.61 |

Example 56

Ethyl 4-{N-[α-(4-chloro-phenyl)-2-piperidino-benzyl]-aminocarbonylmethyl}-benzoate A solution of 5 gm (22.1 m mol) of 4-ethoxycarbonyl-phenylacetyl chloride in 20 ml of chloroform was added dropwise, under cooling with ice, to a solution of 6.02 gm (20 m mol) of α-(4-chloro-phenyl)-2-piperidino-benzylamine and 3.5 ml (25 m mol) of triethylamine in 50 ml of chloroform. The mixture was stirred for two hours at ambient temperature, added to water, and extracted with chloroform. The extracts were dried and concentrated by evaporation. The evaporation residue was chromatographed on silica gel by use of toluene/ethyl acetate (5:1) as eluant.
Yield: 5.6 gm (57% of theory),
M.p.: 178°–181° C.

| Calc.: | C | 70.94 | H | 6.36 | N | 5.71 | Cl | 7.22 |
|---|---|---|---|---|---|---|---|---|
| Found: | | 71.09 | | 6.47 | | 5.61 | | 7.10 |

By use of a procedure analogous to that of Example 56, the following compound was prepared:
Ethyl 4-{N-[5-chloro-2-(3-methyl-piperidino)-α-phenylbenzyl]-aminocarbonylmethyl}-benzoate
Yield: 54% of theory,
M.p.: 178°–180° C.

| Calc.: | C | 71.24 | H | 6.58 | N | 5.54 | Cl | 7.01 |
|---|---|---|---|---|---|---|---|---|
| Found: | | 70.91 | | 6.64 | | 5.75 | | 7.01 |

Example 57

4-[N-α-(4-Methyl-phenyl)-2-piperidino-benzyl]-aminocarbonylmethyl]-benzoic acid

A quantity of 4.4 gm (9.35 m mol) of ethyl 4-{N-[α-(4-methyl-phenyl)-2-piperidino-benzyl]-aminocarbonylmethyl}-benzoate was dissolved in 150 ml of ethanol, with heating. Then, 20 ml of 1N sodium hydroxide solution were added, and the mixture was stirred for three hours at 50° C. Twenty milliliters of 1N hydrochloric acid were then added to the reaction mixture, and any excess ethanol was eliminated by evaporation in a rotary evaporator. The remaining aqueous suspension was filtered, and the precipitate was thoroughly washed with water. The precipitate was subsequently recrystallized from acetonitrile.

Yield: 2.45 gm (59.3% of theory),
M.p.: 226°–228° C.

| Calc.: | C | 75.99 | H | 6.83 | N | 6.33 |
|---|---|---|---|---|---|---|
| Found: | | 75.60 | | 6.75 | | 6.29 |

By use of procedures analogous to that of Example 57, the following compounds were prepared:

(a) 4-{N-[α-(3-Methyl-phenyl)-2-piperidino-benzyl]-aminocarbonylmethyl}-benzoic acid Yield: 72% of theory,
M.p.: 202°–203° C.

| Calc.: | C | 75.99 | H | 6.83 | N | 6.33 |
|---|---|---|---|---|---|---|
| Found: | | 75.64 | | 6.91 | | 6.37 |

(b) 4-{N-[α-(2-Methyl-phenyl)-2-piperidino-benzyl]-aminocarbonylmethyl}-benzoic acid
Yield: 42.6% of theory,
M.p.: 285°–290° C.

| Calc.: | C | 75.99 | H | 6.83 | N | 6.33 |
|---|---|---|---|---|---|---|
| Found: | | 76.05 | | 6.98 | | 6.25 |

(c) 4-{N-[α-(4-Methoxy-phenyl)-2-piperidino-benzyl]-aminocarbonylmethyl}-benzoic acid
Yield: 72.4% of theory,
M.p.: 228°–230° C.

| Calc.: | C | 73.34 | H | 6.59 | N | 6.11 |
|---|---|---|---|---|---|---|
| Found: | | 73.22 | | 6.61 | | 6.13 |

(d) 4-{N-[α-(4-Benzyloxy-phenyl)-2-piperidino-benzyl]-aminocarbonylmethyl}-benzoic acid
Yield: 57% of theory,
M.p.: 219°–221° C.

| Calc.: | C | 76.38 | H | 6.41 | N | 5.24 |
|---|---|---|---|---|---|---|
| Found: | | 76.05 | | 6.44 | | 5.24 |

(e) 4-{N-[α-(4-Fluoro-phenyl)-2-piperidino-benzyl]-aminocarbonylmethyl}-benzoic acid
Yield: 75% of theory,
M.p.: 238°–240° C.

| Calc.: | C | 72.63 | H | 6.09 | N | 6.27 |
|---|---|---|---|---|---|---|
| Found: | | 72.98 | | 6.29 | | 6.32 |

(f) 4-{N-[α-(2-Fluoro-phenyl)-2-piperidino-benzyl]-aminocarbonylmethyl}-benzoic acid
Yield: 87% of theory,
M.p.: 280°–283° C.

| Calc.: | C | 72.63 | H | 6.09 | N | 6.27 |
|---|---|---|---|---|---|---|
| Found: | | 72.70 | | 6.10 | | 6.37 |

(g) 4-{N-[α-(4-Chloro-phenyl)-2-piperidino-benzyl]-aminocarbonylmethyl}-benzoic acid
Yield: 89% of theory,
M.p.: 241°–242° C.

| Calc.: | C | 70.05 | H | 5.88 | N | 6.05 | Cl | 7.66 |
|---|---|---|---|---|---|---|---|---|
| Found: | | 69.74 | | 6.05 | | 5.01 | | 7.64 |

(h) 4-{N-[α-(3-Chloro-phenyl)-2-piperidino-benzyl]-aminocarbonylmethyl}-benzoic acid
Yield: 53% of theory,
M.p.: 223°–225° C.

| Calc.: | C | 70.05 | H | 5.88 | N | 6.05 | Cl | 7.66 |
|---|---|---|---|---|---|---|---|---|
| Found: | | 70.28 | | 5.98 | | 5.78 | | 7.84 |

(i) 4-{N-[α-(2-Chloro-phenyl)-2-piperidino-benzyl]-aminocarbonylmethyl}-benzoic acid
Yield: 98% of theory,
M.p.: 303°–305° C.

| Calc.: | C | 70.05 | H | 5.88 | N | 6.05 | Cl | 7.66 |
|---|---|---|---|---|---|---|---|---|
| Found: | | 69.88 | | 6.05 | | 5.87 | | 7.74 |

(k) 4-{N-[α-(4-Methylmercapto-phenyl)-2-piperidino-benzyl]-aminocarbonylmethyl}-benzoic acid
Yield: 84.6% of theory,
M.p.: 225°–227° C.

| Calc.: | C | 70.86 | H | 6.37 | N | 5.90 | Cl | 6.75 |
|---|---|---|---|---|---|---|---|---|
| Found: | | 70.34 | | 6.37 | | 5.68 | | 6.82 |

(l) 4-{N-[5-Chloro-α-(2-chloro-phenyl)-2-piperidino-benzyl]-aminocarbonylmethyl}-benzoic acid
Yield: 90% of theory,
M.p.: 317°–320° C.

| Calc.: | C | 65.19 | H | 5.27 | N | 5.63 | Cl | 14.25 |
|---|---|---|---|---|---|---|---|---|
| Found: | | 64.87 | | 5.34 | | 5.69 | | 14.22 |

(m) 4-{N-[2-Piperidino-α-(2-pyridyl)-benzyl]-aminocarbonylmethyl}-benzoic acid
Yield: 81% of theory,
M.p.: 160°–161° C.

| Calc.: | C | 72.71 | H | 6.34 | N | 9.78 |
|---|---|---|---|---|---|---|
| Found: | | 72.43 | | 6.39 | | 10.00 |

(n) 4-{N-[2-Piperidino-α-(3-pyridyl)-benzyl]-aminocarbonylmethyl}-benzoic acid
Yield: 72% of theory,
M.p.: 252°–253° C.

| Calc.: | C | 72.71 | H | 6.34 | N | 9.78 |
|---|---|---|---|---|---|---|
| Found: | | 72.56 | | 6.53 | | 9.60 |

(o) 4-{N-[2-Piperidino-α-(4-pyridyl)-benzyl]-aminocarbonylmethyl}-benzoic acid
Yield: 68.5% of theory,
M.p.: from 260° C. (decomp.)

| Calc.: | C | 72.71 | H | 6.34 | N | 9.78 |
|---|---|---|---|---|---|---|
| Found: | | 72.31 | | 6.29 | | 9.63 |

(p) 4-[N-(6-Chloro-α-phenyl-2-piperidino-benzyl)-aminocarbonylmethyl]-benzoic acid
Yield: 82% of theory,
M.p.: 91°–94° C.

| Calc.: | C | 70.04 | H | 5.88 | N | 6.05 | Cl | 7.66 |
|---|---|---|---|---|---|---|---|---|
| Found: | | 69.61 | | 5.77 | | 5.96 | | 7.78 |

(q) 4-[N-(4-Chloro-α-phenyl-2-piperidino-benzyl)-aminocarbonylmethyl]-benzoic acid
Yield: 61% of theory,
M.p.: 221°–223° C.

| Calc.: | C | 70.05 | H | 5.88 | N | 6.05 | Cl | 7.66 |
|---|---|---|---|---|---|---|---|---|
| Found: | | 69.73 | | 5.89 | | 5.87 | | 7.52 |

(r) 4-[N-(3-Chloro-α-phenyl-2-piperidino-benzyl)-aminocarbonylmethyl]-benzoic acid
Yield: 83% of theory,
M.p.: 210°–213° C.

| Calc.: | C | 70.05 | H | 5.88 | N | 6.05 | Cl | 7.66 |
|---|---|---|---|---|---|---|---|---|
| Found: | | 70.31 | | 6.03 | | 5.90 | | 7.79 |

(s) 4-[N-(6-Methyl-α-phenyl-2-piperidino-benzyl)-aminocarbonylmethyl]-benzoic acid
Yield: 64% of theory,
M.p.: 165°–170° C. (sintering from 150° C.)

| Calc.: | C | 75.99 | H | 6.83 | N | 6.33 |
|---|---|---|---|---|---|---|
| Found: | | 75.73 | | 6.96 | | 6.14 |

(t) 4-[N-(5-Methyl-α-phenyl-2-piperidino-benzyl)-aminocarbonylmethyl]-benzoic acid
Yield: 97% of theory,
M.p.: 243°–245° C.

| Calc.: | C | 75.99 | H | 6.83 | N | 6.33 |
|---|---|---|---|---|---|---|
| Found: | | 75.60 | | 7.01 | | 6.31 |

(u) 4-[N-(4-Methyl-α-phenyl-2-piperidino-benzyl)-aminocarbonylmethyl]-benzoic acid
Yield: 96% of theory,
M.p.: 202°–203° C.

| Calc.: | C | 75.99 | H | 6.83 | N | 6.33 |
|---|---|---|---|---|---|---|
| Found: | | 76.04 | | 6.78 | | 6.23 |

(v) 4-[N-(5-Methoxy-α-phenyl-2-piperidino-benzyl)-aminocarbonylmethyl]-benzoic acid
Yield: 27% of theory,
M.p.: 217°–220° C. (sintering from 203° C.)

| Calc.: | C | 73.34 | H | 6.59 | N | 6.11 |
|---|---|---|---|---|---|---|
| Found: | | 72.92 | | 6.68 | | 5.99 |

(w) 4-[N-(6-Methoxy-α-phenyl-2-piperidino-benzyl)-aminocarbonylmethyl]-benzoic acid
Yield: 51.5% of theory,
90°–95° C.

| Calc.: | C | 73.34 | H | 6.59 | N | 6.11 |
|---|---|---|---|---|---|---|
| Found: | | 73.03 | | 6.42 | | 5.86 |

(x) 4-{N-[5-Chloro-2-(3,5-cis-dimethyl-piperidino)-α-phenyl-benzyl]-aminocarbonylmethyl}-benzoic acid
Yield: 81% of theory,
M.p.: 253°–255° C.

| Calc.: | C | 70.93 | H | 6.36 | N | 5.71 | Cl | 7.22 |
|---|---|---|---|---|---|---|---|---|
| Found: | | 70.68 | | 6.51 | | 5.73 | | 7.36 |

(y) 4-[N-(2-Dimethylamino-α-phenyl-benzyl)-aminocarbonylmethyl]-benzoic acid
Yield: 83% of theory,
M.p.: 183°–184° C.

| Calc.: | C | 74.20 | H | 6.23 | N | 7.21 |
|---|---|---|---|---|---|---|
| Found: | | 74.31 | | 6.27 | | 7.16 |

(z) 4-[N-(2-Di-n-propylamino-α-phenyl-benzyl)-aminocarbonylmethyl]-benzoic acid
Yield: 79% of theory,
M.p.: 202°–204° C.

| Calc.: | C | 75.64 | H | 7.26 | N | 6.30 |
|---|---|---|---|---|---|---|
| Found: | | 75.74 | | 7.31 | | 6.15 |

(aa) 4-{N-[5-Chloro-2-(2-methyl-piperidino)-α-phenyl-benzyl]-aminocarbonylmethyl}-benzoic acid
Yield: 52% of theory,
M.p.: 280°–282° C.

| Calc.: | C | 70.50 | H | 6.13 | N | 5.87 | Cl | 7.43 |
|---|---|---|---|---|---|---|---|---|
| Found: | | 70.14 | | 6.10 | | 5.75 | | 7.45 |

(bb) 4-{N-[5-Chloro-2-(3-methyl-piperidino)-α-phenyl-benzyl]-aminocarbonylmethyl}-benzoic acid
Yield: 66% of theory,
M.p.: 246°–248° C.

| Calc.: | C | 70.50 | H | 6.13 | N | 5.87 | Cl | 7.43 |
|---|---|---|---|---|---|---|---|---|
| Found: | | 70.16 | | 6.07 | | 5.87 | | 7.30 |

(cc) 4-{N-[2-(3,3-Dimethyl-piperidino)-α-phenyl-benzyl]-aminocarbonylmethyl}-benzoic acid
Yield: 59% of theory,
M.p.: 238°–240° C.

| Calc.: | C | 76.28 | H | 7.07 | N | 6.14 |
|---|---|---|---|---|---|---|
| Found: | | 76.38 | | 7.28 | | 6.11 |

(dd) 3-Chloro-4-[N-(α-phenyl-2-piperidino-benzyl)-aminocarbonylmethyl]-benzoic acid
Yield: 56% of theory,
M.p.: 236°–239° C.

| Calc.: | C | 70.04 | H | 5.88 | N | 6.05 | Cl | 7.66 |
|---|---|---|---|---|---|---|---|---|
| Found: | | 69.88 | | 5.77 | | 5.86 | | 7.81 |

(ee) 4-{N-[2-(3,5-Cis-dimethyl-piperidino)-5-nitro-α-phenyl-benzyl]-aminocarbonylmethyl}-benzoic acid
Yield: 81% of theory,
M.p.: from 255° C. (decomp.)

| Calc.: | C | 69.44 | H | 6.23 | N | 8.38 |
|---|---|---|---|---|---|---|
| Found: | | 68.95 | | 6.44 | | 8.53 |

(ff) 4-{N-[2-(Octahydro-1H-azonino)-α-phenyl-benzyl]-aminocarbonylmethyl}-benzoic acid
Yield: 62.5% of theory,
M.p.: 235°–237° C.

| Calc.: | C | 76.56 | H | 7.28 | N | 5.95 |
|---|---|---|---|---|---|---|
| Found: | | 76.50 | | 7.30 | | 5.94 |

(gg) 4-[N-(5-Hydroxy-α-phenyl-2-piperidino-benzyl)-aminocarbonylmethyl]-benzoic acid
Yield: 71% of theory,
M.p.: 98°–101° C.

| Calc.: | C | 72.95 | H | 6.35 | N | 6.30 |
|---|---|---|---|---|---|---|
| Found: | | 72.98 | | 6.40 | | 6.47 |

Example 58

4-{N-[α-(4-Hydroxy-phenyl)-2-piperidino-benzyl]-aminocarbonylmethyl}-benzoic acid An amount of 1.1 gm (2 m mol) of 4-{N-[α-(4-benzyloxyphenyl)-2-piperidino-benzyl]-aminocarbonylmethyl}-benzoic acid was suspended in 200 ml of ethanol and catalytically debenzylated at 50° C., under a hydrogen pressure of 5 bar, in the presence of 0.4 gm of 10% palladium/charcoal. Then, the catalyst was filtered off, and the filtrate was concentrated by evaporation and recrystallized from acetonitrile.
Yield: 720 mg (66.7% of theory),
M.p.: 202°–204° C.

| Calc.: | C | 72.95 | H | 6.35 | N | 6.30 |
|---|---|---|---|---|---|---|
| Found: | | 72.65 | | 6.17 | | 6.20 |

By use of a procedure analogous to that of Example 58, the following compound was prepared:
Ethyl 4-[N-(5-hydroxy-α-phenyl-2-piperidino-benzyl)-aminocarbonylmethyl]-benzoate
Yield: 93% of theory,
M.p.: 191°–193° C.

| Calc.: | C | 73.70 | H | 6.82 | N | 5.93 |
|---|---|---|---|---|---|---|
| Found: | | 73.52 | | 6.57 | | 5.61 |

Example 59

4-{N-[α-(4-Methyl-phenyl)-2-piperidino-benzyl]-aminocarbonylmethyl}-benzyl alcohol Two and one-half grams (5.3 m mol) of ethyl 4-{N-[α-(4-methyl-phenyl)-2-piperidino-benzyl]-aminocarbonylmethyl}-benzoate were added in batches to a suspension of 0.5 gm (13.2 m mol) of lithium aluminium hydride in 50 ml of absolute tetrahydrofuran. The mixture was stirred for a further 30 minutes at ambient temperature, decomposed by the dropwise addition of 4N sodium hydroxide solution, and filtered to remove the sodium aluminate formed. The filtrate was concentrated by evaporation, and the residue was recrystallized from a small amount of toluene.
Yield: 0.98 gm (43% of theory),
M.p.: 144°–146° C.

| Calc.: | C | 78.47 | H | 7.53 | N | 6.54 |
|---|---|---|---|---|---|---|
| Found: | | 78.20 | | 7.39 | | 6.58 |

By use of a procedure analogous to that of Example 59, the following compound was prepared:
4-{N-[α-Phenyl-2-piperidino-benzyl)-aminocarbonylmethyl]-benzyl alcohol
Yield: 31.5% of theory,
M.p.: 143°–145° C.

| Calc.: | C | 78.23 | H | 7.29 | N | 6.76 |
|---|---|---|---|---|---|---|
| Found: | | 78.13 | | 7.30 | | 6.62 |

Example 60

4-{N-[α-(4-Methyl-phenyl)-2-piperidino-benzyl]-aminocarbonylmethyl}-benzaldehyde Quantities of 8.85 gm (20 m mol) of 4-{N-[α-(4-Methylphenyl)-2-piperidino-benzyl]-aminocarbonylmethyl}-benzoic acid and 3.25 gm (20 m mol) of N,N'-carbonyldiimidazole were refluxed in 100 ml of absolute tetrahydrofuran for two hours. Then, the mixture was concentrated by evaporation, and, after addition of 50 ml of pyridine and 3.7 gm (20 m mol) of 4-toluene-sulphonic acid hydrazide, the mixture was refluxed for a further two hours. The mixture was then poured onto ice water and subjected to suction filtration, and the precipitate was dried. The resulting crude toluene-sulphonic acid hydrazide of the carboxylic acid used was mixed with 20 gm of anhydrous sodium carbonate and heated to 170° C. in 50 ml of ethylene glycol for two hours. Then, it was added to water and extracted with chloroform. The concentrated extracts were purified by column chromatography on silica gel by use of toluene-/ethyl acetate (5:1) as eluant.
Yield: 1.73 gm (21% of theory),
M.p.: 144°–146° C.

| Calc.: | C | 78.84 | H | 7.09 | N | 6.57 |
|---|---|---|---|---|---|---|
| Found: | | 78.95 | | 7.19 | | 6.50 |

By use of a procedure analogous to that of Example 60, the following compound was prepared:
4-{N-[α-Phenyl-2-piperidino-benzyl)-aminocarbonylmethyl}-benzaldehyde
Yield: 29% of theory,
M.p.: 168°–170° C.

| Calc.: | C | 78.61 | H | 6.84 | N | 6.79 |
|---|---|---|---|---|---|---|
| Found: | | 78.60 | | 7.00 | | 6.72 |

Example 61

4-{N-[α-(4-Methyl-phenyl)-2-piperidino-benzyl]-aminocarbonylmethyl}-benzaldehyde One-half gram (1.2 m mol) of 4-{N-[α-(4-methyl-phenyl)-2-piperidino-benzyl]-aminocarbonylmethyl}- benzyl alcohol was added to a suspension of 0.4 gm (1.5 m mol) of pyridinium chlorochromate in 2 ml of chloroform. After 12 hours at ambient temperature, ether was added, the mixture was filtered, and the concentrated filtrate was purified by column chromatography on silica gel [eluant: toluene/ethyl acetate (5:1)].
Yield: 0.3 gm (60% of theory),
M.p.: 145°–146° C.

| Calc.: | C | 78.84 | H | 7.09 | N | 6.57 |
|---|---|---|---|---|---|---|
| Found: | | 78.97 | | 7.12 | | 6.57 |

By use of a procedure analogous to that of Example 61, the following compound was prepared:
4-[N-(α-Phenyl-2-piperidino-benzyl)-aminocarbonyl-methyl]-benzaldehyde
Yield: 40% of theory,
M.p.: 170° C.

| Calc.: | C | 78.61 | H | 6.84 | N | 6.79 |
|---|---|---|---|---|---|---|
| Found: | | 78.59 | | 6.87 | | 6.61 |

Example 62

Ethyl 4-{N-[α-(4-methyl-phenyl)-2-piperidino-benzyl]-aminocarbonyl-methyl}-cinnamate Four hundred twenty-seven milligrams (1 m mol) of 4-{N-[α-(4-methyl-phenyl)-2-piperidino-benzyl]-aminocarbonylmethyl}-benzaldehyde were added to an ethereal solution of 450 mg (2 m mol) of ethyl diethylphosphonoacetate and 100 mg (2 m mol) of 50% sodium hydride. After the mixture had been stirred overnight, water was added, and the resulting mixture was extracted with chloroform and purified by column chromatography on silica gel by use of toluene/ethyl acetate (5:1) as eluant.
Yield: 0.18 gm (36% of theory),
M.p.: 176°–180° C.

| Calc.: | C | 77.39 | H | 7.31 | N | 5.64 |
|---|---|---|---|---|---|---|
| Found: | | 77.64 | | 7.25 | | 5.71 |

By use of a procedure analogous to that of Example 62, the following compound was prepared:
Ethyl 4-[N-(α-phenyl-2-piperidino-benzyl)-aminocarbonylmethyl]-cinnamate
Yield: 28.6% of theory,
M.p.: 159°–161° C.

| Calc.: | C | 77.14 | H | 7.10 | N | 5.80 |
|---|---|---|---|---|---|---|
| Found: | | 77.28 | | 7.21 | | 5.65 |

Example 63

4-{N-[α-(4-Methyl-phenyl)-2-piperidino-benzyl]-aminocarbonylmethyl}-cinnamic acid Prepared by alkaline saponification of ethyl 4-{N-[α-(4-methyl-phenyl)-2-piperidino-benzyl]-aminocarbonyl-methyl}-cinnamate analogously to Example 57.
Yield: 84% of theory,
M.p.: 173°–176° C.

| Calc.: | C | 76.90 | H | 6.88 | N | 5.98 |
|---|---|---|---|---|---|---|
| Found: | | 77.24 | | 7.01 | | 5.64 |

By use of a procedure analogous to that of Example 63, the following compound was prepared:
4-[N-(α-Phenyl-2-piperidino-benzyl)-aminocarbonyl-methyl]-cinnamic acid
Yield: 75% of theory,
M.p.: 177°–180° C.

| Calc.: | C | 76.62 | H | 6.65 | N | 6.16 |
|---|---|---|---|---|---|---|
| Found: | | 76.75 | | 6.57 | | 6.07 |

Example 64

Ethyl 4-{N-[α-[3-methyl-phenyl)-2-piperidino-benzyl]-aminocarbonylmethyl}-benzoate A mixture of 0.22 gm (0.8 m mol) of α-(3-methyl-phenyl)-2-piperidino-benzyl alcohol and 0.15 gm (0.8 m mol) of ethyl 4-cyanomethyl-benzoate in 2 ml of o-dichlorobenzene was added dropwise, at ambient temperature, to 1.5 ml of o-dichlorobenzene and 1.5 ml of concentrated sulfuric acid. After stirring for two hours, the mixture was poured onto ice water, extracted once with ether, made alkaline with dilute sodium hydroxide solution, and extracted with chloroform. The chloroform extract was concentrated by evaporation, and the residue was recrystallized from ethanol.
Yield: 0.22 gm (60% of theory),
M.p.: 158°–159° C.

| Calc.: | C | 76.57 | H | 7.28 | N | 5.95 |
|---|---|---|---|---|---|---|
| Found: | | 76.41 | | 7.39 | | 5.76 |

By use of a procedure analogous to that of Example 64, the following compound was prepared:
Ethyl 4{N-[2-(3,5-cis-dimethyl-piperidino)-5-nitro-α-phenyl-benzyl]-aminocarbonylmethyl}-benzoate
Yield: 57% of theory,
M.p.: 170°–173° C.

| Calc.: | C | 70.30 | H | 6.66 | N | 7.93 |
|---|---|---|---|---|---|---|
| Found: | | 70.05 | | 6.68 | | 7.81 |

Example 65

4-{N-[α-(4-Methyl-phenyl)-2-piperidino-benzyl]-aminocarbonylmethyl}-benzoic acid Two hundred forty milligrams (5 m mol) of 4-{N-[5-chloro-α-(4-methyl-phenyl)-2-piperidino-benzyl]-aminocarbonylmethyl}-benzoic acid were catalytically dehalogenated in 80 ml of ethanol/dioxane (1:1) in the presence of 0.1 gm of 10% palladium on charcoal at 50° C. and under a hydrogen pressure of 5 bar. After cooling, the catalyst was filtered off. The filtrate was concentrated by evaporation, and the residue was recrystallized from ethanol.
Yield: 0.16 gm (72% of theory),
M.p.: 226°–228° C.

| Calc.: | C | 75.99 | H | 6.83 | N | 6.33 |
|---|---|---|---|---|---|---|

-continued

| Found: | 75.81 | 6.73 | 6.10 |

By use of procedures analogous to that of Example 65, the following compounds were prepared:

(a)
4-{N-[2-Methyl-piperidino)-α-phenyl-benzyl]-aminocarbonylmethyl}-benzoic acid Prepared from 4-{N-[5-chloro-2-(2-methyl-piperidino)-α-phenyl-benzyl]-aminocarbonylmethyl}-benzoic acid.
Yield: 68% of theory,
M.p.: 246°–248° C.

| Calc.: | C | 75.99 | H | 6.83 | N | 6.33 |
| Found: | | 75.57 | | 7.10 | | 6.44 |

(b) 4-{N-[2-(3-Methyl-piperidino)-α-phenyl-benzyl]-aminocarbonylmethyl}-benzoic acid
Prepared from 4-{N-[5-chloro-2-(3-methyl-piperidino)-α-phenyl-benzyl]-aminocarbonylmethyl}-benzoic acid.
Yield: 43% of theory,
M.p.: 228°–230° C.

| Calc.: | C | 75.99 | H | 6.83 | N | 6.33 |
| Found: | | 75.91 | | 6.82 | | 6.33 |

Example 66

Ethyl 4-{N-[α-(4-methyl-phenyl)-2-piperidino-benzyl]-aminocarbonylmethyl}-benzoate A solution of 2.78 gm (10 m mol) of freshly prepared (4-methyl-phenyl)-(2-piperidinophenyl)-ketimine in 50 ml of methylene chloride was mixed with 1.5 ml (11 m mol) of triethylamine, and then a solution of 2.5 gm (11 m mol) of 4-ethoxycarbonyl-phenylacetic acid chloride in 20 ml of methylene chloride was added dropwise thereto, while the mixture was cooled with ice. After one hour at ambient temperature, the mixture was poured onto ice-water and extracted with methylene chloride. The extracts were dried and concentrated by evaporation, and the evaporation residue was purified by column chromatography on silica gel [eluant: toluene/ethyl acetate (10:1)]. The crude acylimine was dissolved in dimethylformamide, and, after addition of 0.5 gm of palladium (10% on charcoal), it was hydrogenated at ambient temperature under a hydrogen pressure of 5 bar. After the calculated quantity of hydrogen was taken up, the catalyst was removed by filtering, the filtrate was concentrated by evaporation, and the residue was recrystallized from a small amount of alcohol.
Yield: 2.8 gm (60% of theory),
M.p.: 175°–177° C.

| Calc.: | C | 76.57 | H | 7.28 | N | 5.95 |
| Found: | | 76.41 | | 7.19 | | 5.76 |

Example 67

4-{N-[α-(4-Methyl-phenyl)-2-piperidino-benzyl]-aminocarbonylmethyl}-benzonitrile Prepared from α-(4-methyl-phenyl)-2-piperidino-benzylamine and 4-cyano-phenylacetic acid analogously to Example 55.
Yield: 64% of theory,
M.p.: 144°–146° C.

| Calc.: | C | 79.40 | H | 6.90 | N | 9.92 |
| Found: | | 79.10 | | 6.90 | | 9.78 |

By use of a procedure analogous to that of Example 67, the following compound was prepared:
4-[N-(α-Phenyl-2-piperidino-benzyl)-aminocarbonylmethyl]-benzonitrile
Yield: 53% of theory,
M.p.: 178°–181° C.

| Calc.: | C | 79.18 | H | 6.65 | N | 10.26 |
| Found: | | 78.84 | | 6.55 | | 10.24 |

Example 68

Ethyl 4-{N-[α-(4-methyl-phenyl)-2-piperidino-benzyl)-aminocarbonylmethyl}-benzoate An amount of 4.2 gm (10 m mol) of 4-{N-[α-(4-methyl-phenyl)-2-piperidino-benzyl]-aminocarbonylmethyl}-benzonitrile was refluxed for 24 hours with 50 ml of ethanolic hydrochloric acid. The mixture was then concentrated by evaporation, and the evaporation residue was mixed with aqueous sodium bicarbonate solution and extracted with chloroform. The chloroform extract was concentrated by evaporation, and the residue was triturated with ethanol and subjected to suction filtration.
Yield: 2.9 gm (61.6% of theory),
M.p.: 177°–179° C.

| Calc.: | C | 76.57 | H | 7.28 | N | 5.95 |
| Found: | | 76.41 | | 7.35 | | 5.76 |

By use of a procedure analogous to that of Example 68, the following compound was prepared:

Ethyl 4-[N-(5-methyl-α-phenyl-2-piperidino-benzyl)aminocarbonylmethyl]-benzoate Yield: 57% of theory,
M.p.: 170°–173° C.

| Calc.: | C | 76.57 | H | 7.28 | N | 5.95 |
| Found: | | 76.41 | | 7.19 | | 5.65 |

Example 69

Ethyl 4-{N-[5-chloro-α-(2-chloro-phenyl)-2-piperidino-benzyl]-aminocarbonylmethyl}-benzoate Ten millimoles of ethyl 4-{N-[α-(2-chloro-phenyl)-5-nitro-2-piperidino-benzyl]-aminocarbonylmethyl}-benzoate were dissolved in 50 ml of dimethylformamide and, after addition of 1 gm of Raney nickel, hydrogenated at 60° C. under a hydrogen pressure of 6 bar. Then, the catalyst was filtered off, the filtrate was concentrated by evaporation, and the residue, consisting of ethyl 4-{N-[5-amino-α-(2-chloro-phenyl)-2-piperidino-benzyl]-aminocarbonylmethyl}-benzoate, was dissolved in 100 ml of concentrated hydrochloric acid. While the mixture was cooled with ice, a solution of 1.0 gm (14 m mol) of sodium nitrite in 10 ml of water was added dropwise thereto, and the resulting mixture was stirred for one hour at 0° to 5° C. The reaction mixture was then added dropwise to a solution of 3 gm of copper-(I) chloride in 25 ml of concentrated hydrochloric acid. After stirring for one hour, the mixture was made alkaline with sodium hydroxide solution and extracted with chloroform. The concentrated chloroform extracts were purified by column chromatography on silica gel by use of toluene/ethyl acetate (5:1) as eluant.

Yield: 1.5 gm (28.6% of theory),
M.p.: 213°–215° C.

| Calc.: | C | 66.28 | H | 5.75 | N | 5.33 | Cl | 13.49 |
|---|---|---|---|---|---|---|---|---|
| Found: | | 66.40 | | 5.91 | | 5.41 | | 13.40 |

By use of a procedure analogous to that of Example 69, the following compound was prepared:
Ethyl 4-{N-[5-chloro-2-(3,5-cis-dimethyl-piperidino)-α-phenyl-benzyl)-aminocarbonylmethyl}-benzoate
Yield: 28% of theory,
M.p.: 188°–191° C.

| Calc.: | C | 71.72 | H | 6.80 | N | 5.40 | Cl | 6.83 |
|---|---|---|---|---|---|---|---|---|
| Found: | | 71.95 | | 6.85 | | 5.35 | | 6.77 |

Example 70

3-{4-[N-(α-(4-Methyl-phenyl)-2-piperidino-benzyl)-aminocarbonylmethyl]-phenyl}-propionic acid An amount of 0.91 gm (2 m mol) of 4-[N-(α-(4-methyl-phenyl)-2-piperidino-benzyl)-aminocarbonylmethyl]-cinnamic acid was dissolved in 50 ml of methanol, and, after the addition of 0.5 gm of palladium (10% on charcoal), the mixture was catalytically hydrogenated at ambient temperature under a hydrogen pressure of 3 bar. After the hydrogen uptake ended, the catalyst was filtered off and recrystallized from a small amount of acetonitrile.

Yield: 0.68 gm (74% of theory),
M.p.: 146°–148° C.

| Calc.: | C | 76.57 | H | 7.28 | N | 5.95 |
|---|---|---|---|---|---|---|
| Found: | | 76.41 | | 7.19 | | 5.61 |

By use of a procedure analogous to that of Example 70, the following compound was prepared:
3-{4-[N-(α-Phenyl-2-piperidino-benzyl)-aminocarbonylmethyl]-phenyl}-propionic acid
Yield: 65% of theory,
M.p.: 97°–99° C.

| Calc.: | C | 76.30 | H | 7.06 | N | 6.13 |
|---|---|---|---|---|---|---|
| Found: | | 76.35 | | 6.95 | | 5.91 |

Example 71

Sodium salt of 4-[N-(α-(4-methyl-phenyl)-2-piperidino-benzyl)-aminocarbonylmethyl]-benzoic acid Four hundred forty-two milligrams (1 m mol) of 4-[N-(α-(4-methyl-phenyl)-2-piperidino-benzyl)-aminocarbonylmethyl]-benzoic acid were dissolved in 25 ml of ethanol and mixed with 1 ml of 1N sodium hydroxide solution. The mixture was then concentrated by evaporation in vacuo, 20 ml of acetone were added, and the precipitate obtained was subjected to suction filtration and washed with ethyl acetate.

Yield: 410 mg (85% of theory),
M.p.: 295°–300° C.

| Calc.: | C | 72.40 | H | 6.29 | N | 6.03 |
|---|---|---|---|---|---|---|
| Found: | | 72.15 | | 6.46 | | 5.93 |

By use of procedures analogous to that of Example 71, the following compounds were prepared:
(a) Ethanolamine salt of 4-[N-(α-(4-methyl-phenyl)-2-piperidino-benzyl)-aminocarbonylmethyl]-benzoic acid
Yield: 75% of theory,
M.p.: 188°–191° C.

| Calc.: | C | 71.55 | H | 7.41 | N | 8.34 |
|---|---|---|---|---|---|---|
| Found: | | 71.16 | | 7.48 | | 8.52 |

(b) Diethanolamine salt of 4-[N-(α-(4-methyl-phenyl)-2-piperidino-benzyl)-aminocarbonylmethyl]-benzoic acid
Yield: 81% of theory,
M.p.: 178°–180° C.

| Calc.: | C | 70.70 | H | 6.86 | N | 7.73 |
|---|---|---|---|---|---|---|
| Found: | | 70.25 | | 6.75 | | 7.58 |

(c) Triethanolamine salt of 4-[N-(α-(4-methyl-phenyl)-2-piperidino-benzyl)-aminocarbonylmethyl]-benzoic acid
Yield: 76% of theory,
M.p.: 160°–165° C.

| Calc.: | C | 69.01 | H | 7.67 | N | 7.10 |
|---|---|---|---|---|---|---|
| Found: | | 68.91 | | 7.64 | | 7.45 |

(d) Ethylenediamine salt of 4-[N-(α-(4-methyl-phenyl)-2-piperidino-benzyl)-aminocarbonylmethyl]benzoic acid
Yield: 65% of theory,
M.p.: 160°–163° C.

| Calc.: | C | 71.69 | H | 7.62 | N | 11.15 |
|---|---|---|---|---|---|---|
| Found: | | 72.04 | | 7.80 | | 10.96 |

Example 72

Ethyl 4-[N-(5-methoxy-α-phenyl-2-piperidino-benzyl)-aminocarbonyl-methyl]-benzoate

Four hundred seventy-two milligrams (1 m mol) of ethyl 4-[N-(5-hydroxy-α-phenyl-2-piperidino-benzyl)-aminocarbonylmethyl]-benzoate were dissolved in 25 ml of absolute dimethylformamide. After addition of 50 g of 50% sodium hydride, the mixture was stirred for 30 minutes. Then, 0.5 gm of methyl iodide were added dropwise, and the resulting mixture was stirred overnight. To work the mixture up, it was poured onto ice-water and extracted with methylene chloride. The concentrated extracts were purified by column chromatography on silica gel by use of toluene/ethyl acetate (4:1) as eluant.

Yield: 260 mg (53% of theory),
M.p.: 123°–125° C.

| | | | | | | | |
|---|---|---|---|---|---|---|---|
| Calc.: | C | 74.05 | H | 7.04 | N | 5.76 |
| Found: | | 73.86 | | 6.95 | | 5.61 |

Example 73

Ethyl 4-[(2-methoxy-1-(2-piperidino-phenyl)-ethyl]-aminocarbonylmethyl]-benzoate

Quantities of 0.49 gm (2.34 m mol) of 4-ethoxycarbonylphenylacetic acid, 0.73 gm (2.78 m mol) of triphenylphosphine, 0.50 ml (3.66 m mol) of triethylamine, and 0.23 ml (2.34 m mol) of carbon tetrachloride were added successively to a solution of 0.55 gm (2.34 m mol) of 2-methoxy-1-(2-piperidino-phenyl)-ethylamine in 5 ml of acetonitrile, and the resulting mixture was stirred for 20 hours at ambient temperature. It was then concentrated by evaporation in vacuo and distributed between ethyl acetate and water. The organic extract was dried, filtered, and evaporated in vacuo. The evaporation residue was purified by column chromatography on silica gel (toluene/acetone (10:2)].

Yield: 0.45 gm (45% of theory),
M.p.: 122°–123° C.

| | | | | | | |
|---|---|---|---|---|---|---|
| Calc.: | C | 70.73 | H | 7.60 | N | 6.60 |
| Found: | | 71.04 | | 7.48 | | 6.39 |

By use of the procedures analogous to that of Example 73, the following compounds were prepared:

(a) Ethyl 4-[(1-(3-chloro-2-piperidino-phenyl)-1-butyl)-aminocarbonylmethyl]-benzoate
Yield: 55% of theory,
M.p.: 141°–143° C.

| | | | | | | | | |
|---|---|---|---|---|---|---|---|---|
| Calc.: | C | 68.33 | H | 7.28 | Cl | 7.76 | N | 6.13 |
| Found: | | 68.30 | | 7.16 | | 8.03 | | 6.20 |

(b) Ethyl 4-[(1-(6-chloro-2-piperidino-phenyl)-1-butyl)-aminocarbonylmethyl]-benzoate
Yield: 73.9% of theory,
M.p.: 79°–82° C.

| | | | | | | | | |
|---|---|---|---|---|---|---|---|---|
| Calc.: | C | 68.33 | H | 7.28 | Cl | 7.76 | N | 6.13 |
| Found: | | 68.45 | | 7.24 | | 7.80 | | 6.09 |

(c) Ethyl 4-[(1-(4-bromo-2-piperidino-phenyl)-1-butyl)-aminocarbonylmethyl]-benzoate
Yield: 62.1% of theory,
M.p.: 116°–118° C.

| | | | | | | | | |
|---|---|---|---|---|---|---|---|---|
| Calc.: | C | 62.27 | H | 6.63 | Br | 15.93 | N | 5.58 |
| Found: | | 62.53 | | 6.48 | | 15.98 | | 5.66 |

(d) Ethyl 4-[(1-(4-nitro-2-piperidino-phenyl)-1-butyl)-aminocarbonylmethyl]-benzoate
Yield: 74.6% of theory,
M.p.: 127°–130° C.

| | | | | | | |
|---|---|---|---|---|---|---|
| Calc.: | C | 66.79 | H | 7.11 | N | 8.99 |
| Found: | | 66.88 | | 7.08 | | 9.15 |

(e) Ethyl 4-[(1-(3-methyl-2-piperidino-phenyl)-1-butyl)-aminocarbonylmethyl]-benzoate
Yield: 68% of theory,
M.p.: 145°–147° C.

| | | | | | | |
|---|---|---|---|---|---|---|
| Calc.: | C | 74.28 | H | 8.31 | N | 6.42 |
| Found: | | 74.40 | | 8.30 | | 6.41 |

(f) Ethyl 4-[(1-(4-methyl-2-piperidino-phenyl)-1-butyl)-aminocarbonylmethyl]-benzoate
Yield: 54.7% of theory,
M.p.: 113°–114° C.

| | | | | | | |
|---|---|---|---|---|---|---|
| Calc.: | C | 74.28 | H | 8.31 | N | 6.42 |
| Found: | | 74.23 | | 8.30 | | 6.55 |

(g) Ethyl 4-[(1-(5-methyl-2-piperidino-phenyl)-1-butyl)-aminocarbonylmethyl]-benzoate
Yield: 67.9% of theory,
M.p.: 149°–150° C.

| | | | | | | |
|---|---|---|---|---|---|---|
| Calc.: | C | 74.28 | H | 8.31 | N | 6.42 |
| Found: | | 74.38 | | 8.21 | | 6.49 |

(h) Ethyl 4-[(1-(6-methyl-2-piperidino-phenyl)-1-butyl)-aminocarbonylmethyl]-benzoate
Yield: 47% of theory,
M.p.: 92°–93° C.

| | | | | | | |
|---|---|---|---|---|---|---|
| Calc.: | C | 74.28 | H | 8.31 | N | 6.42 |
| Found: | | 74.50 | | 8.46 | | 6.48 |

(i) Ethyl 4-[(1-(2-pyrrolidino-phenyl)-1-butyl)-aminocarbonylmethyl]-benzoate
Yield: 57.3% of theory,
M.p.: 122°–125° C.

| | | | | | | |
|---|---|---|---|---|---|---|
| Calc.: | C | 73.50 | H | 7.90 | N | 6.86 |
| Found: | | 73.63 | | 8.07 | | 7.01 |

(k) Ethyl 4-[(1-(2-piperidino-phenyl)-1-butyl)-aminocarbonylmethyl]-benzoate

Yield: 71.5% of theory,
M.p.: 127°–128° C.

| Calc.: | C | 73.90 | H | 8.11 | N | 6.63 |
|---|---|---|---|---|---|---|
| Found: | | 73.90 | | 8.06 | | 6.72 |

(l) Ethyl 4-[(1-(2-(4-methyl-piperidino)-phenyl)-1-butyl)-aminocarbonylmethyl]-benzoate
Yield: 51.1% of theory,
M.p.: 153°–155° C.

| Calc.: | C | 74.28 | H | 8.31 | N | 6.42 |
|---|---|---|---|---|---|---|
| Found: | | 74.55 | | 8.33 | | 6.45 |

(m) Ethyl 4-[(1-(2-hexahydroazepino-phenyl)-1-butyl)-aminocarbonylmethyl]-benzoate
Yield: 42.7% of theory,
M.p.: 145°–147° C.

| Calc.: | C | 74.28 | H | 8.31 | N | 6.42 |
|---|---|---|---|---|---|---|
| Found: | | 73.98 | | 8.26 | | 6.58 |

(n) Ethyl 4-[(1-(5-fluoro-2-piperidino-phenyl)-1-butyl)-aminocarbonylmethyl]-benzoate
Yield: 55% of theory,
M.p.: 128°–130° C.

| Calc.: | C | 70.88 | H | 7.55 | N | 6.36 |
|---|---|---|---|---|---|---|
| Found: | | 71.14 | | 7.57 | | 6.49 |

(o) Methyl 4-[(1-(2-piperidino-phenyl)-1-butyl)-aminocarbonylmethyl]-benzoate
Yield: 63.2% of theory,
M.p.: 147°–148° C.

| Calc.: | C | 73.50 | H | 7.90 | N | 6.86 |
|---|---|---|---|---|---|---|
| Found: | | 73.66 | | 7.88 | | 6.80 |

(p) n-Butyl 4-[(1-(2-piperidino-phenyl)-1-butyl)-aminocarbonylmethyl]-benzoate
Yield: 50.9% of theory,
M.p.: 117°–119° C. (ether)

| Calc.: | C | 74.63 | H | 8.50 | N | 6.22 |
|---|---|---|---|---|---|---|
| Found: | | 74.49 | | 8.46 | | 6.14 |

(q) Ethyl 3-chloro-4-[(1-(2-piperidino-phenyl)-1-butyl)-aminocarbonylmethyl]-benzoate
Yield: 14.9% of theory,
M.p.: <20° C.

| Calc.: | m/e = 456/458 (1 chloro) |
|---|---|
| Found: | m/e = 456/458 (1 chloro) |

(r) Ethyl 4-[(1-(2-piperidino-phenyl)-4-penten-1-yl)-aminocarbonylmethyl]-benzoate
Yield: 18.9% of theory,
M.p.: 103°–105° C.

| Calc.: | C | 74.62 | H | 7.89 | N | 6.45 |
|---|---|---|---|---|---|---|
| Found: | | 75.01 | | 8.10 | | 6.26 |

(s) Ethyl 4-[(1-(3-chloro-2-piperidino-phenyl)-1-ethyl)-aminocarbonylmethyl]-benzoate
Yield: 58.0% of theory,
M.p.: 166°–168° C.

| Calc.: | C | 67.20 | H | 6.81 | Cl | 8.27 | N | 6.53 |
|---|---|---|---|---|---|---|---|---|
| Found: | | 67.17 | | 6.85 | | 8.17 | | 6.45 |

Example 74

Ethyl 4-[(1-(5-nitro-2-piperidino-phenyl)-1-butyl)-aminocarbonylmethyl]-benzoate A solution of 14.6 gm (64.6 m mol) of 4-ethoxy-carbonylphenylacetic acid chloride in 20 ml of methylene chloride was added dropwise to a stirred solution of 15.1 gm (54.4 m mol) of 1-(5-nitro-2-piperidino-phenyl)-1-butylamine and 8.46 ml (61.4 m mol) of triethylamine in 55 ml of dry methylene chloride within 30 minutes in such a way that the temperature did not exceed 30° C. The mixture was stirred for a further two hours at ambient temperature, 300 ml of methylene chloride were added, and the resulting mixture was extracted twice, each time with 50 ml of water. The organic phase was dried over sodium sulfate, filtered, and concentrated by evaporation in vacuo. The reddish-brown oily evaporation residue was purified by column chromatography on silica gel [toluene/acetone (10:1)].
Yield: 17.7 gm (69.7% of theory),
M.p.: 135°–137° C. (ether)

| Calc.: | C | 66.79 | H | 7.11 | N | 8.99 |
|---|---|---|---|---|---|---|
| Found: | | 66.73 | | 6.99 | | 9.09 |

By use of procedures analogous to that of Example 74, the following compounds were prepared:
(a) Ethyl 4-[(1-(2-piperidino-phenyl)-1-butyl)-aminocarbonylmethyl]-benzoate
Yield: 80.2% of theory,
M.p.: 127°–129° C.

| Calc.: | C | 73.90 | H | 8.11 | N | 6.63 |
|---|---|---|---|---|---|---|
| Found: | | 73.98 | | 8.26 | | 6.89 |

(b) Ethyl 4-[(1-(4-hydroxy-2-piperidino-phenyl)-1-butyl)-aminocarbonylmethyl]-benzoate
Yield: 13.5% of theory,
M.p.: 178°–180° C.

| Calc.: | C | 71.21 | H | 7.81 | N | 6.39 |
|---|---|---|---|---|---|---|
| Found: | | 71.27 | | 7.82 | | 6.40 |

(c) Ethyl 4-[(1-(5-hydroxy-2-piperidino-phenyl)-1-butyl)-aminocarbonylmethyl]-benzoate
Yield: 37.4% of theory,
M.p.: 188°–190° C.

| Calc.: | C | 71.21 | H | 7.81 | N | 6.39 |
|---|---|---|---|---|---|---|

| Found: | 71.34 | 7.89 | 6.38 |
|---|---|---|---|

Example 75

4-[(1-(2-piperidino-phenyl)-1-butyl)-aminocarbonylmethyl]-phenylacetic acid

Three grams (15.45 m mol) of p-phenylene-diacetic acid and 10 ml of thionyl chloride were refluxed for 90 minutes and then concentrated by evaporation in vacuo. The crude diacid chloride was dissolved in 100 ml of methylene chloride. Then, a solution of 3.6 gm (15.45 m mol) of 1-(2-piperidino-phenyl)-1-butylamine was slowly added dropwise to this solution, under stirring, at an internal temperature of 10° to 15° C. After two hours at ambient temperature, the mixture was concentrated by evaporation in vacuo, and the evaporation residue was distributed between 100 ml of ice-cold 5% sodium hydroxide solution and ethyl acetate. It was filtered through kieselguhr, and the organic phase was separated off. The alkaline-aqueous phase was adjusted to a pH of 5.5 with semi-concentrated hydrochloric acid and extracted with ethyl acetate. The extract was dried over sodium sulfate and filtered, and the filtrate was concentrated by evaporation in vacuo. The evaporation residue was purified by column chromatography on silica gel [chloroform/methanol (20:1)].

Yield: 0.10 gm (1.6% of theory),
M.p.: 136°–140° C. (acetonitrile/ether)

| Calc.: | C | 73.50 | H | 7.90 | N | 6.86 |
|---|---|---|---|---|---|---|
| Found: |  | 73.17 |  | 8.10 |  | 6.85 |

Example 76

Ethyl 4-[(2-methyl-1-(2-piperidino-phenyl)-1-propen-1-yl)-aminocarbonylmethyl]-benzoate

Amounts of 5.58 gm (26.8 m mol) of 4-ethoxycarbonylphenylacetic acid, 8.43 gm (32.2 m mol) of triphenylphosphine, 11.2 ml (80.4 m mol) of triethylamine, and 2.6 ml (0.0268 mol) of carbon tetrachloride were added successively to a solution of 6.17 gm (26.8 m mol) of freshly prepared isopropyl-(2-piperidino-phenyl)-ketimine in 62 ml of acetonitrile, and the resulting mixture was stirred for 20 hours at an ambient temperature. The mixture was then concentrated by evaporation in vacuo. The evaporation residue was purified by column chromatography on silica gel [toluene/ethyl acetate (5:1)].

Yield: 3.0 gm (26.6% of theory),
M.p.: 82°–84° C. (ether)

| Calc.: | C | 74.26 | H | 7.67 | N | 6.66 |
|---|---|---|---|---|---|---|
| Found: |  | 74.20 |  | 7.49 |  | 6.56 |

By use of procedures analogous to that of Example 76, the following compounds were prepared:

(a) Ethyl 4-[(1-(2-piperidino-phenyl)-1-penten-1-yl)-aminocarbonylmethyl]-benzoate
Yield: 16% of theory,
M.p.: 94°–97° C. (ethanol)

| Calc.: | C | 74.62 | H | 7.89 | N | 6.45 |
|---|---|---|---|---|---|---|
| Found: |  | 74.75 |  | 7.71 |  | 6.24 |

(b) Ethyl 4-[(1-(2-piperidino-phenyl)-1-hexen-1-yl)-aminocarbonylmethyl]-benzoate
Yield: 27.4% of theory,
M.p.: 83°–85° C. (ethanol)

| Calc.: | C | 74.97 | H | 8.09 | N | 6.24 |
|---|---|---|---|---|---|---|
| Found: |  | 75.42 |  | 7.95 |  | 6.00 |

(c) Ethyl 4-[(1-(2-piperidino-phenyl)-1-buten-1-yl)-aminocarbonylmethyl]-benzoate
Yield (more lipophilic isomer; probably E form): 4.1% of theory,
M.p.: <20° C.

| Calc.: | m/e = 420 |
|---|---|
| Found: | m/e = 420 |

Yield (less lipophilic isomer; probably Z form): 51.9% of theory,
M.p.: 115°–117° C. (ethanol)

| Calc.: | C | 74.26 | H | 7.67 | N | 6.66 |
|---|---|---|---|---|---|---|
| Found: |  | 73.85 |  | 7.59 |  | 6.44 |

(d) Ethyl 4-[(2-phenyl-1-(2-piperidino-phenyl)-ethen-1-yl)-aminocarbonylmethyl]-benzoate
Yield (more lipophilic isomer; probably E form): 4% of theory,
M.p.: 75°–77° C. (ether/petroleum ether)

| Calc.: | C | 76.90 | H | 6.88 | N | 5.98 |
|---|---|---|---|---|---|---|
| Found: |  | 77.31 |  | 7.20 |  | 5.93 |

Yield (less lipophilic isomer; probably Z form): 42.7% of theory,
M.p.: 157°–160° C. (ethanol)

| Calc.: | C | 76.90 | H | 6.88 | N | 5.98 |
|---|---|---|---|---|---|---|
| Found: |  | 77.19 |  | 6.95 |  | 6.02 |

(e) Ethyl 4-[(3-phenyl-1-(2-piperidino-phenyl)-1-propen-1-yl)-aminocarbonylmethyl]-benzoate
Yield: 62.6% of theory,
M.p.: <20° C.

| Calc.: | m/e = 482 |
|---|---|
| Found: | m/e = 482 |

(f) Ethyl 4-[(1-(2-(3,3-dimethyl-piperidino)-phenyl)-1-buten-1-yl)-aminocarbonylmethyl]-benzoate
Yiled: 33% of theory,
M.p.: 113°–116° C. (ethanol)

| Calc.: | C | 74.97 | H | 8.09 | N | 6.24 |
|---|---|---|---|---|---|---|
| Found: |  | 75.37 |  | 7.93 |  | 6.03 |

(g) Ethyl 4-[(1-(6-methyl-2-piperidino-phenyl)-1-buten-1-yl)-aminocarbonylmethyl]-benzoate
Yield: 60.4% of theory (probably Z form)
M.p.: 95°–96° C.

| Calc.: | C | 74.62 | H | 7.89 | N | 6.45 | m/e = 434 |
|---|---|---|---|---|---|---|---|
| Found: | | 74.44 | | 8.00 | | 6.59 | m/e = 434 |

Example 77

Ethyl 4-[(1-(2-piperidino-phenyl)-1-buten-1-yl)-aminocarbonylmethyl]-benzoate

A stirred solution of 19.0 gm (82.46 m mol) of freshly prepared (2-piperidino-phenyl)-propyl-ketimine and 11.5 ml of (82.46 m mol) of triethylamine in 190 ml of anhydrous toluene was heated to an internal temperature of 85° C., a solution of 18.7 gm (82.46 m mol) of 4-ethoxycarbonyl-phenylacetic acid chloride in 95 ml of anhydrous toluene was added dropwise thereto over a period of 10 minutes, and the resulting mixture was stirred for 30 minutes at an internal temperature of 95° C. The mixture was then cooled to 20° C. and extracted twice with water. The organic phase was dried over sodium sulfate, filtered, and concentrated by evaporation in vacuo. The evaporation residue was purified by repeated column chromatography [toluene/acetone (20:1) and (50:1)].

Yield (more lipophilic isomer; probably E form): 11.2 gm (23.6% of theory),
M.p.: <20° C. (honey-yellow viscous oil)

| Calc.: | C | 74.26 | H | 7.67 | N | 6.66 |
|---|---|---|---|---|---|---|
| Found | | 73.90 | | 7.92 | | 6.91 |

Yield (less lipophilic isomer; probably Z form): 15.9 gm (33.5% of theory),
M.p.: 114°–116° C.

| Calc.: | C | 74.26 | H | 7.67 | N | 6.66 |
|---|---|---|---|---|---|---|
| Found: | | 74.02 | | 7.69 | | 6.85 |

Example 78

Ethyl (E)- and (Z)-4-[(1-(2-piperidino-phenyl)-1-buten-1-yl)-aminocarbonylmethyl]-benzoate One gram of Z ester (see Example 76(c)) was heated for 30 minutes in a pre-heated oil bath at 230° C. After cooling, the product obtained was purified by column chromatography on silica gel [toluene/acetone (20:1)].
Yield (E ester): 0.365 gm (36.5% of theory),
M.p.: <20° C.
Yield (Z ester): 0.380 gm (38.0% of theory),
M.p.: 115°–117° C.
If the (E)-ester is heated for three and one-half hours with catalytic quantities of iodine in benzene, a 1:1 mixture of (E) and (Z) esters is obtained, according to thin layer chromatography [toluene/acetone (10:1)].
By use of a procedure analogous to that of Example 78, the following mixture was prepared:
Ethyl (E)- and (Z)-4-[(1-(6-methyl-2-piperidino-phenyl)-1-buten-1-yl)-aminocarbonylmethyl]-benzoate
According to thin layer chromatography, a 1:1 mixture of (E) and (Z) esters is obtained from the (Z) ester (see Example 76(g)).

| Upper spot (E): | Calc.: | m/e = 434 |
|---|---|---|
| | Found: | m/e = 434 |
| Lower spot (Z): | Calc.: | m/e = 434 |
| | Found: | m/e = 434 |

Example 79

Ethyl 4-[(1-(2-piperidino-phenyl)-1-butyl)-aminocarbonylmethyl]-benzoate

A quantity of 2.9 gm (6.90 m mol) of ethyl 4-[(1-(2-piperidino-phenyl)-1-buten-1-yl)-aminocarbonylmethyl]-benzoate in 100 ml of ethanol was hydrogenated on 0.77 gm of 10% palladium/charcoal at 50° C. under a hydrogen pressure of 1 bar. After two hours, the catalyst was filtered off over kieselguhr, and the filtrate was concentrated by evaporation in vacuo. The evaporation residue was crystallized from ethanol.
Yield: 1.5 gm (51.5% of theory),
M.p.: 126°–128° C.

| Calc.: | C | 73.90 | H | 8.11 | N | 6.63 |
|---|---|---|---|---|---|---|
| Found: | | 73.97 | | 8.22 | | 6.57 |

By use of procedures analogous to that of Example 79, the following compounds were prepared:

(a) Ethyl 4-[(1-(2-piperidino-phenyl)-1-pentyl)-aminocarbonylmethyl]-benzoate
Yield: 45% of theory,
M.p.: 117°–120° C. (ether)

| Calc.: | C | 74.28 | H | 8.31 | N | 6.42 |
|---|---|---|---|---|---|---|
| Found: | | 74.60 | | 8.13 | | 6.27 |

(b) Ethyl 4-[(1-(2-piperidino-phenyl)-1-hexyl)-aminocarbonylmethyl]-benzoate
Yield: 50% of theory,
M.p.: 108°–110° C. (ether)

| Calc.: | C | 74.63 | H | 8.50 | N | 6.22 |
|---|---|---|---|---|---|---|
| Found: | | 74.85 | | 8.33 | | 6.01 |

(c) Ethyl 4-[(2-phenyl-1-(2-piperidino-phenyl)-1-ethyl)-aminocarbonylmethyl]-benzoate
Yield: 87.6% of theory,
M.p.: 161°–162° C. (ethanol)

| Calc. | C | 76.57 | H | 7.28 | N | 5.95 |
|---|---|---|---|---|---|---|
| Found: | | 76.71 | | 7.19 | | 5.99 |

(d) Ethyl 4-[(3-phenyl-1-(2-piperidino-phenyl)-1-propyl)-aminocarbonylmethyl]-benzoate
Yield: 57.6% of theory,
M.p.: 118°–119° C. (ethanol)

| Calc.: | C | 76.83 | H | 7.49 | N | 5.78 |
|---|---|---|---|---|---|---|
| Found: | | 76.70 | | 7.49 | | 5.90 |

(e) Ethyl 4-[(1-(2-(3,3-dimethyl-piperidino)-phenyl-1-butyl)-aminocarbonylmethyl]-benzoate
Yield: 36.5% of theory,
M.p.: 140°-141° C. (ethanol)

| Calc.: | C | 74.63 | H | 8.50 | N | 6.22 |
|---|---|---|---|---|---|---|
| Found: | | 74.30 | | 8.23 | | 6.12 |

Example 80
4-[(1-(2-Piperidino-phenyl)-1-butyl)-aminocarbonylmethyl]-benzoic acid A mixture of 1.2 gm (2.84 m mol) of ethyl 4-[(1-(2-piperidino-phenyl)-1-butyl)-aminocarbonylmethyl]-benzoate and 4.26 ml of 1N sodium hydroxide solution in 12 ml of ethanol was stirred for one hour at 60° C. and neutralized with 4.26 ml of 1N hydrochloric acid, and the ethanol was evaporated off in vacuo. The residue was distributed between ethyl acetate and water, and the organic extract was dried, filtered, and concentrated by evaporation in vacuo. The evaporation residue was crystallized from ethanol.
Yield: 0.50 gm (44.6% of theory),
M.p.: 213°-215° C.

| Calc.: | C | 73.07 | H | 7.66 | N | 7.10 |
|---|---|---|---|---|---|---|
| Found: | | 73.18 | | 7.51 | | 7.10 |

By use of procedures analogous to that of Example 80, the following compounds were prepared:

(a)  4-[(1-(2-Piperidino-phenyl)-1-pentyl)-aminocarbonylmethyl]-benzoic acid
Yield: 70.2% of theory,
M.p.: 213°-215° C. (acetone)

| Calc.: | C | 73.50 | H | 7.90 | N | 6.86 |
|---|---|---|---|---|---|---|
| Found: | | 73.71 | | 7.70 | | 6.90 |

(b)  4-[(1-(2-Piperidino-phenyl)-1-hexyl)-aminocarbonylmethyl]-benzoic acid
Yield: 72.6% of theory,
M.p.: 197°-200° C. (acetone)

| Calc.: | C | 73.90 | H | 8.11 | N | 6.63 |
|---|---|---|---|---|---|---|
| Found: | | 73.83 | | 7.93 | | 6.77 |

(c)  4-[(2-Phenyl-1-(2-piperidino-phenyl)-1-ethyl)-aminocarbonylmethyl]-benzoic acid
Yield: 68.7% of theory,
M.p.: 214°-215° C. (acetone)

| Calc.: | C | 75.99 | H | 6.83 | N | 6.33 |
|---|---|---|---|---|---|---|
| Found: | | 75.70 | | 6.60 | | 6.32 |

(d)  4-[(3-Phenyl-1-(2-piperidino-phenyl)-1-propyl)-aminocarbonylmethyl]-benzoic acid
Yield: 67.7% of theory,
M.p.: 167°-170° C. (ethyl acetate)

| Calc.: | C | 76.29 | H | 7.06 | N | 6.14 |
|---|---|---|---|---|---|---|
| Found: | | 76.56 | | 7.06 | | 6.23 |

(e)  4-[2-Methoxy-1-(2-piperidino-phenyl)-1-ethyl)-aminocarbonylmethyl]-benzoic acid
Yield: 60.8% of theory,
M.p.: 196°-198° C. (ether)

| Calc.: | C | 69.68 | H | 7.12 | N | 7.07 |
|---|---|---|---|---|---|---|
| Found: | | 69.72 | | 6.52 | | 6.71 |

(f) 4-[(1-(2-Piperidino-phenyl)-4-penten-1-yl)-aminocarbonylmethyl]-benzoic acid × 0.67 H$_2$O
Yield: 30.7% of theory,
M.p.: 193°-197° C. (ether/petroleum ether)

| Calc.: | C | 71.74 | H | 7.38 | N | 6.69 |
|---|---|---|---|---|---|---|
| Found: | | 71.63 | | 7.21 | | 6.34 |

(g) 4-[(1-(2-(3,3-Dimethyl-piperidino)-phenyl)-1-butyl)-aminocarbonylmethyl]-benzoic acid
Yield: 48.2% of theory,
M.p.: 168°-170° C. (petroleum ether)

| Calc.: | C | 73.91 | H | 8.11 | N | 6.63 |
|---|---|---|---|---|---|---|
| Found: | | 73.51 | | 7.89 | | 6.32 |

(h)  4-[(1-(3-Methyl-2-piperidino-phenyl)-1-butyl)-aminocarbonylmethyl]-benzoic acid
Yield: 53% of theory,
M.p.: 179°-182° C.

| Calc.: | C | 73.50 | H | 7.90 | N | 6.86 |
|---|---|---|---|---|---|---|
| Found: | | 73.50 | | 7.82 | | 7.01 |

(i)  4-[(1-(4-Methyl-2-piperidino-phenyl)-1-butyl)-aminocarbonylmethyl]-benzoic acid
Yield: 85.6% of theory,
M.p.: 170°-172° C.

| Calc.: | C | 73.50 | H | 7.90 | N | 6.86 |
|---|---|---|---|---|---|---|
| Found: | | 73.25 | | 7.64 | | 6.89 |

(k)  4-[(1-(5-Methyl-2-piperidino-phenyl)-1-butyl)-aminocarbonylmethyl]-benzoic acid
Yield: 62.1% of theory,
M.p.: 219°-221° C.

| Calc.: | C | 73.50 | H | 7.90 | N | 6.86 |
|---|---|---|---|---|---|---|
| Found: | | 73.20 | | 7.74 | | 6.89 |

(l)  4-[(1-(6-Methyl-2-piperidino-phenyl)-1-butyl)-aminocarbonylmethyl]-benzoic acid × 0.3 H$_2$O
Yield: 89% of theory,
M.p.: 158°-160° C.

| Calc.: | C | 72.53 | H | 7.93 | N | 6.77 |
|---|---|---|---|---|---|---|
| Found: | | 72.40 | | 7.91 | | 6.92 |

(m)  4-[(1-(3-Chloro-2-piperidino-phenyl)-1-butyl)-aminocarbonylmethyl]-benzoic acid
Yield: 70% of theory,
M.p.: 189°-191° C.

(n) 4-[(1-(4-Chloro-2-piperidino-phenyl)-1-butyl)-aminocarbonylmethyl]-benzoic acid
Yield: 57.8% of theory,
M.p.: 188°–189° C.

| Calc.: | C | 67.20 | H | 6.81 | Cl | 8.27 | N | 6.53 |
|---|---|---|---|---|---|---|---|---|
| Found: | | 66.90 | | 7.00 | | 8.22 | | 6.53 |

(o) 4-[(1-(5-Chloro-2-piperidino-phenyl)-1-butyl)-aminocarbonylmethyl]-benzoic acid
Yield: 81.6% of theory,
M.p.: 226°–229° C.

| Calc.: | C | 67.20 | H | 6.81 | Cl | 8.27 | N | 6.53 |
|---|---|---|---|---|---|---|---|---|
| Found: | | 67.17 | | 6.59 | | 8.51 | | 6.60 |

(p) 4-[(1-(6-Chloro-2-piperidino-phenyl)-1-butyl)-aminocarbonylmethyl]-benzoic acid
Yield: 69.4% of theory,
M.p.: 150°–153° C.

| Calc.: | C | 67.20 | H | 6.81 | Cl | 8.27 | N | 6.53 |
|---|---|---|---|---|---|---|---|---|
| Found: | | 67.18 | | 6.91 | | 8.42 | | 6.77 |

(q) 4-[(1-(4-Bromo-2-piperidino-phenyl)-1-butyl)-aminocarbonylmethyl]-benzoic acid
Yield: 84.4% of theory,
M.p.: 198°–201° C.

| Calc.: | C | 60.89 | H | 6.17 | Br | 16.88 | N | 5.92 |
|---|---|---|---|---|---|---|---|---|
| Found: | | 60.88 | | 5.98 | | 17.20 | | 5.98 |

(r) 4-[(1-(5-Bromo-2-piperidino-phenyl)-1-butyl)-aminocarbonylmethyl]-benzoic acid
Yield: 90.7% of theory,
M.p.: 232°–235° C.

| Calc.: | C | 60.89 | H | 6.17 | Br | 16.88 | N | 5.92 |
|---|---|---|---|---|---|---|---|---|
| Found: | | 60.96 | | 6.13 | | 16.85 | | 5.90 |

(s) 4-[(1-(4-Nitro-2-piperidino-phenyl)-1-butyl)-amioncarbonylmethyl]-benzoic acid
Yield: 70.9% of theory,
M.p.: 188°–190° C.

| Calc.: | C | 65.59 | H | 6.65 | N | 9.56 |
|---|---|---|---|---|---|---|
| Found: | | 65.30 | | 6.44 | | 9.53 |

(t) 4-[(1-(5-Nitro-2-piperidino-phenyl)-1-butyl)-aminocarbonylmethyl]-benzoic acid
Yield: 90.7% of theory,
M.p.: 225°–227° C.

| Calc.: | C | 65.59 | H | 6.65 | N | 9.56 |
|---|---|---|---|---|---|---|
| Found: | | 65.80 | | 6.61 | | 9.72 |

(u) 4-[(1-(4-Hydroxy-2-piperidino-phenyl)-1-butyl)-aminocarbonylmethyl]-benzoic acid×0.5 $H_2O$
Yield: 85.7% of theory,
M.p.: softening from 70° C. (foam)

| Calc.: | (× 0.5 $H_2O$) | C | 68.71 | H | 7.45 | N | 6.68 |
|---|---|---|---|---|---|---|---|
| Found: | | | 68.63 | | 7.55 | | 6.26 |

(v) 4-[(1-(5-Hydroxy-2-piperidino-phenyl)-1-butyl)-aminocarbonylmethyl]-benzoic acid
Yield: 89.3% of theory,
M.p.: 186°–190° C.

| Calc.: | C | 70.22 | H | 7.37 | N | 6.82 |
|---|---|---|---|---|---|---|
| Found: | | 70.31 | | 7.58 | | 6.51 |

(w) 4-[(1-(4-Methoxy-2-piperidino-phenyl)-1-butyl)-aminocarbonylmethyl]-benzoic acid
Yield: 78.6% of theory,
M.p.: 185°–187° C.

| Calc.: | C | 70.73 | H | 7.60 | N | 6.60 |
|---|---|---|---|---|---|---|
| Found: | | 70.46 | | 7.77 | | 6.56 |

(x) 4-[(1-(5-Methoxy-2-piperidino-phenyl)-1-butyl)-aminocarbonylmethyl]-benzoic acid
Yield: 75% of theory,
M.p.: 182°–185° C. (decomp.)

| | C | H | N |
|---|---|---|---|
| Calc.: | 70.73 | 7.60 | 6.60 |
| Found: | 70.52 | 7.50 | 6.70 |

(y) 4-[(1-(2-Pyrrolidino-phenyl)-1-butyl)-aminocarbonylmethyl]-benzoic acid
Yield: 64.5% of theory,
M.p.: 200°–203° C.

| | C | H | N |
|---|---|---|---|
| Calc.: | 72.61 | 7.42 | 7.36 |
| Found: | 72.64 | 7.50 | 7.38 |

(z) 4-[(1-(2-(4-Methyl-piperidino)-phenyl)-1-butyl)-aminocarbonylmethyl]-benzoic acid
Yield: 81.4% of theory,
M.p.: 197°–201° C.

| | C | H | N |
|---|---|---|---|
| Calc.: | 73.50 | 7.90 | 6.86 |
| Found: | 73.90 | 8.06 | 7.00 |

(aa) 4-[(1-(2-Hexahydroazepino-phenyl)-1-butyl)-aminocarbonylmethyl]-benzoic acid
Yield: 65.6% of theory,
M.p.: 199°–202° C.

| | C | H | N |
|---|---|---|---|
| Calc.: | 73.50 | 7.90 | 6.86 |
| Found: | 73.50 | 7.90 | 6.76 |

(bb) 4-[(1-(4-Fluoro-2-piperidino-phenyl)-1-butyl)-aminocarbonylmethyl]-benzoic acid
Yield: 87.1% of theory,
M.p.: 204°-207° C.

|  | C | H | N |
|---|---|---|---|
| Calc.: | 69.88 | 7.09 | 6.79 |
| Found: | 70.25 | 7.02 | 7.12 |

(cc) 4-[(1-(5-Fluoro-2-piperidino-phenyl)-1-butyl)-aminocarbonylmethyl]-benzoic acid
Yield: 53.9% of theory,
M.p.: 200°-202° C.

|  | C | H | N |
|---|---|---|---|
| Calc.: | 69.88 | 7.09 | 6.79 |
| Found: | 69.67 | 7.24 | 6.90 |

(dd) 3-Chloro-4-[(1-(2-piperidino-phenyl)-1-butyl)-aminocarbonylmethyl]-benzoic acid
Yield: 51% of theory,
M.p.: 165°-168° C.

|  | C | H | N |
|---|---|---|---|
| Calc.: | 67.20 | 6.81 | 6.53 m/e = 428/430 (1 chlorine) |
| Found: | 66.92 | 6.69 | 6.55 m/e = 428/430 (1 chlorine) |

(ee) 4-[(1-(3-Methyl-2-piperidino-phenyl)-1-ethyl)-aminocarbonylmethyl]-benzoic acid
Yield: 79% of theory,
M.p.: 230°-231° C.

|  | C | H | N |
|---|---|---|---|
| Calc.: | 72.60 | 7.42 | 7.36 |
| Found: | 72.75 | 7.58 | 7.30 |

(ff) 4-[(1-(3-Chloro-2-piperidino-phenyl-1)-1-ethyl)-aminocarbonylmethyl]-benzoic acid
Yield: 54% of theory,
M.p.: 192°-195° C. (75% aqueous ethanol)

|  | C | H | Cl | N |
|---|---|---|---|---|
| Calc.: | 65.91 | 6.28 | 8.84 | 6.99 |
| Found: | 66.00 | 6.44 | 8.67 | 6.78 |

Example 81

4-[(2-Methyl-1-(2-piperidino-phenyl)-1-propen-1-yl)-aminocarbonylmethyl]-benzoic acid A mixture of 3.5 gm (8.3 m mol) of ethyl 4-[(2-methyl-1-(2-piperidino-phenyl)-1-propen-1-yl)-aminocarbonylmethyl]-benzoate and 12.5 ml of 1N sodium hydroxide solution in 35 ml of ethanol was stirred at 60° C. for two hours. The mixture was neutralized with 12.5 ml of 1N hydrochloric acid, concentrated by evaporation in vacuo, and distributed between ethyl acetate and water. The dried, filtered organic extract was evaporated in vacuo. The evaporation residue was crystallized from ethanol.
Yield: 2.4 gm (73.6% of theory),
M.p.: 188°-191° C.

|  | C | H | N |
|---|---|---|---|
| Calc.: | 73.44 | 7.19 | 7.14 |
| Found: | 73.60 | 7.19 | 7.02 |

By use of procedures analogous to that of Example 81, the following compounds were prepared:
(a) (E)-4-[(1-(2-Piperidino-phenyl)-1-buten-1-yl)-aminocarbonylmethyl]-benzoic acid
Yield: 71.5% of theory,
M.p.: 188°-190° C.

|  | C | H | N |
|---|---|---|---|
| Calc.: | 73.44 | 7.19 | 7.14 |
| Found: | 73.15 | 7.13 | 7.10 |

Olefinic proton: $^1$N-NMR (CDCl$_3$): δ=6.42 ppm
(b) (Z)-4-[(1-(2-Piperidino-phenyl)-1-buten-1-yl)-aminocarbonylmethyl]-benzoic acid
Yield: 57.8% of theory,
M.p.: 174°-175° C. (ethanol)

|  | C | H | N |
|---|---|---|---|
| Calc.: | 73.44 | 7.19 | 7.14 |
| Found: | 73.54 | 6.97 | 7.17 |

Olefinic proton: $^1$H-NMR (CDCl$_3$): δ=5.60 ppm
(c) (E)-4-[(2-Phenyl-1-(2-piperidino-phenyl)-ethen-1-yl)-aminocarbonylmethyl]-benzoic acid×0.4 H$_2$O
Yield: 33.2% of theory,
M.p.: 165°-167° C. (ether/petroleum ether)

|  |  | C | H | N |
|---|---|---|---|---|
| Calc.: | (× 0.4 H$_2$O) | 75.11 | 6.48 | 6.26 |
| Found: |  | 75.22 | 6.39 | 6.26 |

Olefinic proton: $^1$H-NMR (CDCl$_3$): δ=>6.9 ppm
(d) (Z)-4-[(2-Phenyl-1-(2-piperidino-phenyl)-ethen-1-yl)-aminocarbonylmethyl]-benzoic acid×1 H$_2$O
Yield: 72% of theory,
M.p.: 182°-185° C. (methanol)

|  |  | C | H | N |
|---|---|---|---|---|
| Calc.: | (× 1 H$_2$O) | 73.34 | 6.60 | 6.11 |
| Found: |  | 73.55 | 6.45 | 6.00 |

Olefinic proton: $^1$H-NMR (CDCl$_3$): δ=6.50 ppm
(e) 4-[(3-Phenyl-1-(2-piperidino-phenyl)-1-propen-1-yl)-aminocarbonylmethyl]-benzoic acid
Yield: 48.3% of theory,
M.p.: 162°-164° C. (ether); probably (Z) form

|  | C | H | N |
|---|---|---|---|
| Calc.: | 76.63 | 6.65 | 6.16 |
| Found: | 76.30 | 6.47 | 6.31 |

Olefinic proton: $^1$H-NMR (CDCl$_3$): δ=5.80 ppm
(f) 4-[(1-(2-(3,3-Dimethyl-piperidino)-phenyl)-1-buten-1-yl)-aminocarbonylmethyl]-benzoic acid
Yield: 64.1% of theory,
M.p.: 152°-153° C. (ethyl acetate); probably (Z) form

|       | C     | H    | N    |
|-------|-------|------|------|
| Calc.:| 74.26 | 7.67 | 6.67 |
| Found:| 73.93 | 7.57 | 6.50 |

Olefinic proton: $^1$H-NMR (CDCl$_3$): $\delta$=5.55 ppm (g) (Z)-4-[(1-(6-Methyl-2-piperidino-phenyl)-1-buten-1-yl)-amincarbonylmethyl]-benzoic acid Yield: 53.3% of theory, M.p.: 142°–145° C.

|       | C     | H    | N    |
|-------|-------|------|------|
| Calc.:| 73.66 | 7.44 | 6.89 |
| Found:| 73.56 | 7.73 | 7.15 |

Olefinic proton: $^1$H-NMR (CDCl$_3$): $\delta$=5.38 ppm

Example 82

4-[(1-(2-Piperidino-phenyl)-1-butyl)-aminocarbonylmethyl]-benzoic acid

Two hundred milligrams (0.51 m mol) of 4-[(1-(2-piperidino-phenyl)-1-buten-1-yl)-aminocarbonylmethyl]-benzoic acid in 10 ml of absolute ethanol were hydrogenated over 100 mg of palladium/charcoal (10%) at 50° C. and under 1 bar of hydrogen, with shaking. After one and one-half hours the mixture was filtered and concentrated by evporation in vacuo.

Yield: 68% of theory,

M.p.: 213°–214° C.

|       | C     | H    | N    |
|-------|-------|------|------|
| Calc. | 73.07 | 7.66 | 7.10 |
| Found | 73.21 | 7.82 | 7.02 |

The yield was 56% of theory when hydrogenation was carried out at 50° C. and under 1 bar of hydrogen on Raney nickel.

Example 83

Sodium salt of 4-[(1-(2-piperidino-phenyl)-1-butyl)-aminocarbonylmethyl]-benzoic acid×0.5 H$_2$O Ten grams (25.35 m mol) of 4-[(1-(2-piperidino-phenyl)-1-butyl)-aminocarbonylmethyl]-benzoic acid were dissolved at 50° C. in 200 ml of ethanol, and 25.35 ml of 1N sodium hydroxide solution were added thereto. The mixture was evaporated to dryness in vacuo, and the evaporation residue was dissolved in the minimum amount of ethanol, while being heated over a steam bath. The solution was cooled in an ice bath, and the crystals precipitated were filtered off, washed with ether, and dried at 140° C./15 torr.

Yield: 9 gm (85.3% of theory),

M.p.: 280°–285° C. (decomp.); softening from 255° C.

| (× 0.5 H$_2$O) | | | |
|-------|-------|------|------|
|       | C     | H    | N    |
| Calc. | 67.74 | 6.87 | 6.58 |
| Found | 67.86 | 7.13 | 6.49 |

Example 84

Ethyl (+)-4-[(1-(2-piperidino-phenyl)-1-buty)-aminocarbonylmethyl]-benzoate

To a stirred solution of 2.58 gm (11.1 m mol) of (+)-1-(2-piperidino-phenyl)-1-butylamine [Bp$_{0.03}$: 87° C.; ee=86 (HPLC, after derivatizing with (+)-1-phenethyl-isocyanate)] in 26 ml of acetonitrile, there were successively added, at 20° C., 2.31 gm (1.11 m mol) of 4-ethoxycarbonyl-phenylacetic acid, 3.50 gm (13.3 m mol) of triphenylphosphine, 4.60 ml (33.9 m mol) of triethylamine, and 1.03 ml (11.1 m mol) of carbon tetrachloride. After 14 hours at 20° C. and 1.5 hours at 40° C., the mixture was concentrated by evaporation in vacuo and distributed between water and ether. The organic phase was dried over sodium sulfate, filtered, and concentrated by evaporation in vacuo. The evaporation residue was purified by column chromatography on silica gel [toluene/acetone (6:1)].

Yield: 2.63 gm (56% of theory),

M.p.: 118°–120° C.

|       | C     | H    | N    |
|-------|-------|------|------|
| Calc. | 73.90 | 8.11 | 6.63 |
| Found | 74.02 | 7.97 | 6.51 |

$[\alpha]_D^{20}$ = +9.2° (c=1, methanol)

By use of a procedure analogous to that of Example 84, the following compound was prepared:

Ethyl (−)-4-[(1-(2-piperidino-phenyl)-1-butyl)-aminocarbonylmethyl]-benzoate

Prepared from (−)-1-(2-Piperidino-phenyl)-1-butylamine×1.4 HCl [[$\alpha$]$_D^{20}$=−20.0° (c=1, methanol), Melting range: 90°–100° C.; ee=80 (HPLC, after derivatizing the base with (+)-1-phenethyl-isocyanate)]

Yield: 52.6% of theory,

M.p.: 115°–120° C.

|       | C     | H    | N    |
|-------|-------|------|------|
| Calc. | 73.90 | 8.11 | 6.63 |
| Found | 73.83 | 8.01 | 6.47 |

$[\alpha]_D^{20}$ = −9.0° (c=1, methanol)

Example 85

Ethyl (+)-4-[(1-(2-piperidino-phenyl)-1-butyl)-aminocarbonylmethyl]-benzoate

One gram (3.27 m mol) of (+)-1-(2-piperidino-phenyl)-1-butylamine-dihydrochloride [[$\alpha$]$_D^{20}$=−18.7° (c=1, methanol);

m.p.: decomposition from 115° C.; ee=91.6 (HPLC, after derivatizing the base with (+)-1-phenethyl-isocyanate)] was suspended in 6 ml of methylene chloride, 1.4 ml (10 m mol) of triethylamine were added, with stirring, and then a solution of 0.82 gm (3.64 m mol) of ethoxycarbonyl-phenylacetic acid chloride in 2.4 ml of methylene chloride was added dropwise thereto, whereupon the reaction temperature rose from 22° C. to 38° C. The mixture was stirred for six hours at ambient temperature and then extracted successively in the following manner:

twice with 10 ml of water, once with 10 ml of 2N hydrochloric acid, and once with 10 ml of water.

The organic phase was dried over sodium sulfate, filtered, and concentrated by evaporation in vacuo. The evaporation residue was purified by column chromatography on silica gel [toluene/acetone (6:1)].
Yield: 0.53 gm (38.2% of theory),
M.p.: 120°–122° C.

|  | C | H | N |
|---|---|---|---|
| Calc. | 73.90 | 8.11 | 6.63 |
| Found | 73.96 | 7.98 | 6.61 |

$[\alpha]_D^{20} = +9.0°0$ (c=1, methanol)

Example 86

(+)-4-[(1-(2-Piperidino-phenyl)-1-butyl)-aminocarbonylmethyl]-benzoic acid

Two grams (4.73 m mol) of ethyl (+)-4-[(1-(2-piperidinophenyl)-1-butyl)-aminocarbonylmethyl]-benzoate [$[\alpha]_D^{20} = +9.2$ (c=1, methanol)] in 20 ml of ethanol were stirred with 7.0 ml of 1N sodium hydroxide solution for two and one-half hours in a bath at 65° C. The mixture was cooled, and 7.0 ml of 1N hydrochloric acid were added. The resulting crystals, which precipitated slowly, were filtered off, washed with water, and dried at 100° C./4 torr.
Yield: 1.65 gm (88.2% of theory),
M.p.: 185°–187° C.

|  | C | H | N |
|---|---|---|---|
| Calc. | 73.07 | 7.66 | 7.10 |
| Found | 72.90 | 7.80 | 7.17 |

$[\alpha]_D^{20} = +7.9°$ (c=1, methanol)

By use of a procedure analogous to that of Example 86, the following compound was prepared:
(−)-4-[(1-(2-Piperidino-phenyl)-1-butyl)-aminocarbonylmethyl]-benzoic acid
Yield: 80% of theory,
M.p.: 187°–190° C.

|  | C | H | N |
|---|---|---|---|
| Calc. | 73.07 | 7.66 | 7.10 |
| Found | 72.98 | 7.44 | 7.22 |

$[\alpha]_D^{20} = -7.9°$ (c=1, methanol)

Example 87

4-[(1-(2-Piperidino-phenyl)-1-butyl)-aminocarbonylmethyl]-benzonitrile

Prepared from 1-(2-piperidino-phenyl)-1-butylamine and 4-cyano-phenylacetic acid analogously to Example 73.
Yield: 57.3% of theory,
M.p.: 147°–148° C.

|  | C | H | N |
|---|---|---|---|
| Calc. | 76.76 | 7.78 | 11.19 |
| Found | 76.46 | 7.81 | 11.10 |

By use of a procedure analogous to that of Example 87, the following compound was prepared:
4-[(1-(2-Piperidino-phenyl)-1-butyl)-aminocarbonylmethyl]-toluene
Prepared with 4-tolyl-acetic acid.
Yield: 60.4% of theory,
M.p.: 150°–153° C.

|  | C | H | N |
|---|---|---|---|
| Calc. | 79.08 | 8.85 | 7.68 |
| Found | 78.97 | 8.58 | 7.77 |

Example 88

Ethyl 4-[(1-(2-piperidino-phenyl)-1-butyl)-aminocarbonylmethyl]-benzoate

Prepared from 4-[(1-(2-piperidino-phenyl)-1-butyl)-aminocarbonylmethyl]-benzonitrile with ethanolic hydrochloric acid analogously to Example 68.
Yield: 58% of theory,
M.p.: 127°–128° C.

|  | C | H | N |
|---|---|---|---|
| Calc. | 73.90 | 8.11 | 6.63 |
| Found | 74.07 | 8.23 | 6.87 |

Example 89

Ethyl 4-[(1-(2-piperidino-phenyl)-1-butyl)-aminocarbonylmethyl]-benzoate

Prepared analogously to Example 64 from 1-(2-piperidinophenyl)-1-butanol and ethyl 4-cyanomethyl-benzoate with concentrated sulfuric acid in o-dichlorobenzene at ambient temperature.
Yield: 21% of theory,
M.p.: 126°–128° C.

|  | C | H | N |
|---|---|---|---|
| Calc. | 73.90 | 8.11 | 6.63 |
| Found | 74.12 | 8.20 | 6.45 |

By use of a procedure analogous to that of Example 89, the following compound was prepared:
4-[(1-(2-Piperidino-phenyl)-1-butyl)-aminocarbonylmethyl]-benzoic acid
Prepared from 1-(2-piperidino-phenyl)-1-butanol and 4-cyanomethyl-benzoic acid. Extraction at pH 5.5.
Yield: 29% of theory,
M.p.: 215°–217° C.

|  | C | H | N |
|---|---|---|---|
| Calc. | 73.07 | 7.66 | 7.10 |
| Found | 72.82 | 7.69 | 6.95 |

Example 90

4-[(1-(4-Amino-2-piperidino-phenyl)-1-butyl)-aminocarbonylmethyl]-benzoic acid $\times 0.5$ $H_2O$ An amount of 0.60 gm (1.365 m mol) of 4-[(1-(4-nitro-2-piperidino-phenyl)-1-butyl)-aminocarbonylmethyl]-benzoic acid in 10 ml of dimethylformamide was hydrogenated on 0.1 gm of 10% palladium/charcoal for three hours at 25° C. and under a hydrogen pressure of 1 bar. The catalyst was filtered off using kieselguhr, and the filtrate was concentrated by evaporation in vacuo. The evaporation residue was crystallized from ether.

Yield: 0.41 gm (73.2% of theory),
M.p.: 118°–120° C.

| (× 0.5 H$_2$O) | | | |
|---|---|---|---|
| | C | H | N |
| Calc. | 68.87 | 7.71 | 10.04 |
| Found | 68.62 | 7.64 | 10.08 |

By use of procedures analogous to that of Example 90, the following compounds were prepared:

(a) Ethyl 4-[(1-(4-amino-2-piperidino-phenyl)-1-butyl)-aminocarbonylmethyl]-benzoate
Yield: 81.7% of theory,
M.p.: 145°–146° C. (ether/petroleum ether)

| | C | H | N |
|---|---|---|---|
| Calc. | 71.37 | 8.06 | 9.60 |
| Found | 71.50 | 8.08 | 9.68 |

(b) 4-[(1-(5-Amino-2-piperidino-phenyl)-1-butyl)-aminocarbonylmethyl]-benzoic acid
Yield: 64% of theory,
M.p.: 227°–230° C.

| | C | H | N |
|---|---|---|---|
| Calc. | 70.39 | 7.63 | 10.26 |
| Found | 70.54 | 7.54 | 10.36 |

(c) Ethyl 4-[(1-(5-amino-2-piperidino-phenyl)-1-butyl)-aminocarbonylmethyl]-benzoate
Yield: 84.3% of theory,
M.p.: 162°–165° C.

| | C | H | N |
|---|---|---|---|
| Calc. | 71.37 | 8.06 | 9.60 |
| Found | 71.58 | 7.83 | 9.65 |

Example 91

Ethyl 4-[(1-(5-chloro-2-piperidino-phenyl)-1-butyl)-aminocarbonylmethyl]-benzoate A cold diazonium salt solution (0° C.) was prepared from 2.0 gm (4.57 m mol) of ethyl 4-[(1-(5-amino-2-piperidinophenyl)-1-butyl)-aminocarbonylmethyl]-benzoate in 4.8 ml of semi-concentrated hydrochloric acid and 0.315 gm (4.57 m mol) of sodium nitrite in 1.66 ml of water. This solution was added dropwise, at 0° to 5° C., to a stirred mixture of 0.59 gm (5.94 m mol) of copper(I) chloride and 2.4 ml of conc. hydrochloric acid, and the resulting mixture was then heated in a bath at 50° C. After the development of gas ended (after about 15 minutes), the mixture was cooled, added to ice/conc. ammonia, and extracted four times, each time with 100 ml of ethyl acetate. The combined organic extracts were shaken with water, dried, filtered, and evaporated in vacuo. The evaporation residue was purified by column chromatography on silica gel [toluene/ethyl acetate (10:1)].

Yield: 0.80 gm (40% of theory),
M.p.: 137°–140° C. (ether)

| | C | H | Cl | N |
|---|---|---|---|---|
| Calc. | 68.32 | 7.27 | 7.75 | 6.13 |
| Found | 68.42 | 7.09 | 8.06 | 6.05 |

By use of procedures analogous to that of Example 91, the following compounds were prepared:

(a) Ethyl 4-[(1-(4-chloro-2-piperidino-phenyl)-1-butyl)-aninocarbonylmethyl]-benzoate
Yield: 21.9% of theory,
M.p.: 123°–125° C.

| | C | H | Cl | N |
|---|---|---|---|---|
| Calc. | 68.32 | 7.27 | 7.75 | 6.13 |
| Found | 68.70 | 7.18 | 7.77 | 6.08 |

(b) Ethyl 4-[(1-(-4-bromo-2-piperidino-phenyl)-1-butyl)-aminocarbonylmethyl]-benzoate
Yield: 53.8% of theory,
M.p.: 140°–142° C.

| | C | H | Br | N |
|---|---|---|---|---|
| Calc. | 62.27 | 6.63 | 15.93 | 5.58 |
| Found | 62.39 | 6.78 | 15.85 | 5.59 |

(c) Ethyl 4-[(1-(4-fluoro-2-piperidino-phenyl)-1-butyl)-aminocarbonylmethyl]-benzoate
Yield: 21.6% of theory,
M.p.: 110°–112° C.

| | C | H | N |
|---|---|---|---|
| Calc. | 70.88 | 7.55 | 6.36 |
| Found | 71.01 | 7.53 | 6.21 |

In addition, 40% of ethyl 4-[(1-(4-hydroxy-2-piperidinophenyl)-1-butyl)-aminocarbonylmethyl]-benzoate were isolated (solid foam).

(d) Ethyl 4-[(1-(5-fluoro-2-piperidino-phenyl)-1-butyl)-aminocarbonylmethyl]-benzoate
Yield: 2% of theory,
M.p.: 127°–129° C.

| | |
|---|---|
| Calc. | m/e = 440 |
| Found | m/e = 440 |

(e) 4-[(1-(4-Fluoro-2-piperidino-phenyl)-1-ethyl)-aminocarbonylmethyl]-benzoic acid
Yield: 16.9% of theory,
M.p.: 172°–175° C.

| | C | H | N |
|---|---|---|---|
| Calc. | 68.73 | 6.55 | 7.29 |
| Found | 68.78 | 6.62 | 7.31 |

Example 92

4-[(1-(2-Piperidino-phenyl)-1-butyl)-aminocarbonylmethyl]-benzoic acid

One gram (2.33 m mol) of 4-[(1-(5-chloro-2-piperidinophenyl)-1-butyl)-aminocarbonylmethyl]-benzoic acid in 40 ml of absolute ethanol was hydrogenated on 0.5 gm of 10% palladium/charcoal at 50° C. and under 5 bar of hydrogen. After two hours, the catalyst was filtered off over kieselguhr, and the filtrate was concentrated by evaporation in vacuo. The evaporation residue was distributed at pH 6 between water and ethyl acetate. The organic extract was washed with water, dried, filtered, and evaporated in vacuo.

Yield: 0.61 gm (66% of theory),
M.p.: 213°–215° C.

|       | C     | H    | N    |
|-------|-------|------|------|
| Calc. | 73.07 | 7.66 | 7.10 |
| Found | 73.18 | 7.42 | 7.27 |

The same compound can also be obtained from the corresponding 4-chlorine-, 3-chlorine-, or 6-chlorine-substituted starting products.

Example 93

Ethyl 4-[(1-(4-Methoxy-2-piperidino-phenyl)-1-butyl)-aminocarbonylmethyl]-benzoate A solution of 5.0 gm (11.4 m mol) of ethyl 4-[(1-(4-hydroxy-2-piperidino-phenyl)-1-butyl)-aminocarbonylmethyl]-benzoate in 45 ml of absolute dimethylformamide was added dropwise, under stirring, at ambient temperature, to 548 mg (11.4 m mol) of sodium hydride (50% in oil) in 10 ml of absolute dimethylformamide. The mixture was stirred for a further 15 minutes, and then a solution of 0.71 ml (11.4 m mol) of methyliodide in 8 ml of absolute dimethylformamide was slowly added thereto dropwise. The mixture was stirred for a further two and one-half hours at ambient temperature, evaporated in vacuo, and distributed between water and ether. The ether phase was dried, filtered, and concentrated by evaporation in vacuo. The evaporation residue was purified by column chromatography on silica gel [toluene/acetone (20:1)].

Yield: 1.8 gm (34.9% of theory),
M.p.: 115°–117° C.

|       | C     | H    | N    |
|-------|-------|------|------|
| Calc. | 71.65 | 8.02 | 6.19 |
| Found | 71.47 | 7.86 | 6.19 |

By use of a procedure analogous to that of Example 93, the following compound was prepared:
Ethyl 4-[(1-(5-methoxy-2-piperidino-phenyl)-1-butyl)-aminocarbonylmethyl]-benzoate
Yield: 68.4% of theory,
M.p.: 142°–145° C.

|       | C     | H    | N    |
|-------|-------|------|------|
| Calc. | 71.65 | 8.02 | 6.19 |
| Found | 71.87 | 8.06 | 6.38 |

Example 94

2,3-Dihydroxy-propyl 4-[(1-(2-piperidino-phenyl)-1-butyl)-aminocarbonylmethyl]-benzoate A solution of 2.0 gm (5.07 m mol) of 4-[(1-(2-piperidinophenyl)-1-butyl)-aminocarbonylmethyl]-benzoic acid and 0.85 gm (5.27 m mol) of N,N'-carbonyldiimidazole in 20 ml of absolute tetrahydrofuran was refluxed for one hour, 3.7 ml (50.7 m mol) of glycerol were added, and the resulting mixture was refluxed for a further 15 hours. The mixture was concentrated by evaporation in vacuo and then distributed between water and ethyl acetate, and the organic solution was dried, filtered, and evaporated in vacuo. The evaporation residue was purified by column chromatography on silica gel [toluene/acetone (1:1)].

Yield: 1.1 gm (46.2% of theory),
M.p.: 120°–122° C.

|       | C     | H    | N    |
|-------|-------|------|------|
| Calc. | 69.21 | 7.74 | 5.98 |
| Found | 69.23 | 7.78 | 5.93 |

By use of procedures analogous to that of Example 94, the following compounds were prepared:

(a) 2-Hydroxy-ethyl 4-[(1-(2-piperidino-phenyl)-1-butyl)-aminocarbonylmethyl]-benzoate
Yield: 80% of theory,
M.p.: 125°–127° C.

|       | C     | H    | N    |
|-------|-------|------|------|
| Calc. | 71.21 | 7.81 | 6.39 |
| Found | 71.35 | 7.54 | 6.33 |

(b) 2-Methoxy-ethyl 4-[(1-(2-piperidino-phenyl)-1-butyl)-aminocarbonylmethyl]-benzoate
Yield: 55.9% of theory,
M.p.: 120°–123° C.

|       | C     | H    | N    |
|-------|-------|------|------|
| Calc. | 71.65 | 8.02 | 6.19 |
| Found | 72.03 | 8.03 | 6.24 |

Example 95

2-Nicotinoyloxy-ethyl 4-[(1-(2-piperidino-phenyl)-1-butyl)-aminocarbonylmethyl]-benzoate A solution of 0.7 gm (4.68 m mol) of nicotinic acid chloride in 20 ml of methylene chloride was rapidly added dropwise to a stirred solution of 2.0 gm (4.56 m mol) of 2-hydroxyethyl 4-[(1-(2-piperidino-phenyl)-1-butyl)-aminocarbonylmethyl]-benzoate in 40 ml of methylene chloride and 0.7 ml (4.81 m mol) of triethylamine. The resulting mixture was stirred at 20° C. for two and one-half hours and then extracted with water, and the organic phase was subsequently dried, filtered, and evaporated in vacuo. The evaporation residue was purified by column chromatography on silica gel [toluene/acetone (5:1)].

Yield: 1.1 gm (44% of theory),
M.p.: 132°–135° C.

|  | C | H | N |
|---|---|---|---|
| Calc. | 70.70 | 6.86 | 7.73 |
| Found | 70.82 | 6.82 | 7.91 |

Example 96

4-[(1-(2-Piperidino-phenyl)-1-butyl)-aminocarbonylmethyl]-benzyl alcohol

A solution of 5.0 gm (11.83 m mol) of ethyl 4-[(1-(2-piperidino-phenyl)-1-butyl)-aminocarbonylmethyl]-benzoate in 75 ml of absolute tetrahydrofuran was added dropwise, at an internal temperature of 0° C., to a stirred suspension of 0.68 gm (17.95 m mol) of lithium aluminium hydride in 25 ml of absolute tetrahydrofuran. The mixture was stirred for 20 hours at ambient temperature and then cooled to 0° C., and 4N sodium hydroxide solution was slowly added dropwise thereto until a filterable precipitate formed. The mixture was filtered, and the precipitate was decocted several times with ether. The combined organic solutions were concentrated by evaporation in vacuo. The evaporation residue was distributed between water and ether. The ether phase was dried, filtered, and concentrated by evaporation in vacuo. The evaporation residue was purified by column chromatography on silica gel [toluene/acetone (5:1)].

Yield: 1.0 gm (22% of theory),
M.p.: 152°-154° C.

|  | C | H | N |
|---|---|---|---|
| Calc. | 75.75 | 8.48 | 7.36 |
| Found | 75.90 | 8.45 | 7.28 |

Example 97

4-[(1-(2-Piperidino-phenyl)-1-butyl)-aminocarbonylmethyl]-benzaldehyde

A quantity of 6.6 gm (62 m mol) of sodium carbonate was heated together with 62 ml of ethylene glycol in a bath at 170° C., and, within one minute, 6.2 gm (11 m mol) of $N^1$-[4-[(1-(2-piperidino-phenyl)-1-butyl)-aminocarbonylmethyl]-benzoyl]-$N^2$-tosyl-hydrazine [melting point 195° C. (decomposition)] were added thereto, with rapid stirring, whereupon there was a vigorous development of gas. The mixture was then heated for a further two and one-half minutes at 170° C. and then immediately poured onto ice. It was extracted with ether, and the ether solution was dried, filtered, and concentrated by evaporation in vacuo. The evaporation residue was purified by column chromatography on silica gel [chloroform/acetone (20:1)].

Yield: 2.2 gm (52.9% of theory),
M.p.: 142°-145° C.

|  | C | H | N |
|---|---|---|---|
| Calc. | 76.16 | 7.99 | 7.40 |
| Found | 76.26 | 7.96 | 7.37 |

Example 98

Ethyl 4-[(1-(2-Piperidino-phenyl)-1-butyl)-aminocarbonylmethyl]-cinnamate

A solution of 2.80 gm (12.5 m mol) of ethyl diethylphosphonoacetate in 10 ml of absolute dimethylformamide was added dropwise, at ambient temperature, to 0.60 gm (12.5 m mol) of sodium hydride (50% in oil) in 15 ml of absolute dimethylformamide. The mixture was stirred for 15 minutes (until the development of gas ceased), and then a solution of 2.4 gm (6.34 m mol) of 4-[(1-(2-piperidino-phenyl)-1-butyl)-aminocarbonylmethyl]-benzaldehyde in 10 ml of absolute dimethylformamide was added thereto dropwise. The mixture was stirred for two hours at ambient temperature, concentrated by evaporation in vacuo, and distributed between water and ether. The ether phase was dried, filtered, and then evaporated in vacuo. The evaporation residue was purified by column chromatography on silica gel [toluene/acetone (10:1)].

Yield: 0.85 gm (29.9% of theory),
M.p.: 135°-137° C. (ether/petroleum ether)

|  | C | H | N |
|---|---|---|---|
| Calc. | 74.97 | 8.09 | 6.24 |
| Found | 74.91 | 7.89 | 6.29 |

Example 99

4-[(1-(2-Piperidino-phenyl)-1-butyl)-aminocarbonylmethyl]-cinnamic acid

Prepared by alkaline saponification of ethyl 4-[(1-(2-piperidino-phenyl)-1-butyl)-aminocarbonylmethyl]-cinnamate analogously to Example 80.

Yield: 64% of theory,
M.p.: 180°-183° C.

|  | C | H | N |
|---|---|---|---|
| Calc. | 74.26 | 7.67 | 6.66 |
| Found | 74.03 | 7.47 | 6.80 |

Example 100

Ethyl 3-{4-[(1-(2-piperidino-phenyl)-1-butyl)-aminocarbonylmethyl]-phenyl}-propionate An amount of 0.60 gm (1.34 m mol) of ethyl 4-[(1-(2-piperidino-phenyl)-1-butyl)-aminocarbonylmethyl]-cinnamate was hydrogenated in 10 ml of ethanol on 0.20 gm of 10% palladium/charcoal at ambient temperature under 5 bar of hydrogen. The mixture was filtered and concentrated by evaporation in vacuo.

Yield: 0.53 gm (88% of theory),
M.p.: 98°-99° C. (petroleum ether)

|  | C | H | N |
|---|---|---|---|
| Calc. | 74.63 | 8.50 | 6.22 |
| Found | 74.64 | 8.58 | 6.23 |

By use of a procedure analogous to that of Example 100, the following compound was prepared:

3-{4-[(1-(2-Piperidino-phenyl)-1-butyl)-aminocarbonyl-methyl]-phenyl}-propionic acid
Yield: 63% of theory,
M.p.: 131°-133° C.

|       | C     | H    | N    |
|-------|-------|------|------|
| Calc. | 73.90 | 8.11 | 6.63 |
| Found | 73.96 | 8.30 | 6.56 |

Example 101

3-{4-[(1-(2-Piperidino-phenyl)-1-butyl)-aminocarbonyl-methyl]-phenyl}-propionic acid Prepared by alkaline saponification of ethyl 3-{4-[(1-(2-piperidino-phenyl)-1-butyl)-aminocarbonylmethyl]-phenyl}-propionate analogously to Example 80.
Yield: 50% of theory,
M.p.: 131°-133° C.

|       | C     | H    | N    |
|-------|-------|------|------|
| Calc. | 73.90 | 8.11 | 6.63 |
| Found | 73.82 | 8.07 | 6.41 |

Example 102

Ethyl 4-[(α-aminocarbonyl-2-piperidino-benzyl)-aminocarbonylmethyl]-benzoate

At 20° C., 0.90 gm (5.5 m mol) of N,N'-carbonyldiimidazole were added to a stirred solution of 2.0 gm (4.7 m mol) of ethyl 4-[(α-carboxy-2-piperidino-benzyl)-amnocarbonylmethyl]-benzoate×0.167H₂O (melting point 156°-159° C.) in 20 ml of anhydrous tetrahydrofuran, and the mixture was then heated for half an hour in a bath at 80° C. The mixture was then cooled to 60° C., and at this temperature a vigorous current of dry ammonia was introduced over a period of half an hour. Subsequently the resulting mixture was evaporated in vacuo and distributed between water and chloroform, and then the combined chloroform extracts were shaken with a small amount of water, dried, filtered, and evaporated in vacuo. The evaporation residue was purified by column chromatography on silica gel [chloroform/methanol (5:1)].
Yield: 1.0 gm (50.2% of theory),
M.p.: 160°-162° C. (acetone)

|       | C     | H    | N    |
|-------|-------|------|------|
| Calc. | 68.07 | 6.90 | 9.92 |
| Found | 68.40 | 6.92 | 9.84 |

Example 103

Ethyl 4-[(α-cyano-2-piperidino-benzyl)-aminocarbonylmethyl]-benzoate

Two hundred thirty-four milligrams (1.22 m mol) of 4-toluene-sulfochloride were added in two batches to 520 mg (1.22 m mol) of ethyl 4-[(α-aminocarbonyl-2-piperidino-benzyl)-aminocarbonylmethyl]-benzoate in 0.22 ml of pyridine, and the mixture was heated to 50° C. After two hours and then one hour later, the same quantities of pyridine and 4-toluene-sulfochloride were again added, and the resulting mixture was heated for a further hour at 50° C. After the mixture was left to stand for two days at 20° C., 2N ammonia was added, and the mixture was extracted with chloroform. The chloroform solution was extracted twice with water. After drying and filtering, the solution was concentrated by evaporation in vacuo. The evaporation residue was purified by column chromatography on silica gel [chloroform/methanol (10:1)].
Yield: 325 mg (65.7% of theory),
M.p.: 114°-117° C. (ether/petroleum ether)

|       | C     | H    | N     |
|-------|-------|------|-------|
| Calc. | 71.09 | 6.71 | 10.36 |
| Found | 70.79 | 6.56 | 10.10 |

Example 104

4-[(α-Cyano-2-piperidino-benzyl)-aminocarbonylmethyl]-benzoic acid

One and one-half grams (3.7 m mol) of ethyl 4-[(α-cyano-2-piperidino-benzyl)-aminocarbonylmethyl]-benzoate in 15 ml of dioxane were stirred together with 3.7 ml of 1N sodium hydroxide solution for 45 minutes in a bath at 60° C. and for a further 45 minutes in a bath at 80° C. After cooling with ice, the mixture was combined with 3.7 ml of 1N hydrochloric acid, the dioxane was evaporated off in vacuo, and the residue was distributed between water and chloroform. The organic solution was extracted with a small amount of water, dried, filtered, and concentrated by evaporation in vacuo. The evaporation residue was purified by column chromatography on silica gel [chloroform/ethanol (5:1)].
Yield: 0.50 gm (35.7% of theory),
M.p.: 176°-180° C. (decomp.)

|       | C     | H    | N     |
|-------|-------|------|-------|
| Calc. | 70.01 | 6.14 | 11.13 |
| Found | 70.02 | 6.19 | 11.05 |

Example 105

4-[(1-(2-Piperidino-phenyl)-1-butyl)-aminocarbonylmethyl]-benzoic acid×H₂SO₄

Five milliliters (2.50 m mol) of 1N sulfuric acid were added to a solution of 1.0 gm (2.53 m mol) of 4-[(1-(2-piperidino-phenyl)-1-butyl)-aminocarbonylmethyl]-benzoic acid in 50 ml of ethanol, and the mixture was concentrated to dryness in vacuo and triturated with acetone.
Yield: 0.80 gm (65% of theory),
M.p.: 192°-197° C. (decomp.)

|       | C     | H    | N    | N    |
|-------|-------|------|------|------|
| Calc. | 58.53 | 6.55 | 5.69 | 6.49 |
| Found | 58.05 | 6.54 | 5.49 | 6.35 |

By use of a procedure analogous to that of Example 105, the following compound was prepared:
4-[(1-(2-Piperidino-phenyl)-1-butyl)-aminocrbonylmethyl]-benzoic acid×0.5H₂SO₄×1.5H₂O
Prepared analogously to Example 105 with half the quantity of sulfuric acid.

Yield: 59.3% of theory,
M.p.: 180°–185° C., decomposition at 207°–210° C.

|  | C | H | N | S |
|---|---|---|---|---|
| Calc. | 61.26 | 7.28 | 5.95 | 3.40 |
| Found | 61.28 | 6.99 | 6.10 | 3.23 |

The following examples are illustrative of a few pharmaceutical dosage unit compositions comprising a compound of the present invention, namely, 4-[(1-(2-piperidino-phenyl)-1-butyl)-aminocarbonylmethyl]-benzoic acid, as active ingredient.

Example 106

Tablets Containing 5 mg of Active Ingredient

| Composition of one tablet | |
|---|---|
| Component | Amount (mg) |
| Active ingredient | 5.0 |
| Corn starch | 62.0 |
| Lactose | 48.0 |
| Polyvinyl pyrrolidone | 4.0 |
| Magnesium stearate | 1.0 |
| | 120.0 |

Method of preparation

The active ingredient, the corn starch, the lactose, and the polyvinyl pyrrolidone were mixed and moistened with water. The moist mixture was granulated through a screen of mesh size 1.5 mm and dried at approximately 45° C. The dry granulate was then granulated through a screen of 1.0 mm mesh size and mixed with the magnesium stearate. The finished mixture was pressed into tablets on a tablet press with punches of 7 mm diameter and a unilateral notch.

Weight of each tablet: 120 mg

Example 107

Coated Tablets Containing 2.5 mg of Active Ingredient

| Composition of one coated tablet core | |
|---|---|
| Component | Amount (mg) |
| Active ingredient | 2.5 |
| Potato starch | 44.0 |
| Lactose | 30.0 |
| Polyvinyl pyrrolidone | 3.0 |
| Magnesium stearate | 0.5 |
| | 80.0 |

Method of preparation

The active ingredient, the potato starch, the lactose, and the polyvinyl pyrrolidone were mixed well and moistened with water. The moist mass was granulated through a screen of mesh size 1 mm and dried at approximately 45° C., and the dried granulate was again granulated through the same screen. After addition of the magnesium stearate, coated tablet cores of a diameter of 6 mm and having curvature were pressed on a tablet pressing machine. The coated tablet cores thus prepared were covered in conventional manner with a coating, which coating consisted essentially of sugar and talcum. The finished coated tablets were polished with wax.

Weight of each coated tablet: 120 mg

Example 108

Tablets Containing 10 mg of Active Ingredient

| Composition of one tablet | |
|---|---|
| Component | Amount (mg) |
| Active ingredient | 10.0 |
| Lactose, pulverized | 70.0 |
| Corn starch | 31.0 |
| Polyvinyl pyrrolidone | 8.0 |
| Magnesium stearate | 1.0 |
| | 120.0 |

Method of preparation

A mixture of the active ingredient, the lactose, and the corn starch was moistened with a 20% solution of polyvinyl pyrrolidone in water. The moist mass was granulated through a screen with a mesh size of 1.5 mm and dried at 45° C. The dried granulate was granulated through a screen of 1 mm mesh size and homogeneously mixed with the magnesium stearate.

| Weight of each tablet | 120 mg |
|---|---|
| Punch | 7 mm $\phi$ with a notch |

Example 109

Coated Tablets Containing 5 mg of Active Ingredient

| Composition of one tablet core | |
|---|---|
| Component | Amount (mg) |
| Active ingredient | 5.0 |
| Calcium phosphate secondary | 70.0 |
| Corn starch | 50.0 |
| Polyvinyl pyrrolidone | 4.0 |
| Magnesium stearate | 1.0 |
| | 130.0 |

Method of preparation

A mixture consisting of the active ingredient, the calcium phosphate, and the corn starch was moistened with a 15% solution of polyvinyl pyrrolidone in water. The moist mass was granulated through a screen of 1 mm mesh size, dried at 45° C., and again passed through the same screen. The granulate was mixed with the above-mentioned amount of magnesium stearate, and the mixture thus obtained was pressed into coated tablet cores.

| Weight of each core | 130 mg |
|---|---|
| Punch | 7 mm $\phi$ |

The thus prepared coated tablet cores were covered according to conventional manner with a layer consisting of sugar and talcum. The finished coated tablets were polished with wax.

Weight of each coated tablet: 180 mg.

Any one of the other compounds embraced by Formula I, or a combination thereof, may be substituted for the particular active ingredient employed in Examples 106 through 109. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to those skilled in the art that the invention is not limited to these particular embodiments, and the various changes and modifications may be made without departing from the spirit of the invention or the scope of the claims appended hereto.

We claim:

1. A compound of the formula

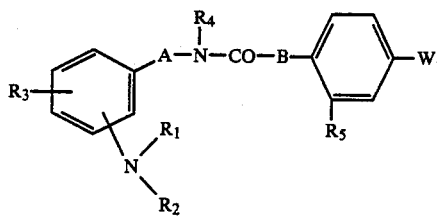

wherein $R_1$ and $R_2$, together with the nitrogen atom to which they are attached, are di(alkyl of 1 to 3 carbon atoms)amino, N-(alkyl of 1 to 3 carbon atoms)-cyclohexylamino, (alkylene of 4 to 5 carbon atoms)-imino, (monomethyl-substituted alkylene of 4 to 5 carbon atoms)-imino, (dimethyl-substituted alkylene of 4 to 5 carbon atoms)-imino, 4-hydroxy-piperidino, piperid-4-on-1-yl, tetrahydropyridino, morpholino, thiomorpholino, N-methyl-piperazino, N-benzyl-piperazino, N-chlorophenyl-piperazino, hexamethyleneimino, heptamethyleneimino, octamethyleneimino, 3-aza-bicyclo[3,2,2]nonan-3-yl, 1,2,3,4-tetrahydro-isoquinolin-2-yl, 1,2,3,4,5,6,7,8-octahydro-isoquinolin-2-yl, decahydro-isoquinolin-2-yl, octahydroisoindol-2-yl or 8-aza-1,4-dioxa-spiro[4,5]decan-8-yl;

$R_3$ is hydrogen, fluorine, chlorine, bromine, iodine, methyl, hydroxyl, methoxy, benzyloxy, acetoxy, nitro, amino, acetylamino, methylsulfonylamino, benzoylamino, ethoxycarbonylamino, cyano, carboxyl, ethoxycarbonyl, aminocarbonyl or aminosulfonyl;

$R_4$ is hydrogen or methyl;

$R_5$ is hydrogen or, when W is carboxyl or (alkoxy of 1 to 4 carbon atoms) carbonyl, also chlorine;

A is a single bond, dimethyl-methylene, ethylene,

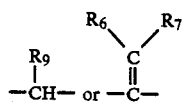

$R_6$ and $R_7$ are hydrogen or, together with the carbon atom to which they are attached, alkylidene of 2 to 5 carbon atoms, phenyl(alkylidene of 1 to 3 carbon atoms) or cyclohexylidene;

$R_9$ is hydrogen, alkyl of 1 to 5 carbon atoms, alkenyl of 3 to 5 carbon atoms, phenyl, halophenyl, methylphenyl, hydroxyphenyl, methoxyphenyl, benzyloxyphenyl, 4-methylmercaptophenyl, pyridyl, cyclohexyl, carboxyl, cyano, aminocarbonyl, methoxycarbonyl, ethoxycarbonyl, hydroxymethyl, methoxymethyl or phenyl(alkyl of 1 to 2 carbon atoms);

B is methylene, ethylidene or ethylene; and

W is methyl, hydroxymethyl, formyl, acetyl, carboxyl, cyano, 2-carboxy-ethenyl, 2-(alkoxy of 1 to 3 carbon atoms-carbonyl)-ethenyl, carboxy(alkyl of 1 to 2 carbon atoms), (alkoxy of 1 to 3 carbon atoms-carbonyl)-(alkyl of 1 to 2 carbon atoms), di(alkoxy of 1 to 3 carbon atoms-carbonyl)-(alkyl of 1 to 2 carbon atoms), (2,2-dimethyl-dioxolan-4-yl)methoxy-carbonyl, benzyloxy-carbonyl, aminocarbonyl, methylamino-carbonyl, dimethylaminocarbonyl, piperidino-carbonyl, morpholino-carbonyl, (alkoxy of 1 to 4 carbon atoms)-carbonyl; (mono- or dihydroxy-substituted alkoxy of 1 to 4 carbon atoms)-carbonyl, where individual methyl or methylene groups of the alkyl moiety are monohydroxy-substituted and the methylene group adjacent the oxygen atom is unsubstituted; or

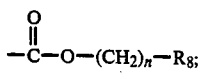

n is 2, 3 or 4; and $R_8$ is methoxy, ethoxy, nicotinoyloxy, 1,3-dimethyl-xanthine-7-yl, dimethylamino or diethylamino;

or a non-toxic, pharmacologically acceptable addition salt thereof.

2. A compound of claim 1, which is of the formula

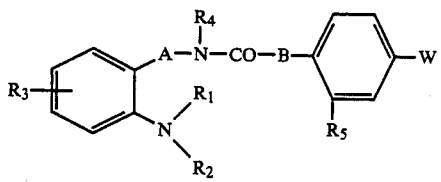

wherein $R_1$, $R_2$, $R_3$, $R_4$, $R_5$, A, B and W have the meanings defined in claim 1, or a non-toxic, pharmaceutically acceptable addition salt thereof.

3. A compound of claim 2, wherein $R_1$ and $R_2$, together with the nitrogen atom to which they are attached, are dimethylamino, (alkylene of 4 to 5 carbon atoms)-imino, (monomethyl-substituted alkylene of 4 to 5 carbon atoms)-imino, (dimethyl-substituted alkylene of 4 to 5 carbon atoms)-imino, tetrahydropyridino, hexamethyleneimino, heptamethyleneimino, octamethyleneimino, or octahydro-isoindol-2-yl;

$R_3$ is hydrogen, fluorine, chlorine, methyl, or methoxy;

$R_4$ is hydrogen;

$R_5$ is hydrogen;

A is

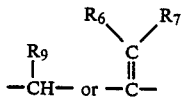

$R_6$ and $R_7$ are hydrogen or, together with the carbon atom to which they are attached, alkylidene of 2 to 5 carbon atoms, phenyl(alkylidene of 1 to 3 carbon atoms) or cyclohexylidene;

R$_9$ is hydrogen, alkyl of 1 to 5 carbon atoms, alkenyl of 3 to 5 carbon atoms, phenyl, fluorophenyl, chlorophenyl, bromophenyl, methylphenyl, hydroxyphenyl, methoxyphenyl, benzyloxyphenyl, 4-methylmercaptophenyl, pyridyl, cyclohexyl, carboxyl, cyano, aminocarbonyl, methoxycarbonyl, ethoxycarbonyl, hydroxymethyl, methoxymethyl, or phenyl(alkyl of 1 to 2 carbon atoms);

B is methylene; and

W is methyl, hydroxymethyl, formyl, carboxyl, cyano, 2-carboxy-ethenyl, 2-(alkoxy of 1 to 3 carbon atoms-carbonyl)-ethenyl, 2-carboxy-ethyl, (alkoxy of 1 to 3 carbon atoms-carbonyl)-(alkyl of 1 to 2 carbon atoms), (2,2-dimethyl-dioxolan-4-yl)methoxy-carbonyl, (alkoxy of 1 to 4 carbon atoms)-carbonyl; (mono- or dihydroxy-substituted alkoxy of 1 to 4 carbon atoms)-carbonyl, where individual methyl or methylene groups of the alkyl moiety are monohydroxy-substituted and the methylene group adjacent the oxygen atom is unsubstituted; or

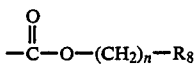

where n is 2 or 3, and

R$_8$ is methoxy, diethylamino, nicotinoyloxy, or 1,3-dimethyl-xanthine-7-yl;

or a non-toxic, pharmacologically acceptable addition salt thereof.

4. A compound of claim 3, where

R$_1$, R$_2$, R$_3$, R$_4$, R$_5$, A and B have the meanings defined in claim 40; and W is carboxyl; (alkoxy of 1 to 4 carbon atoms)-carbonyl; or (mono- or dihydroxy-substituted alkoxy of 1 to 4 carbon atoms)-carbonyl, where individual methyl or methylene groups of the alkyl moiety are monohydroxy-substituted and the methylene group adjacent the oxygen atom is unsubstituted;

or a non-toxic, pharmacologically acceptable addition salt thereof.

5. A compound of claim 3, where

R$_1$ and R$_2$, together with the nitrogen atom to which they are attached, are pyrrolidino, methyl-pyrrolidino, piperidino, methyl-piperidino, dimethyl-piperidino, tetrahydropyridino or hexamethyleneimino;

R$_3$ is hydrogen, fluorine, chlorine, methyl or methoxy;

R$_4$ is hydrogen;

R$_5$ is hydrogen;

A is

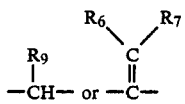

R$_6$ and R$_7$ are hydrogen or, together with the carbon atom to which they are attached, alkylidene of 2 to 5 carbon atoms, phenyl(alkylidene of 1 to 3 carbon atoms) or cyclohexylidene;

R$_9$ is hydrogen, alkyl of 1 to 5 carbon atoms, phenyl, fluorophenyl, chlorophenyl, methylphenyl, or pyridyl;

B is methylene; and

W is methyl, hydroxymethyl, formyl, carboxyl, cyano, 2-carboxy-ethenyl, 2-(alkoxy of 1 to 3 carbon atoms-carbonyl)-ethenyl, 2-carboxy-ethyl, (alkoxy of 1 to 3 carbon atoms-carbonyl)-(alkyl of 1 to 2 carbon atoms), (2,2-dimethyl-dioxolan-4-yl)-methoxy-carbonyl, (alkoxy of 1 to 4 carbon atoms)-carbonyl; (mono- or dihydroxy-substituted alkoxy of 1 to 4 carbon atoms)-carbonyl, where individual methyl or methylene groups of the alkyl moiety are monohydroxy-substituted and the methylene group adjacent the oxygen atom is unsubstituted;

or a non-toxic, pharmacologically acceptable addition salt thereof.

6. A compound of claim 5, where

R$_1$, R$_2$, R$_3$, R$_4$, R$_5$, A and B have the meanings defined in claim 5, and W is carboxyl or (alkoxy of 1 to 4 carbon atoms)-carbonyl;

or a non-toxic, pharmacologically acceptable addition salt thereof.

7. A compound of claim 6, where

R$_1$, R$_2$, R$_3$, R$_4$, R$_5$ and B have the meanings defined in claim 6;

A is methyl-methylene, ethyl-methylene, n-propyl-methylene, n-butyl-methylene or phenyl-methylene; and W is carboxyl;

or a non-toxic, pharmacologically acceptable addition salt thereof.

8. A compound of claim 1, which is 4-[(1-(2-piperidino-phenyl)-1-ethyl)-aminocarbonylmethyl]-benzoic acid, an alkyl of 1 to 3 carbon atoms ester thereof or a non-toxic, pharmaceutically acceptable addition salt thereof.

9. A compound of claim 1, which is 4-[(2-piperidinobenzhydryl)-aminocarbonylmethyl]-benzoic acid, an alkyl of 1 to 3 carbon atoms ester thereof or a non-toxic, pharmaceutically acceptable addition salt thereof.

10. A compound of claim 1, which is 4-[(1-(2-piperidino-phenyl)-1-butyl)-aminocarbonylmethyl]-benzoic acid, an alkyl of 1 to 3 carbon atoms ester thereof or a non-toxic, pharmaceutically acceptable addition salt thereof.

11. A hypoglycemic pharmaceutical composition consisting essentially of an inert pharmaceutical carrier and an effective hypoglycemic amount of a compound of claim 1.

12. The method of lowering the blood sugar level in a warm-blooded animal host in need thereof, which comprises perorally or parenterally administering to said host an effective hypoglycemic amount of a compound of claim 1.

13. A hypoglycemic pharmaceutical composition consisting essentially of an inert pharmaceutical carrier and an effective hypoglycemic amount of a compound of claim 3.

14. The method of lowering the blood sugar level in a warm-blooded animal host in need thereof, which comprises perorally or parenterally administering to said host an effective hypoglycemic amount of a compound of claim 3.

15. A hypoglycemic pharmaceutical composition consisting essentially of an inert pharmaceutical carrier and an effective hypoglycemic amount of a compound of claim 7.

16. The method of lowering the blood sugar level in a warm-blooded animal host in need thereof, which comprises perorally or parenterally administering to said host an effective hypoglycemic amount of a compound of claim 7.

* * * * *

UNITED STATES PATENT AND TRADEMARK OFFICE
CERTIFICATE OF CORRECTION

PATENT NO. : 4,735,959
DATED : April 5, 1988
INVENTOR(S) : Grell et al.

It is certified that error appears in the above-identified patent and that said Letters Patent is hereby corrected as shown below:

Col. 2, line 9 - correct "1 to 6 carbon" to read -- 1 to 7 carbon --.

Col. 28, line 45 - correct "methyl-" to read -- methyl] --.

Col. 34, line 34 - correct "Hexahydroazapino to read -- Hexahydroazepino --.

Col. 43, line 39 - delete "p0" from in front of -- (f) --.

Col. 83, line 68 - insert "M.p." before -- 90°-95° --.

Col. 108, line 10 - correct "(1.11 m mol)" to read -- 11.1 m mol --.

Col. 108, line 55 - correct "-18.7" to read -- +18.7 --.

Col. 123, line 33, Claim 4 - correct "40" to read -- 3 --.

Signed and Sealed this

Twenty-eighth Day of February, 1989

Attest:

DONALD J. QUIGG

*Attesting Officer*  *Commissioner of Patents and Trademarks*